United States Patent
Arculus-Meanwell et al.

(10) Patent No.: US 8,680,052 B1
(45) Date of Patent: Mar. 25, 2014

(54) METHODS OF TREATING, REDUCING THE INCIDENCE OF, AND/OR PREVENTING ISCHEMIC EVENTS

(71) Applicant: The Medicines Company, Parsippany, NJ (US)

(72) Inventors: Clive Arthur Arculus-Meanwell, Bernardsville, NJ (US); Simona Skerjanec, Basel (CH); Jayne Prats, Carlisle, MA (US); David J. Schneider, Colchester, VT (US)

(73) Assignee: The Medicines Company, Parsippany, NJ (US)

( * ) Notice: Subject to any disclaimer, the term of this patent is extended or adjusted under 35 U.S.C. 154(b) by 0 days.

(21) Appl. No.: 13/904,778

(22) Filed: May 29, 2013

Related U.S. Application Data

(63) Continuation-in-part of application No. 13/792,056, filed on Mar. 9, 2013.

(60) Provisional application No. 61/815,735, filed on Apr. 25, 2013.

(51) Int. Cl.
*A61K 38/00* (2006.01)

(52) U.S. Cl.
USPC ........ 514/14.7; 514/14.9; 514/15.3; 514/16.4

(58) Field of Classification Search
None
See application file for complete search history.

(56) References Cited

U.S. PATENT DOCUMENTS

| | | |
|---|---|---|
| 2007/0082840 A1 | 4/2007 | Porter et al. |
| 2007/0254324 A1 | 11/2007 | Rechner |
| 2011/0112030 A1 | 5/2011 | Arculus-Meanwell et al. |
| 2012/0141468 A1 | 6/2012 | Chen et al. |
| 2013/0040898 A1 | 2/2013 | Johansson |
| 2013/0190265 A1 | 7/2013 | Arculus-Meanwell et al. |

FOREIGN PATENT DOCUMENTS

WO WO-2013-025476 2/2013

OTHER PUBLICATIONS

Steinhubl et al. Cardiovascular Drug Reviews vol. 25, No. 2, pp. 188-203, 2007.*
Park et al. Current Treatment Options in Cardiovascular Medicine, 2007.*
Cattaneo M. Platelet P2 receptors old and new targets for antithrombotic drugs, Expert Rev Cardiovasc Ther. 2007, pp. 45-55, vol.. 5, No. 1.
Diaz-Ricart M, Cangrelor tetrasodium, Drugs of the Future, 2008, pp. 101-110, vol. 33, No. 2.
Dovlatova N, Wijeyeratne YD, Fox SC, et al., Detection of P2Y(14) protein in platelets and investigation of the role of P2Y(14) in platelet function in comparions with the EP(3) receptor, Thromb Haemost, 2008, pp. 261-270, vol. 100.
Humphries RG, Pharmacology of AR-C6993IMX and related compounds: from pharmacological tools to clinical trials, Haematologica. 2000, pp. 66-72, 85(the Platelet ADP Receptors Supp.).
Ingall, AH, P2T receptor antagonisis: novel inhibitors of platelet aggregation, Arch Pharm, 1999, pp. 11-12, Supp. 1.
Ingall AH, Dixon J. Bailey A. et al., Antagonists of the platelet P2T receptor: a novel approach to antithrombotic therapy, J Med Chem. 1999, pp. 213-220, vol. 42.
Kuupers MI, Nieuwenhuys CM, Feuge MA, et al., Regulation of tissue factor-induced coagulation and platelet aggregation in flowing whole blood, Thromb Haemost, 2005: 93, pp. 97-105.
Kunapuli SP, Ding Z, Dorsam RT, et al., ADP receptors target for developing antithrombotic agents, Curr Pharm Des. 2003, vol. 9, pp. 2303-2316.
Penz SM, Reinnger Ai, Toth O. et al., Glycoprotein Ihα inhibition and ADP receptor antagonists, but not aspirin, reduce platelet thrombus formation in flowing blood exposal to atheroselerotic plaques. Thromb Haemost, 2007, pp. 435-443, vol. 97.
Storey RF, Oldroyd KG, Wolcox RG, Open multicentre study of the P21 receptor antagonist AR-C69931MX Assessing safety, tolerability and activity in patients with acute coronary syndromes, Thromb Haemost, 2001, pp. 401-407, vol. 85.
Storey RF, Judge HM, Wilcox RG, et al., Inhibition of ADP-induces p-selection expression and platelet-leukocyte conjugate formation by clopidogrel and the P2Y12 receptor antagonist AR-C69931MX but not aspirin. Thromb Res. 2002, pp. 488-494, vol. 88.
Ueno M. Ferreiro JL, Angiolillo DJ, Update on the Clinical Development of Cangrelor, Expert Rev Cardiovasc, 2010, pp. 1069-1077, vol. 81.
Ferreiro JL, Ueno M. Angiolillo DJ, Cangrelor: a review on its mechanism of action and clinical development, Expert Rev Cardiovasc Ther. 2009, pp. 1195-1201, vol. 7.
Oestreich JH, Steinhubl SR, Cangrelor in percutaneous coronary intervention, Expert Rev Clin Pharmcol, 2009, pp. 137-145, vol. 2.

(Continued)

*Primary Examiner* — Cecilia J Tsang
*Assistant Examiner* — Li Lee
(74) *Attorney, Agent, or Firm* — Frommer Lawrence & Haug LLP

(57) ABSTRACT

Methods of treating, reducing the incidence of, and/or preventing an ischemic event in a patient undergoing percutaneous coronary intervention (PCI), comprising administering to the patient a pharmaceutical composition comprising cangrelor. The method may further comprise administering an additional therapeutic agent to the patient, the additional therapeutic agent comprising a $P2Y_{12}$ inhibitor. Pharmaceutical compositions useful for treating, reducing the incidence of, and/or preventing an ischemic event in a patient undergoing PCI. The pharmaceutical compositions comprise cangrelor. Methods of preparing a pharmaceutical composition for treating, reducing the incidence of, and/or preventing an ischemic event in a patient undergoing PCI, comprising admixing cangrelor with one or more pharmaceutically acceptable excipients. An ischemic event may include stent thrombosis, myocardial infarction, ischemia-driven revascularization, and mortality.

30 Claims, 24 Drawing Sheets

(56) References Cited

OTHER PUBLICATIONS

Ahrens I, Bode C, Novel antiplatelet therapies following percutaneous coronary interventions, Curr Opin Investig Drugs, 2009, pp. 902-911, vol. 10.
Akers Ws, Oh JJ, Oestreich JH, et al., Pharmacokinetics and pharmacodynamics of a bolus and infusion of cangrelor: a direct, parenteral P2Y12 receptor antagonist, J Clin Pharm, 2010, pp. 27-35, vol. 50.
Angiolillo DJ, Schneider DJ, Bhatt DL, et al., Pharmacodynamic effects of cangrelor and clopidogrel: the platelet function substudy from the cangrelor versus standard therapy to achieve optimal management of platelet inhibition (CHAMPION) trials, J Thromb Thrombolysis, 2012, pp. 44-55, vol. 44.
Angiolillo DJ, Firstenberg MS, Price MJ, et al., Bridging antiplatelet therapy with cangrelor in patients undergoing cardiac surgery, JAMA, 2012, pp. 265-274 and Supplemental Online Content, vol. 307, No. 3.
Bellemain-Appaix A, Brieger D, Beygiu F, et al., New P2Y12 inhibitors versus clopidogrel in percutaneous coronary intervention. A meta-analysis, J Am Coll Cardiol, 2010, pp. 1542-1551, vol. 56.
Bhatt DL, Lincoff AM, Gibson CM, et al., Intravenous platelet blockade with cangrelor during PCI, N Engl J Med, 2009, pp. 2330-2341, vol. 361.
Buckland RJ, Judge HM, Sugidachi A, et al., Reversible binding of cangrelor to the P2Y12 receptor prevents the binding of clopidogrel and prasugrel active metabolites, J Thromb Haemost, 2009, p. 942, vol. 7(Suppl 2).
Buckland R, Judge HM, Sugidachi A, et al., Cangrelor inhibits the binding of clopidogrel and prasugrel active metabolites to the P2Y12 receptor, Eur Heart J, 2009, p. 193, vol. 30(Suppl 1).
Desai NR, Bhatt DL, The state of periprocedural antiplatelet therapy after recent trials, J Am Coll Cardiol Intv, 2010, pp. 571-583, vol. 3.
Faxon DP, Cangrelor for ACS—lessons from the CHAMPION trials, Nat Rev Cardiol, 2010, pp. 124-125, vol. 7.
Fox SC, May JA, Johnson A, et al., Effects on platelet function of an EP3 receptor antagonist used alone and in combination with a P2Y12 antagonist both in-vitro and ex-vivo in human volunteers, Platelets, 2013, pp. 392-400, vol. 24, No. 5.
Norgard NB, Cangrelor: a novel P2Y12 receptor antagonist, Expert Opin Investig Drugs, 2009, pp. 1219-1230, vol. 18.
Oliphant CS, Doby JB, Blade CL, et al., Emerging P2Y12 receptor antagonists:role in coronary artery disease, Curr Vasc Pharmacol, 2010, pp. 93-101, vol. 8.
Paikin JS, Eikelboom JW, Cairns JA, et al., New antithrombotic agents-insights from clinical trials, Nat Rev Cardiol, 2010, pp. 498-509, vol. 7.
Ravnefjord A, Delavaux P, Tornvall J, et al., Ongoing treatment with cangrelor, but not ticagrelor, is associated with a significant reduction in the efficacy of clopidogrel in an ex-vivo canine model, J Thromb Haemost, 2009, p. 349, vol. 7(Suppl 2).
Ravnefjord A, Weilitz J, Emanuelsson BM, et al., Evaluation of ticagrelor pharmacodynamic interactions with reversibly binding or non-reversibly binding P2Y12 antagonists in an ex-vivo canine, Thromb Res, 2012, pp. 622-628, vol. 130.
Sabatine MS, Novel antiplatelet strategies in acute coronary syndromes, Clev Clin J Med, 2009, pp. S8-S15, vol. 76(suppl 1).
Siddique A, Butt M, Shantsila E, et al., New antiplatelet drugs: beyond aspirin and clopidogrel, Int J Clin Pract, 2009, pp. 776-789, vol. 63.
Van Giezen JJ, Humphries RG, Preclinical and clinical studies with selective reversible direct P2Y12 antagonists, Semin Thromb Hemost, 2005, pp. 195-204, vol. 31, No. 2.
Van Giezen JJ, Optimizing platelet inhibition, Eur Heart J, 2008, pp. D23-D29, vol. 10(Suppl D).
Vasiljev KS, Uri A, Laitinen JT, 2-Alkylthio-substituted platelet P2Y12 receptor antagonists reveal pharmacological identity between the rat brain Gi-linked ADP receptors and P2Y12, Neuropharmcol, 2003, pp. 145-154, vol. 45, No. 1.

Wang K, Zhou X, Zhou Z, et al.,Blockade of the platelet P2Y12 receptor by AR-C69931MX sustains coronary artery recanalization and improves the myocardial tissue perfusion in a canine thrombosis model, Arterioscler Thromb Vasc Biol, 2003, pp. 357-362, vol. 23, No. 1.
Wang K, Zhou X, Zhou Z, et al., Sustained coronary artery recanalization with adjunctive infusion of a novel P2T-receptor antagonist AR-C69931 in a canine model, JACC, 2000, pp. 281A-82A, vol. 35(2 Suppl).
Wang K, Zhou X, Zhou Z, et al., Blockade of the ADP P2T receptor sustains coronary artery recanalization and improves the myocardium tissue perfusion in the canine thrombosis model, Circulation, 2001, p. 96, vol. 104 (17 Suppl).
Weaver WD, Becker R, Harrington R, et al., Safety and efficacy of a novel direct P2T receptor antagonist, AR C6991MX, in patients undergoing percutaneous coronary intervention, Eur Heart J, 2000, p. 382, vol. 21 (Suppl).
Weaver WD, Harrington RA, Grines CL, et al., Intravenous AR C69931MX, a novel P2T platelet receptor antagonist, in patients undergoing percutaneous coronary interventions preliminary results from a placebo or active controlled trial, JACC, 2000, pp. 36A-37A, vol. 35 (2SupplA).
Wiviott SD, De Lemos JA, Antiplatelet agents make a comeback in ST-elevation myocardial infarction, Am Heart J, 2007, pp. 603-606, vol. 154.
Wiviott SD, Michelson AD, Berger PB, et al., Therapeutic goals for effective platelet inhibition: a consensus document, Rev Cardiovasc Med, 2006, pp. 214-225, vol. 7.
Bhatt DL, Stone GW, Mahaffey KW, et al. Effect of platelet inhibition with cangrelor during PCI on ischemic events. N Engl J Med, 2013, pp. 1303-1313, vol. 368.
Iyu D, Glenn Jr, White AE, et al., Mode of action of P2Y12 antagonists as inhibitors of platelet function, Thromb Haemost, 2011, pp. 96-105, vol. 105.
Penz SM, Reininger AJ, Toth O, et al., Glycoprotein Ibα inhibition and ADP receptor antagonists, but not aspirin, reduce platelet thrombus formation in flowing blood exposed to atherosclerotic plaques, Thromb Haemost, 2007, pp. 435-443, vol. 97.
Nopgard NB, Abu-Fadel M, Future prospects in anti-platelet therapy: A review of potential P2Y12 and thrombin receptor antagonists, Recent Patents Cardiovasc Drug Discovery, 2008, pp. 194-200, vol.3.
Leonardi S, Stebbins A Lopes RD, et al., Maintenance therapy with thienopyridines may reduce enzymatic infarct size in patients with acute coronary syndrome undergoing PCI: Insights form teh CHAMPION PCI trial AHA Chicago, IL, 2010.
Abbracchio MP, et al., International union of pharmacology LVIII: update on the P2Y G protein-coupled nucleotide receptors: from molecular mechanisms and pathophysiology to therapy, Pharmacol Rev, 2006, pp. 281-341,vol. 58, No. 3.
Aleil B, et al., Flow cytometric analysis of intraplatelet VASP phosphorylation for the detection of clopidogrel resistance in patients with ischemic cardiovascular diseases, J Thromb Haemost, 2005, pp. 85-92.
Angiolillo DJ, ADP Receptor Antagonism. What's in the Pipeline?, Am J Cardiovasc Drugs, 2007, pp. 423-432. vol. 7 No. 6.
U.S. Appl. No. 13/391,287, filed Jun. 28, 2013, Ruderman Chen et al.
U.S. Appl. No. 13/391,384, filed Jun. 28, 2013, Ruderman Chen et al.
U.S. Appl. No. 13/954,821, filed Jul. 30, 2013, Ruderman Chen et al.
U.S. Appl. No. 13/954,843, filed Jul. 30, 2013, Ruderman Chen et al.
Angiolillo DJ, et al., Pharmacology of emerging novel platelet inhibitors, Am Heart J, 2008, pp. S10-S15, vol. 156, No. 2, Supp. 1.
Angiolillo DJ, et al., Clinical overview of promising nonthienopyridine antiplatelet agents, Am Heart J, 2008, pp. S23-S28, vol. 156, No. 2, Supp 1.
Becker RC, Platelet surface physiology and its importance in pharmacotherapy design and development: The adenosine diphosphate receptor antagonists, J Thromb Thrombolysis, 2000, pp. 35-53.
Boeynaems JM, Van Giezen H, Savi P, Herbert JM, P2Y receptor antagonists in thrombosis, Curr Opin Investig Drugs, 2005, pp. 275-282, vol. 6, No. 3.
Chattaraj SC, Cangrelor astra Zeneca, Curr Opin Investig Drugs, 2001, pp. 250-255, vol. 2, No. 2.

(56) References Cited

OTHER PUBLICATIONS

Christensen K, Larsson R, Emanuelsson H, et al., Effects on blood compatibility in vitro by combining a direct P2Y12 receptor inhibitor and heparin coating of stents, Platelets, 2006, pp. 318327, vol. 17, No. 5.
Cohen M, Diez J, Levine GN, et al., Pharmacoinvasive management of acute coronary syndrome: incorporating the 2007 ACC/AHA Guidelines. The CATH (Cardiac Catherization and Antithrombotic Therapy in the Hospital) Clinical Consensus Panel Report-III, J Invasive Cardiology, 2007, pp. 525-540, vol. 19, No. 12.
Dalal AR, D'Souza S, Shulman MS, Brief review: coronary drug-eluting stents and anesthesia, Can J Anaest, 2006, pp. 1230-1243, vol. 53, No. 12.
Ding Z, Kim S, Kunapuli SP, Identification of a potent inverse agonist at a constitutively active mutant of human P2Y12 receptor, Mol Pharmacol, 2005, pp. 338-345, vol. 69, No. 1.
Dovlatova NL, Jakubowski JA, Sugidachi A, et al., The reversible P2Y12 antagonist cangrelor influences the ability of the active metabolites of clopidogrel and prasugrel to produce irreversible inhibition of platelet function, J Thromb Haemost, 2008, pp. 1153-1159, vol. 6.
Dovlatova N, Wijeyeratne YD, Fox SC, et al., Detection of P2Y(14) protein in platelets and investigation of the role of P2Y(14) in platelet function in comparison with the EP(3) receptor, Thromb Haemost, 2008, pp. 261-270, vol. 100.
Fugate SE, Cudd LA, Cangrelor for treatment of coronary thrombosis, Ann Pharmacother, 2006, pp. 925-930, vol. 40.
Gitt AK, Betriu A., Antiplatelet therapy in acute coronary syndromes, Eur Heart J, 2008, pp. A4-A12, 10 Supp. A.
Greenbaum AB, Ohman EM, Gibson CM, et al., Preliminary experience with intravenous P2Y12 platelet receptor inhibition as an adjunct to reduced-dose alteplase during acute myocardial infarction: Results of the Safety, Tolerability and Effect on Patency in Acute Myocardial Infarction (STEP-AMI) angiographic trial, Am Heart J, 2007 pp. 702-709, vol. 54, No. 4.
Greenbaum AB, Grines CL, Bittl JA, et al., Initial experience with an intravenous P2Y12 platelet receptor antagonist in patients undergoing percutaneous coronary intervention: Results from a 2-part, phase II, multicenter, randomized, placebo- and active-controlled trial, Am Heart J, 2006, pp. 689.e1-689.e10.
Greenbaum AB, Ohman EM, Gibson MS, et al., Intravenous adenosine diphosphate P2T platelet receptor antagonism as an adjunct to fibrinolysis for acute myocardial infarction, JACC, 2002, pgs., vol. 39, Issue 5, Supp. A.
Huang J, Driscoll EM, Gonzales ML, Prevention of arterial thrombosis by intravenously administered platelet P2T receptor antagonist AR-C66931MX in a canine model, J Pharmacol Exp Ther, 2000, pp. 492-499, vol. 295, No. 2.
Jacobsson F, Swahn E, Wallentin L, et al., Safety profile and tolerability of intravenous AR C69931MX, a new antiplatelet drug, in unstable angina pectoris and non Q wave myocardial infarction, Clin Ther, 2002, pp. 752-765, vol. 24, No. 5.
Jacobsson F, Dellborg M, Swahn E, et al., JACC, 2000, p. 343, vol. 35, Issue, 2, Supp. A.
Jarvis GE, Nassim MA, Humphries RG, et al., The P2T antagonist AR C69931MX is a more effective inhibitor of ADP induced platelet aggregation than clopidogrel, Blood, 1999, p. 194, (10 Supp. pt. 1):22a.
Jarvis GE, Nassim MA, Humphries RG, et al., Superior inhibition of ADP induced human platelet aggregation by AR C69931MX than clopidogrel, Drug Dev Res, 2000, p. 90. vol. 50, No. 1.
Judge HM, Buckland RJ, Holgate CE, et al, Glycoprotein IIb/IIIa and P2Y12 receptor antagonists yield additive inhibition of platelet aggregation, granule secretion, soluble CD40L release and procoagulant responses, Platelets, 2005, pp. 398-407, vol. 16, No. 7.
Kandzari DE, Evolving antithrombotic treatment strategies for acute ST-elevation myocardial infarction, Rev Cardiovasc Med, 2006, pp. S29-S37, vol. 7, Supp. 4.
Leon C, Alex M, Klocke A, et al., Platelet Adp receptors contribute to the initiation of intravascular coagulation, Blood, 2004, pp. 594-600, vol. 103, No. 2.
Mazzucato M, Cozzi MR, Pradella P, et al., Crucial role of the ADP receptor P2Y1 in platelet adhesion and signaling under high flow, Blood, 2002, p. 100, 11.
Michelson AD, P2Y12 Antagonism. Promises and challenges, Arterioscler Thromb Vasc Biol, 2008, pp. S33-S38.
Murugappan S, Kunapuli S, The role of ADP receptors in platelet function, Front Biosci, 2006, pp. 1977-1986, vol. 11.
Nassim MA, Sanderson JB, Clarke C, et al., Investigation of the novel P2T receptor antagonist AR C69931MX on ex vivo adenosine diphosphate induced platelet aggregation and bleeding time in healthy volunteers, JACC, 1999, p. 33, vol. 33 (Supp A).
Niitsu Y, Jakubowski JA, Sugidachi A, et al., Pharmacology of CS-747 (Prasugrel, LY640315), a novel, potent antiplatelet agent with in vivo P2Y12 receptor antagonist activity, Semin Thromb Hemost, 2005, pp. 184-194, vol. 31, No. 2.
Nurden AT, Nurden P, Advantages of fast-acting ADP receptor blockade in ischemic heart disease (Editorial to K. Wang article p. 357), Arterioscler Thromb Vasc Biol, 2003, pp. 158-159.
Nylander S, Mattsson C, Lindahl TL, Characterisation of species differences in the platelet ADP and thrombin response, Thromb Res, 2003, pp. 65-73, vol. 111.
Park SJ, Lee SW, Optimal management of platelet function after coronary stenting, Curr Treat Options Cardiovasc Med, 2007, pp. 37-45.
Parravicini C, Ranghino G, Abbracchio MP, et al., GPR17: Molecular modeling and dynamics studies of the 3-D structure and purinergic ligand binding features in comparison with P2Y receptors, BMC Bioinformatics, 2008, pp. 1-19, vol. 9, No. 263.
Price MJ, New antiplatelet therapies in development, Am J Health-Syst Pharm, 2008, pp. S11-S15, vol. 65.
Raju NC, Eikelboom JW, Hirsh J, Platelet ADP-receptor antagonists for cardiovascular disease: past, present and future, Nat Clin Pract Cardiovasc Med, 2008, pp. 766-780, vol. 5, No. 12.
Rich J, Wiviott SD, New antiplatelet therapies for acute coronary syndromes, Curr Cardiol Rep, 2007, pp. 303-311, vol. 9.
Steinhubl SR, OH JJ, Oestreich JH, et al., Transitioning patients from cangrelor to clopidogrel: Pharmacodynamic evidence of a competitive effect, Thromb Res, 2007, pp. 527-534, vol. 121.
Steinhubl S, Roe MT, Optimizing platelet P2Y12 inhibition for patients undergoing PCI, Cardiovasc Drug Rev, 2007, pp. 188-203, vol. 25, No. 2.
Storey RF, Oldroyd KG, Wilcox RG, First clinical study of the novel platelet ADP receptor (P2T) antagonist AR-C69931MX, assessing safety, tolerability and activity in patients with acute coronary syndromes, Circulation, 1999, p. 1-170 vol. 100, No. 18.
Storey RF, Sanderson HM, White AE, et al., the central role of the P(2T) receptor in amplification of human platelet activation, aggregation, secretion and procoagulant activity, Br J Haematol, 2000, pp. 925-934, vol. 110.
Storey RF, Cameron KE, Pascoe JS, et al., Potential therapeutic effect of the novel platelet adenosine diphosphate receptor (P2T) antagonist, AR C69931MX, as assessed by in vitro studies in human whole blood. A possible adjunct to aspirin therapy?, Eur Heart J, 1998, p. 493, 19(Supp):54.
Storey RF, Variability of response to antiplatelet therapy, Eur Heart J, 2008, pp. A21-A27, 10(SUPP A).
Storey RF, New developments in antiplatelet therapy, Eur Heart J, 2008, pp. D30-D37,10 (SUPP D).
Storey RF, Clinical experience with antithrombotic drugs acting on purine receptor pathways, Drug Dev Res, 2001, pp. 202-212, vol. 52.
Storey RF, The P2Y12 receptor as a therapeutic target in cardiovascular disease, Platelets, 2001, pp. 197-209, vol. 12.
Storey RF, Wilcox RG, Heptinstall S, Comparison of the pharmacodynamic effects of the platelet ADP receptor antagonists clopidogrel and AR-C69931MX in patients with ischaemic heart disease, Platelets, 2002, pp. 407-413, vol. 13.
Harrington RA, Stone GW, McNulty S, et al., Platelet inhibition with cangrelor in patients.undergoing PCI, N Engl J Med, 2009, pp. 2318-2319, vol. 361.

(56) References Cited

OTHER PUBLICATIONS

Iyu D, Glenn Jr, White AE, et al., Adenosine derived from ADP can contribute to inhibition of platelet aggregation in the presence of a P2Y12 antagonist, Arterioscler Thromb Vase Biol, 2011, pp. 416-422, vol. 31.

Leonardi S, Mahaffey KW, White HD, et al., Rationale and design of the cangrelor versus standard therapy to acHieve optimal management of platelet inhibitiON Phoenix trial, Am Heart J, 2012, pp. 768-776.e2, vol. 163.

Leonardi S, Koehler ML, Truffa A, et al., A novel approach to implement the universal definition of myocardial infarction in patients undergoing very early invasive management: insights from the CHAMPION Platform trial, AHA Orlando, FL, Nov. 12-16, 2011.

Leonardi S, Truffa AA, Neely LM, et al., A novel approach to systematically implement the universal definition of myocardial infarctionL insights from the CHAMPION Platform trial, Heart, 2013, pp. 1282-1287, vol. 99.

Testa L, Biondi Zoccai GG, Valgimigli M, et al., Current concepts on antiplatelet therapy: focus on the novel thienopyridine and non-thienopyridine agents, Adv.

White HD, Chew DP, Dauerman HL, et al., Reduced immediate ischemic events with cangrelor in PCI: A pooled analysis of the CHAMPION trials using the universal definitionof myocardial infarction, Am Heart J, 2012, pp. 182-190.e4, vol. 163.

\* cited by examiner

METHODS OF TREATING, REDUCING THE INCIDENCE OF, AND/OR PREVENTING ISCHEMIC EVENTS

CROSS REFERENCE TO RELATED APPLICATIONS

This application is a continuation-in-part of U.S. application Ser. No. 13/792,056 filed on Mar. 9, 2013, which is a continuation-in-part of U.S. application Ser. No. 12/943,717 filed on Nov. 10, 2010, which claims priority to U.S. provisional application Ser. No. 61/260,361 filed on Nov. 11, 2009. This application also claims priority to U.S. provisional application Ser. No. 61/815,735 filed on Apr. 25, 2013. Each of these applications is incorporated herein by reference.

FIELD OF THE INVENTION

The present invention relates to methods of treating, reducing the incidence of, and/or preventing an ischemic event in a patient undergoing percutaneous coronary intervention (PCI), comprising administering to the patient a pharmaceutical composition comprising cangrelor. The methods may further comprise administering an additional therapeutic agent to the patient, such as a different $P2Y_{12}$ inhibitor. The present invention also relates to pharmaceutical compositions useful for treating, reducing the incidence of, and/or preventing an ischemic event in a patient undergoing PCI. The pharmaceutical compositions comprise cangrelor. The present invention further relates to methods of preparing a pharmaceutical composition for treating, reducing the incidence of, and/or preventing an ischemic event in a patient undergoing PCI, comprising admixing cangrelor with one or more pharmaceutically acceptable excipients. An ischemic event may include stent thrombosis, myocardial infarction, ischemia-driven revascularization (IDR), and mortality.

BACKGROUND OF THE INVENTION

PCI is a procedure that opens narrowed arteries that supply heart muscle with blood. PCI with stent implantation is widely used to reduce the risk of mortality or myocardial infarction in patients with acute coronary syndrome and to reduce the burden of angina and improve the quality of life in patients with stable angina.[1] However, thrombotic complications during and after PCI are a major concern, particularly if the procedure involves implantation of a stent, which can induce platelet adhesion, activation and thrombus formation on or near the stent.[2] Thus, antiplatelet therapies are an important adjunct to PCI.[3]

[1] Mehta S R, et al., JAMA 2005; 293:2908-17; De Bruyne B, et al., N Engl J Med 2012; 367:991-1001 [Erratum, N Engl J Med 2012; 367:1768.]; Bhatt D L, JAMA 2005; 293:2935-7; Bavry A A, et al., J Am Coll Cardiol 2006; 48:1319-25; and Bhatt D L, et al., JAMA 2004; 292:2096-104.
[2] Windecker S, et al., Circulation 2007; 116:1952-65; Maisel W H, N Engl J Med 2007; 356:981-4.
[3] Grüntzig A R, et al., N Engl J Med 1979; 301:61-8.

Inhibition of platelet adenosine diphosphate (ADP) receptor $P2Y_{12}$ through pharmacotherapy has been demonstrated to improve cardiovascular outcomes in patients undergoing PCI.[4] Such antiplatelet therapies reduce the risk of ischemic events, particularly stent thrombosis.[5] Yet, there are several limitations regarding the use of orally administered $P2Y_{12}$-receptor inhibitors. For instance, there is a delayed onset of action when these drugs are administered, even when given with a loading dose,[6] which is particularly problematic for patients who require urgent or periprocedural treatment. In addition, patients in the acute phase of cardiovascular illness may have conditions such as nausea, impaired absorption, or impaired perfusion that can limit drug bioavailability; in such patients the antiplatelet effect of oral antiplatelet agents such as clopidogrel may not be sufficient.[7] Further, multiple studies have now demonstrated that the pharmacokinetic and pharmacodynamic effects of clopidogrel, which is a widely-used $P2Y_{12}$ inhibitor, are highly variable[8] and may be influenced by genetic polymorphisms,[9] which translate into differential pharmacodynamic and therapeutic responses that lead to the notion of clopidogrel "low/non-responders."[10] Moreover, many physicians refrain from administering clopidogrel prior to angiographic definition of coronary anatomy, as this irreversible platelet inhibitor has been associated with an increased risk of perioperative bleeding if coronary artery bypass surgery is required rather than percutaneous revascularization.

More potent oral ADP blockers have been tested and found to reduce ischemic outcomes even further, but with increased rates of bleeding.[11]

[4] Yusuf S, et al., N. Eng J Med 2001; 345:494-502; Mehta S R, et al., Lancet 2001; 358:527-33; Sabatine M S, et al., N Engl J Med 2005; 352:1179-89; and Steinhubl S R, et al., JAMA 2002; 288:2411-20 [Erratum, JAMA 2003; 289: 987.].
[5] Yousuf O, et al., Nat Rev Cardiol 2011; 8:547-59; Wiviott S D, et al., N Engl J Med 2007; 357:2001-15; Wallentin et al., N Engl J Med 2009; 361:1045-57; and Bhatt D L, N Engl J Med 2007; 357:2078-81.
[6] Meadows T A, et al., Circ Res 2007; 100:1261-75.
[7] Součhová L, et al., Eur J Clin Pharmacol 2013; 69:309-17 and Heestermans A A, et al., Thromb Res 2008; 122:776-81.
[8] Gurbel P A, et al., J Am Coll Cardiol 2005; 45:1392-6 and Collet J P, et al., Lancet 2009; 373:309-17.
[9] Mega J L, et al., N Engl J Med 2009; 360:354-62.
[10] Gurbel P A, et al., Nature Clin Pract Cardiovasc Med 2006; 3:387-95.
[11] Wiviott S D, et al., N Engl J Med 2007; 357:2001-15; Bhatt DL, N Engl J Med 2007; 357:2078-81; Bhatt D L, N Engl J Med 2009; 361:940-2; Wallentin L, et al., N Engl J Med 2009; 361:1045-57; and Schomig A, et al., N Engl J Med 2009; 361:1108-11.

Thus, despite advances in adjunctive pharmacotherapy, the concern of ischemic events in a patient undergoing PCI has not been eliminated.[12] Accordingly, there is a continuing need for a potent, fast-acting, reversible antiplatelet agent that effectively treats, reduces the incidence of, and/or prevents ischemic events without an excessive risk of bleeding.

[12] Stone G W, et al., N Engl J Med 2009; 360:1946-59 and Bavry A A, et al., Lancet 2008; 371:2134-33.

SUMMARY OF THE INVENTION

The present invention demonstrates how cangrelor may be utilized in treating, reducing the incidence of, and/or preventing an ischemic event. An ischemic event may include stent thrombosis, myocardial infarction, IDR, and mortality. An ischemic event can occur before, during, or after PCI.

An aspect of the present invention is directed to a method of treating, reducing the incidence of, and/or preventing an ischemic event in a patient undergoing PCI. The method comprises administering to the patient a pharmaceutical composition comprising cangrelor. The pharmaceutical composition may be administered before, during, and/or after PCI, and through various routes of administration. For example, the pharmaceutical composition may be administered intravenously, including as a bolus and/or infusion. In addition, the pharmaceutical composition may be administered to a patient undergoing PCI involving stent implantation. The method of the present invention may treat, reduce the incidence of, and/or prevent an ischemic event during or after PCI. In some instances, the method is not accompanied by a significant increase in severe bleeding or the need for transfusions.

In certain embodiments of the invention, the method may further comprise administering an additional therapeutic agent to the patient. The additional therapeutic agent may be administered separately from the pharmaceutical composition comprising cangrelor, either sequentially or concurrently. Alternatively, the additional therapeutic agent may be administered in the same pharmaceutical composition as cangrelor. In some embodiments, the additional therapeutic agent comprises a $P2Y_{12}$ inhibitor, such as clopidogrel, prasugrel, or ticagrelor. In alternative embodiments, the additional therapeutic agent comprises bivalirudin or heparin.

An aspect of the invention is directed to a method of transitioning a patient undergoing PCI from administration of cangrelor during PCI to administration of a chronic or maintenance treatment of a $P2Y_{12}$ inhibitor, such as an oral $P2Y_{12}$-receptor inhibitor, e.g., ticagrelor. The method may comprise (1) administering an intravenous infusion of a pharmaceutical composition comprising cangrelor that is initiated prior to PCI, wherein the intravenous infusion comprises a 30 µg/kg bolus of cangrelor followed by a 4 µg/kg/min continuous infusion of cangrelor, and wherein the continuous infusion of cangrelor continues for the longer of (a) at least two hours, or (b) the duration of PCI; and (2) administering an oral dose of a pharmaceutical composition comprising ticagrelor during the continuous infusion of cangrelor, wherein the oral dose comprises a 180 mg loading dose of ticagrelor. The pharmaceutical composition comprising ticagrelor may be administered during the administration of the intravenous infusion of cangrelor. For instance, the pharmaceutical composition comprising ticagrelor may be administered within 1.25 hours, or within 0.5 hours, of the initiation of the intravenous infusion of cangrelor. The method may further comprise administering one or more oral doses of the pharmaceutical composition comprising ticagrelor subsequent to the loading dose. The one or more subsequent oral doses may comprise 90 mg of ticagrelor, and may continue after the intravenous infusion of cangrelor.

In some embodiments, the method of transitioning a patient undergoing PCI from administration of cangrelor during PCI to administration of a chronic or maintenance treatment of a $P2Y_{12}$ inhibitor, such as an oral $P2Y_{12}$-receptor inhibitor, e.g., ticagrelor, may comprise (1) administering an intravenous infusion of a pharmaceutical composition comprising cangrelor that is initiated prior to PCI, wherein the intravenous infusion comprises a 30 µg/kg bolus of cangrelor followed by a 4 µg/kg/min continuous infusion of cangrelor, and wherein the continuous infusion of cangrelor continues for the longer of (a) at least two hours, or (b) the duration of PCI; and (2) administering an oral dose of a pharmaceutical composition comprising ticagrelor after the continuous infusion of cangrelor, wherein the oral dose comprises a 180 mg loading dose of ticagrelor. The method may further comprise administering one or more oral doses of the pharmaceutical composition comprising ticagrelor subsequent to the loading dose. The one or more subsequent oral doses may comprise 90 mg of ticagrelor.

Another aspect of the present invention is directed to a pharmaceutical composition useful for treating, reducing the incidence of, and/or preventing an ischemic event in a patient undergoing PCI. The pharmaceutical composition comprises cangrelor and may further comprise one or more pharmaceutically acceptable excipients. In addition, the pharmaceutical composition may be a solid, liquid, or suspension. The pharmaceutical composition of the present invention may be useful for treating, reducing the incidence of, and/or preventing an ischemic event that occurs during or after PCI. In some instances, the pharmaceutical composition does not lead to a significant increase in severe bleeding or the need for transfusions when administered to a patient undergoing PCI.

A further aspect of the present invention is directed to a method of preparing a pharmaceutical composition for treating, reducing the incidence of, and/or preventing an ischemic event in a patient undergoing PCI, comprising admixing cangrelor with a pharmaceutically acceptable excipient. The pharmaceutically acceptable excipient may comprise NaCl, dextrose, mannitol, or a combination thereof.

Aspects of the present invention relate to a method of transitioning a patient from administration of cangrelor during PCI to administration of cangrelor in preparation for surgery, or a method of maintaining reduced platelet activity in a patient who is transitioning from administration of cangrelor during PCI to administration of cangrelor in preparation for surgery, or a method of maintaining $P2Y_{12}$ inhibition in a patient who is transitioning from administration of cangrelor during PCI to administration of cangrelor in preparation for surgery. These methods may comprise (1) administering a PCI dosing regimen, wherein the PCI dosing regimen comprises administering intravenously a 30 µg/kg bolus of cangrelor before the start of PCI, and administering intravenously a continuous infusion of cangrelor at an infusion rate of 4 µg/kg/min after administration of the bolus; (2) discontinuing the administration of the PCI dosing regimen; and (3) administering a bridge dosing regimen, wherein the bridge dosing regimen comprises administering intravenously a continuous infusion of cangrelor at an infusion rate of 0.75 µg/kg/min.

Aspects of the present invention further relate to a method of transitioning a patient from administration of cangrelor in preparation for surgery to administration of cangrelor during PCI, or a method of maintaining reduced platelet activity in a patient who is transitioning from administration of cangrelor in preparation for surgery to administration of cangrelor during PCI, or a method of maintaining $P2Y_{12}$ inhibition in a patient who is transitioning from administration of cangrelor in preparation for surgery to administration of cangrelor during PCI. These methods may comprise (1) administering a bridge dosing regimen, wherein the bridge dosing regimen comprises administering intravenously a continuous infusion of cangrelor at an infusion rate of 0.75 µg/kg/min; (2) discontinuing the administration of the bridge dosing regimen; and (3) administering a PCI dosing regimen, wherein the PCI dosing regimen comprises administering intravenously a 30 µg/kg bolus of cangrelor before the start of PCI, and administering intravenously a continuous infusion of cangrelor at an infusion rate of 4 µg/kg/min. In another embodiment, the method may comprise (1) administering a bridge dosing regimen, wherein the bridge dosing regimen comprises administering intravenously a continuous infusion of cangrelor at an infusion rate of 0.75 µg/kg/min; (2) discontinuing the administration of the bridge dosing regimen; and (3) administering a PCI dosing regimen, wherein the PCI dosing regimen comprises administering intravenously a continuous infusion of cangrelor at an infusion rate of 4 µg/kg/min.

BRIEF DESCRIPTION OF THE FIGURES

The following Detailed Description, given by way of example, but not intended to limit the invention solely to the specific embodiments described, may best be understood in conjunction with the accompanying drawings, in which.

DETAILED DESCRIPTION OF THE INVENTION

Figure 1:
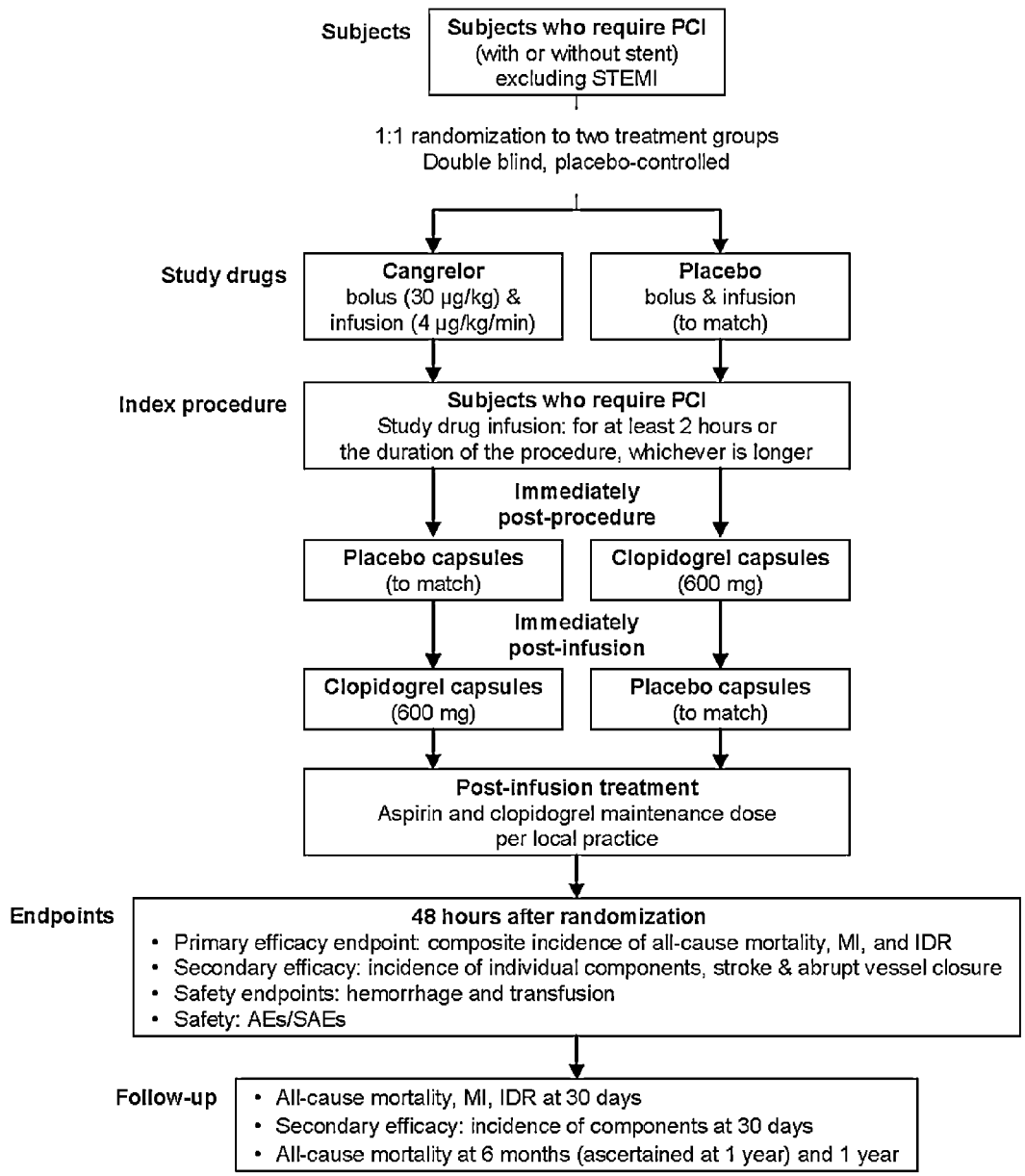
FIG. 1 shows a diagram of the trial design for the study described in Example 1.

The present invention is based on the discovery that cangrelor, a reversible, fast acting, adenosine triphosphate analogue inhibitor of the $P2Y_{12}$ ADP receptor, is effective in treating, reducing the incidence of, and/or preventing an ischemic event. Thus, the present invention is directed to a method of treating, reducing the incidence of, and/or preventing an ischemic event in a patient undergoing PCI, comprising administering to the patient a pharmaceutical composition comprising cangrelor. The present invention is also directed to a pharmaceutical composition useful for treating, reducing the incidence of, and/or preventing an ischemic event in a patient undergoing PCI, wherein the pharmaceutical composition comprises cangrelor and may further comprise one or more pharmaceutically acceptable excipients. Further, the present invention is directed to a method of preparing a pharmaceutical composition for treating, reducing the incidence of, and/or preventing an ischemic event in a patient undergoing PCI, comprising admixing cangrelor with one or more pharmaceutically acceptable excipients.

Canuelor

Cangrelor is a non-thienopyridine adenosine triphosphate analogue which reversibly binds to and inhibits the $P2Y_{12}$ ADP receptor. Cangrelor is direct-acting, reversible, and selective, and it has a short half-life. It is metabolized through dephosphorylation pathways and has a plasma half-life of 3-5 minutes; platelet function returns to normal within 30-60 minutes of drug termination.[13] When given as a bolus plus infusion, it quickly and consistently inhibits platelets to a high degree with normalization of platelet function shortly after discontinuation. A phase 2 trial in patients undergoing PCI demonstrated dose-dependent platelet inhibition similar to that achieved with abciximab, less bleeding time prolongation, and more rapid return to platelet function.[14] The chemical structure of cangrelor is shown in Formula I.

[13] Storey R F, et al., Br J Haematol 2000; 110:925-34.
[14] Greenbaum A B, et al., Am Heart J 2006; 151:689.e1-10.

Formula I

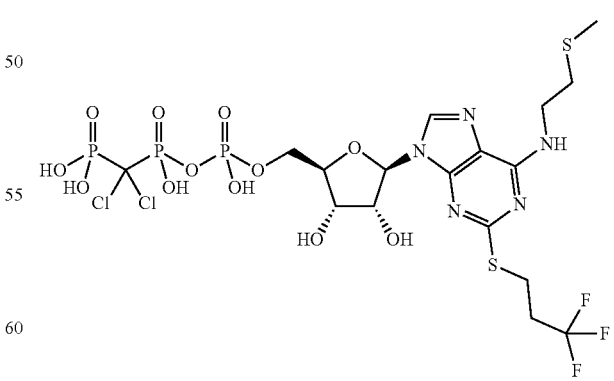

In each of the embodiments of the present invention, the term "cangrelor" encompasses the compound of Formula I, as well as tautomeric, enantiomeric and diastereomeric forms thereof, and racemic mixtures thereof, and pharmaceutically acceptable salts of these compounds, including a tetrasodium salt. These alternative forms and salts, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication No. 2006/0270607.

Ischemic Events

The present invention demonstrates how cangrelor may be utilized in treating, reducing the incidence of, and/or preventing an ischemic event. An ischemic event may include stent thrombosis, myocardial infarction, IDR, and mortality. An ischemic event can occur before, during, or after PCI.

Stent Thrombosis

In certain embodiments, the present invention relates to treating, reducing the incidence of, and/or preventing stent thrombosis in a patient undergoing PCI. Stent thrombosis may result from any means related to the implantation, presence, or maintenance of the stent in the vasculature of the patient. For example, stent thrombosis may be induced by implantation of a stent into the patient or may develop over time due to the presence of a stent, such as a bare-metal stent, a drug-eluting stent, or other type of stent. In some embodiments, stent thrombosis is defined in accordance with or derived from the Academic Research Consortium definition of stent thrombosis.[15] In certain embodiments of the present invention, stent thrombosis may be intraprocedural stent thrombosis, acute stent thrombosis (<24 hours post implantation), sub-acute stent thrombosis (>24 hours and <30 days post implantation), late stent thrombosis (>30 days and <12 months post implantation) or very late stent thrombosis (>12 months post implantation).

[15] Cutlip D E, et al., Circulation 2007; 115(17):2344-51.

Myocardial Infarction

In certain embodiments, the present invention relates to treating, reducing the incidence of, and/or preventing myocardial infarction in a patient undergoing PCI. Myocardial infarction may be acute non-ST-elevated myocardial infarction (NSTEMI), or acute ST-elevated myocardial infarction (STEMI). In some embodiments, myocardial infarction is defined in accordance with or derived from the universal definition of myocardial infarction.[16]

[16] Thygesen K, et al., Eur Heart J 2007; 28:2525-38.

Myocardial infarction may arise during PCI, or may be induced by any mechanism, including implantation of a stent into the patient. Myocardial infarction may also be caused by stent thrombosis or occlusion of a coronary artery.

Ischemia-Driven Revascularization (IDR)

In certain embodiments, the present invention relates to treating, reducing the incidence of, and/or preventing IDR in a patient undergoing PCI. IDR refers to any type of intervention following PCI in which blood flow through a vessel must be increased or re-established. Examples of IDR include, but are not limited to, an additional PCI or surgery.

Mortality

In certain embodiments, the present invention relates to reducing the incidence of and/or preventing mortality in a patient undergoing PCI. In some embodiments, mortality may be associated with other ischemic events. For instance, mortality may be caused by stent thrombosis, occlusion of a coronary artery, and/or myocardial infarction.

Methods of Treating, Reducing the Incidence of, and/or Preventing an Ischemic Event An aspect of the present invention is methods of treating, reducing the incidence of, and/or preventing an ischemic event in a patient undergoing PCI, comprising administering to the patient a pharmaceutical composition comprising cangrelor.

PCI may comprise, without limitation, balloon angioplasty, stent implantation, rotational or laser atherectomy, and/or brachytherapy. In instances in which a stent is implanted, the stent may be, without limitation, a bare-metal stent, a drug-eluting stent, an absorbable stent, etc., as known in the art.

Timing, Duration, and Routes of Administration of the Pharmaceutical Composition A method of the present invention comprises administering the pharmaceutical composition before, during, and/or after PCI. The administration may continue for a short period of time, such as less than about an hour, or may be one or more hours. In some embodiments, the administration may continue for at least the duration of the PCI. In other embodiments, the administration may continue after the PCI has concluded. In certain embodiments, the administration may continue for at least about two hours or the duration of the PCI procedure, whichever is longer. In an additional embodiment, the administration may continue for up to about four hours, or for about four hours, or longer.

A method may comprise administering the pharmaceutical composition multiple times before, during, and/or after PCI. For example, administration of the pharmaceutical composition may be for a short period of time before the PCI, and then again once PCI has begun.

In certain embodiments, the method may comprise administering the pharmaceutical composition periodically after the PCI has concluded. For instance, the pharmaceutical composition may be administered once, twice, thrice or more times a day, once every two days, once every three days, etc., and for weeks, months, or even years, after the PCI, particularly if the PCI involved stent implantation.

In additional embodiments, the method may comprise administering the pharmaceutical composition once the ischemic event is recognized or diagnosed, or at the onset of symptoms of the ischemic event. For example, the pharmaceutical composition may be administered if symptoms of a myocardial infarction are observed. The pharmaceutical composition may be administered within a short period of time from the onset of symptoms of the ischemic event. The short period of time may range from about one or two minutes to about one or two hours.

In some embodiments, the method may comprise administering the pharmaceutical composition as a prophylaxis against an ischemic event, such as myocardial infarction. Patients appropriate for such prevention include any patient suspected of having early symptoms of the ischemic event, or a condition that could lead to the ischemic event against which the pharmaceutical compositions of the invention would be effective. The pharmaceutical composition may be administered to the patient within a short period of time of when early or initial symptoms of the ischemic event are detected.

The present invention may further comprise administering the pharmaceutical composition concurrently or sequentially (before or after) with at least one additional therapeutic agent. The additional therapeutic agent may be, for example, a $P2Y_{12}$-receptor inhibitor such as an oral $P2Y_{12}$-receptor inhibitor, a glycoprotein IIb/IIIa inhibitor, or aspirin.

Administering a $P2Y_{12}$-receptor inhibitor, such as an oral $P2Y_{12}$-receptor inhibitor, concurrently or sequentially with the pharmaceutical composition can result in (a) a reduction in the incidence of an ischemic event; (b) inhibition of platelet aggregation; (c) inhibition of platelet reactivity; (d) attenuation of an increase in platelet reactivity after administration of the pharmaceutical composition has discontinued; and/or (e) attenuation of an increase in platelet aggregation after administration of the pharmaceutical composition has discontinued.

In addition, administering the $P2Y_{12}$-receptor inhibitor, such as an oral $P2Y_{12}$-receptor inhibitor, either concurrently or sequentially with the pharmaceutical composition in a patient undergoing PCI may also transition the patient to chronic or maintenance treatment with the $P2Y_{12}$-receptor inhibitor.

In the embodiments in which the $P2Y_{12}$-receptor inhibitor is administered concurrently with the administration of the pharmaceutical composition, the $P2Y_{12}$-receptor inhibitor can be administered during the administration of the cangrelor bolus or during the administration of the cangrelor infusion. In certain embodiments, the $P2Y_{12}$-receptor inhibitor is administered within the first hour of the cangrelor infusion, such as 30 minutes (i.e., 0.5 hr) after the beginning of the infusion. In some embodiments, the $P2Y_{12}$-receptor inhibitor is administered within the second hour of the cangrelor infusion, such as 75 minutes (i.e., 1.25 hr) after the beginning of the infusion.

In certain embodiments, the $P2Y_{12}$-receptor inhibitor, such as an oral $P2Y_{12}$-receptor inhibitor, may be administered as a loading dose, followed by one or more subsequent doses. The one or more subsequent doses may comprise a higher, lower, or same amount of the $P2Y_{12}$-receptor inhibitor as the loading dose.

The $P2Y_{12}$-receptor inhibitor may be clopidogrel. In preferred embodiments, the clopidogrel is administered as a 600 mg loading dose immediately following the discontinuation of the administration of the pharmaceutical composition comprising cangrelor.

The $P2Y_{12}$-receptor inhibitor may also be ticagrelor. In preferred embodiments, the ticagrelor is administered as a 180 mg loading dose either during or immediately following the discontinuation of the pharmaceutical composition comprising cangrelor. One or more subsequent doses may be administered after the loading dose. The one or more subsequent doses may comprise about 90 mg of ticagrelor.

Further, the $P2Y_{12}$-receptor inhibitor may be prasugrel. In preferred embodiments, the prasugrel is administered as a 60 mg loading dose immediately following the discontinuation of the pharmaceutical composition comprising cangrelor.

In certain embodiments, an oral $P2Y_{12}$ therapy may be administered prior to the administration of the pharmaceutical composition comprising cangrelor. Such administration may not attenuate the effect of cangrelor. This oral $P2Y_{12}$ therapy may be selected from the group consisting of clopidogrel, ticagrelor, and prasugrel.

The routes of administration of the methods of the present invention include, for example, oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any known device useful for parenteral injection or infusion of drug formulations can be used in the methods of the present invention. In noted aspects and embodiments of the present invention, administration is via parenteral administration, preferably intravenous administration, or oral administration.

When administered intravenously, the pharmaceutical composition comprising cangrelor may be administered as a bolus, as a continuous infusion, or as a bolus followed by a continuous infusion. For example, the pharmaceutical composition may be administered prior to PCI as a bolus, and may be administered during PCI as a continuous infusion.

When the pharmaceutical composition comprising cangrelor is administered as a bolus, it is administered within a short period of time, such as two minutes or less, or one minute or less.

Doses of cangrelor in the pharmaceutical compositions administered in the methods of the present invention may vary depending upon the stated goals of the methods (treating, reducing the incidence of, and/or preventing), the physical characteristics of the patient, the significance of the ischemic event, existence of related or unrelated medical conditions, the composition of the formulation and the means used to administer the drug to the patient. In some embodiments, the dose for a given patient may be set by the judgment of the attending physician.

When administered as a bolus, a dose of about 5 to about 100 µg/kg cangrelor, such as between about 20 and about 40 µg/kg cangrelor, or about 30 µg/kg cangrelor, is administered. When administered as a continuous infusion, cangrelor may be administered at about 0.1 to about 30 µg/kg/min, for example, between about 1 and about 10 µg/kg/min, or about 4 µg/kg/min. In some embodiments, the dose may differ in the periods before PCI, during PCI and after PCI.

In certain embodiments, the method of the present invention comprises administering a bolus of about 30 µg/kg cangrelor, followed by administering an infusion of about 4 µg/kg/min cangrelor.

When the pharmaceutical composition is administered orally, a dose of between about 0.5 to about 100 mg/kg cangrelor or about 5 to about 30 mg/kg cangrelor is administered per day. Oral administration may occur once a day or multiple times per day.

In certain embodiments of the present invention, an additional therapeutic agent is administered in addition to the pharmaceutical composition comprising cangrelor. When the additional therapeutic agent comprises clopidogrel, it may be administered orally with a dose of clopidogrel from about 75 mg to about 600 mg.

Patients

As used herein, a "patient" upon which the methods of the present invention may be practiced refers to an animal, preferably a human. Such patients may have an ischemic event, such as stent thrombosis, myocardial infarction, IDR, or mortality.

In view of the fact that the patients upon which some of the methods of the present invention are being practiced have underlying health conditions that require PCI, one of ordinary skill in the art will understand that the patients may have various additional physical characteristics related to such underlying health conditions. For example, in each of the embodiments of the present invention, the patient may have a condition selected from the group consisting of STEMI, NSTEMI, stable angina, unstable angina, and acute coronary syndrome. The patient may be of any age, gender, or weight. The patient may have received different therapeutic agents, such as a periprocedural glycoprotein IIb/IIIa inhibitor, periprocedural unfractionated heparin (UFH), periprocedural low-molecular-weight heparin (LMWH), periprocedural bivalirudin, or periprocedural clopidogrel.

To further characterize the patients to which the methods of the present invention may be applied, it is noted that the patient may have suffered a stroke, or may have diabetes mellitus, hypertension, hyperlipidemia, a myocardial infarction, or may have a family history of coronary artery disease (CAD). The patient may have undergone percutaneous transluminal coronary angioplasty (PTCA), PCI, or coronary artery bypass graft (CABG). The patient may have congestive heart failure, peripheral arterial disease (PAD), or stent thrombosis in more than one artery or vein. Further, the patient may be on periprocedural medications such as clopidogrel, bivalirudin, unfractionated heparain, low-molecular-weight heparin, fondaparinux, or aspirin.

Results of the Methods

Each of the methods recited in the present invention may include the additional step of measuring the effectiveness of the administration of the pharmaceutical composition comprising cangrelor, including the timing, duration, and route of administration of the pharmaceutical composition. The measurement may include the effectiveness of the administration of any additional therapeutic agent. In one example, this additional step may be performed about 0.5 to about 24 hours after administration is complete. Characteristics that are representative of effectiveness include, for example, an increase in luminal diameter within a stent, a decrease in the size of the stent thrombus, and a decreased incidence of myocardial infarction.

Transition from PCI Dosing Regimen to Bridge Dosing Regimen, and from Bridge Dosing Regimen to PCI Dosing Regimen An aspect of the present invention is a method of transitioning a patient from administration of cangrelor during PCI to administration of cangrelor in preparation for surgery, or a method of transitioning a patient from administration of cangrelor in preparation for surgery to administration of cangrelor during PCI. Another aspect of the invention is a method of maintaining reduced platelet activity in a patient who is transitioning from administration of cangrelor during PCI to administration of cangrelor in preparation for surgery, or who is transitioning from administration of cangrelor in preparation for surgery to administration of cangrelor during PCI. Yet a further aspect of the invention is a method of maintaining $P2Y_{12}$ inhibition in a patient who is transitioning from administration of cangrelor during PCI to administration of cangrelor in preparation for surgery, or who is transitioning from administration of cangrelor in preparation for surgery to administration of cangrelor during PCI.

The reasons why a patient may have to transition from administration of cangrelor during PCI to administration of cangrelor in preparation for surgery, or vice-versa, can vary. For example, as a patient is administered cangrelor during PCI, it may be determined that surgery is necessary due to, for instance, new information that was gathered during PCI or complications that arose from the PCI procedure itself. On the other hand, a patient administered cangrelor during preparation for surgery may have to undergo PCI, such as when it is discovered that the patient is in immediate need of angioplasty or the implantation of a stent. In each of these cases, the patient has to change from one dosing regimen of cangrelor to a different dosing regimen.

Transitioning from administration of cangrelor during PCI to administration of cangrelor in preparation for surgery may be performed by administering a PCI dosing regimen, discontinuing the administration of the PCI dosing regimen, and administering a bridge dosing regimen. Transitioning from administration of cangrelor in preparation for surgery to administration of cangrelor during PCI may be performed by administering a bridge dosing regimen, discontinuing the administration of the bridge dosing regimen, and administering a PCI dosing regimen. A "PCI dosing regimen" refers to the doses of cangrelor that a patient receives when undergoing PCI. A "bridge dosing regimen" refers to the doses of cangrelor that a patient receives in the "bridging" period leading up to surgery, i.e., the period of time between the discontinuation of oral $P2Y_{12}$ inhibitors and surgery.

The PCI dosing regimen comprises administering intravenously a continuous infusion of cangrelor at a rate of about 3 to about 10 µg/kg/min, or about 4 µg/kg/min. The continuous infusion may be accompanied by intravenous administration of a bolus. The bolus may comprise about 10 to about 100 µg/kg cangrelor, such as between about 20 and about 40 µg/kg cangrelor, or about 30 µg/kg cangrelor. The bolus may be administered rapidly, for example, in less than about two minutes, or less than about one minute. Preferably, the administration of the continuous infusion is started immediately after the administration of the bolus.

The bridge dosing regimen comprises administering intravenously a continuous infusion of cangrelor at a rate of about 0.1 to about 2 µg/kg/min, or about 0.75 µg/kg/min.

The cangrelor may be administered in a pharmaceutical composition. The pharmaceutical composition may comprise 200 µg/mL of cangrelor. The pharmaceutical composition may also comprise sodium chloride injection 0.9% USP or 5% dextrose injection, USP.

In embodiments in which the patient is transitioning from administration of cangrelor during PCI to administration of cangrelor in preparation for surgery, the discontinuation of the administration of the PCI dosing regimen may occur at any time during the PCI continuous infusion. The administration of the bridge dosing regimen may occur as quickly as possible following the discontinuation of the administration of the PCI dosing regimen. In some embodiments, the discontinuation of the administration of the PCI dosing regimen and the administration of the bridge dosing regimen may be achieved simultaneously by lowering the PCI continuous infusion rate to the bridge continuous infusion rate. The administration of the bridge dosing regimen may be discontinued at least about one hour prior to administration of anesthesia for the surgery. Moreover, the administration of the bridge dosing regimen may be discontinued after no longer than about 7 days from initiation.

In embodiments in which the patient is transitioning from administration of cangrelor in preparation of surgery to administration of cangrelor during PCI, the discontinuation of the administration of the bridge dosing regimen can occur any time during the bridge continuous infusion. The administration of the PCI dosing regimen may occur as quickly as possible following the discontinuation of the administration of the bridge dosing regimen. In some embodiments, the discontinuation of the administration of the bridge dosing regimen and the administration of the PCI dosing regimen may be achieved simultaneously by increasing the bridge continuous infusion rate to the PCI continuous infusion rate. If the PCI dosing regimen includes the administration of a bolus, then the bolus can be administered immediately before or after the increase to the PCI continuous infusion rate. The administration of the continuous infusion of cangrelor in PCI dosing regimen may continue for the longer of (a) at least two hours, or (b) the duration of PCI. The continuous infusion may be continued for a total duration of about four hours.

Pharmaceutical Compositions Useful for Treating, Reducing the Incidence of, and/or Preventing Ischemic Events An aspect of the present invention is directed to a pharmaceutical composition useful for treating, reducing the incidence of, and/or preventing an ischemic event in a patient undergoing PCI. The pharmaceutical composition comprises cangrelor, and may further comprise one or more pharmaceutically acceptable excipients. The pharmaceutical composition may be administered according to any of the methods of the present invention described above.

Pharmaceutically Acceptable Excipients

These pharmaceutical compositions may comprise one or more pharmaceutically acceptable excipients including, but not limited to, carriers, diluents, stabilizing agents, solubilizing agents, surfactants, buffers, antioxidants, preservatives, tonicity agents, bulking agents, lubricating agents, emulsifiers, suspending or viscosity agents, fillers, disintegrating agents, binding agents, wetting agents, lubricating agents, antibacterials, chelating agents, sweeteners, perfuming agents, flavouring agents, coloring agents, administration aids, and combinations thereof. Particular excipients include, but are not limited to, cornstarch or gelatin, lactose, sucrose, dextrose, microcrystalline cellulose, kaolin, mannitol, sorbitol, dicalcium phosphate, sodium chloride, alginic acid, croscarmellose sodium, sodium starch glycolate, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, cyclodextrin or cyclodextrin derivatives (including HPCD ((2-hydroxypropyl)-cyclodextrin) and (2-hydroxyethyl)-cyclodextrin), hydrophilic and hydrophobic carriers, and combinations thereof. Hydrophobic carriers include, for example, fat emulsions, lipids, PEGylated phospholipids, polymer matrices, biocompatible polymers, liposphere, vesicles, particles, and liposomes. In certain embodiments, the pharmaceutical compositions may comprise polyols, such as sorbitol, lactose, sucrose, inositol or trehalose.

The pharmaceutical compositions of the present invention may be formulated for the route by which they are administered to the patients, which include solids, liquids, and suspensions. For example, if the pharmaceutical composition is formulated for IV administration, the pharmaceutical composition may comprise an intravenous fluid, which includes, but is not limited to, water-for-injection (WFI), physiological saline, 0.9% NaCl, phosphate buffered saline, 5% dextrose in water, and 0.002% polysorbate 80 in water or Ringer's™ solution. Such compositions may comprise cangrelor in an amount of about 200 µg/mL. If the pharmaceutical composition is formulated for intramuscular administration, the pharmaceutical composition may comprise an intravenous fluid, which includes, but is not limited to, WFI, physiological saline, 0.9% NaCl, phosphate buffered saline, and 5% dextrose in water.

If the pharmaceutical composition is formulated for oral administration, the pharmaceutical composition may comprise excipients that include, but are not limited to diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth, methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloidal silica, silicon fluid or talc), disintegrating agents (e.g., potato starch, corn starch and alginic acid), flavouring agents (e.g. peppermint, oil of wintergreen, fruit flavoring, bubblegum, and the like), and coloring agents. Excipients may also include coatings such as glyceryl monostearate or glyceryl distearate, to delay absorption in the gastrointestinal tract. For oral use, the pharmaceutical composition may be made in the form of a tablet, capsule, suspension or liquid syrup or elixir, wafers and the like.

Preparing Pharmaceutical Compositions

The pharmaceutical compositions of the present invention may be prepared by admixing cangrelor with the one or more pharmaceutically acceptable excipients. Methods of admixing and devices useful for admixing are known in the art.

In certain embodiments, cangrelor and the one or more pharmaceutically acceptable excipients are dissolved and then admixed. The resulting mixture may be dried, such as through lyophilization, to form a solid pharmaceutical composition, or the resulting mixture may remain in solution form as a liquid pharmaceutical composition. In some embodiments, the solid pharmaceutical composition may be solubilized in an intravenous fluid before administration, for example, as a bolus or infusion.

In some embodiments, the pharmaceutical composition is prepared by dissolving and admixing cangrelor, mannitol, sorbitol, and optionally sodium hydroxide, and then lyophilizing the mixture. Prior to administration, the lyophilized mixture is dissolved in an intravenous fluid such as WFI or physiological saline.

The present invention will now be further described by way of the following non-limiting examples, which further illustrate the present invention; such examples are not intended, nor should they be interpreted, to limit the scope of the present invention.

EXAMPLES

Example 1

Intravenous Platelet Blockade with Cangrelor Versus Placebo During Percutaneous Coronary Intervention In this example, the efficacy of cangrelor versus placebo was examined when administered to patients during percutaneous coronary intervention (PCI).

Patients were enrolled at 218 sites in 18 countries from October 2006 to May 2009. Patients were randomized in a double-blind, placebo-controlled, double-dummy design to receive either (i) placebo bolus and infusion or (ii) cangrelor 30 µg/kg bolus and 4 µg/kg/min infusion for the duration of PCI, with a minimum infusion duration of 2 hours and a maximum of 4 hours. Patients in the placebo arm of the trial received 600 mg of clopidogrel at the end of the procedure, while patients in the cangrelor arm received 600 mg of clopidogrel after the end of the cangrelor infusion (FIG. 1).

The inclusion criteria for the trial were as follows: age ≥18 years; diagnostic coronary angiography revealing atherosclerotic lesion(s) amenable to PCI with or without stent implantation; and evidence of either non-ST-segment elevation myocardial infarction or unstable angina. Stable angina was initially allowed at the beginning of the trial prior to a protocol amendment. The diagnosis of non-ST-segment elevation myocardial infarction required troponin I or T greater than the upper limit of normal within 24 hours of randomization (or if troponin results were unavailable at that time, creatine kinase-myocardial band isoenzyme [CK-MB] greater than the upper limit of normal). The diagnosis of unstable angina required ischemic chest discomfort occurring at rest and lasting ≥10 minutes within the 24 hours prior to randomization and dynamic electrocardiographic changes; age ≥65 years and/or diabetes mellitus were also required.

The exclusion criteria included the following: prior thienopyridine use in the past 7 days, planned staged PCI procedure where the second stage would occur ≤30 days after the first PCI, admission planned for <12 hours following PCI, ST-segment elevation myocardial infarction within 48 hours of randomization, known or suspected pregnancy, lactating females, increased bleeding risk (ischemic stroke within the last year or any previous hemorrhagic stroke), intracranial tumor, cerebral arteriovenous malformation, intracranial aneurysm, recent (<1 month) trauma or major surgery (including coronary artery bypass grafting), current warfarin use, active bleeding, known International Normalized Ratio>1.5, past or present bleeding disorder, platelet count <100,000 μL, severe hypertension (systolic blood pressure >180 mm Hg or diastolic blood pressure >110 mm Hg), fibrinolytic therapy or glycoprotein IIb/IIIa inhibitor use in the 12 hours preceding randomization.

The primary efficacy endpoint was the composite of mortality, myocardial infarction, or ischemia-driven revascularization at 48 hours. The primary analysis was performed on a modified intent-to-treat population. Confirmatory analyses were performed on an intent-to-treat population. Secondary endpoints included the individual rates of mortality, myocardial infarction, new Q-wave myocardial infarction, ischemia-driven revascularization, abrupt vessel closure, or stroke at 48 hours. Mortality at 30 days and 1 year was also recorded. The clinical events committee adjudicated myocardial infarction, Q-wave myocardial infarction, ischemia-driven revascularization, stent thromboses, and stroke (ischemic or hemorrhagic). The definition of stent thrombosis was similar to the Academic Research Consortium definition of definite stent thrombosis. After review of the prespecified analyses, two exploratory endpoints less reliant on periprocedural biomarker ascertainment were examined. The exploratory endpoints, which were composed of prespecified and adjudicated endpoints, were the composite of mortality, Q-wave myocardial infarction, or ischemia-driven revascularization and the composite of mortality, Q-wave myocardial infarction, or stent thrombosis. Bleeding and adverse events through 48 hours were compared.

Statistical Analyses

All efficacy analyses were performed on the modified intent-to-treat population, defined as all randomized patients who received at least one dose of study drug and underwent the index PCI. All safety-related analyses were performed on the safety population, which included all patients who received at least one dose of assigned study drug. Patients in the safety analyses were assigned to a treatment arm based on treatment actually received, not as randomized. Intent-to-treat analyses are also presented for full disclosure of results. All statistical tests were two-tailed using a level of significance of 0.05. The primary endpoint comparison between the cangrelor and placebo arms was performed by calculating an odds ratio (OR) with accompanying 95% confidence intervals (CI) using logistic regression. Logistic regression was also used to analyze the majority of the remaining secondary endpoints. The trial had 85% power to detect a 25% reduction in the primary endpoint, assuming a 7.7% event rate in the placebo arm, with a projected sample size of 6400 patients.

Figure 2:
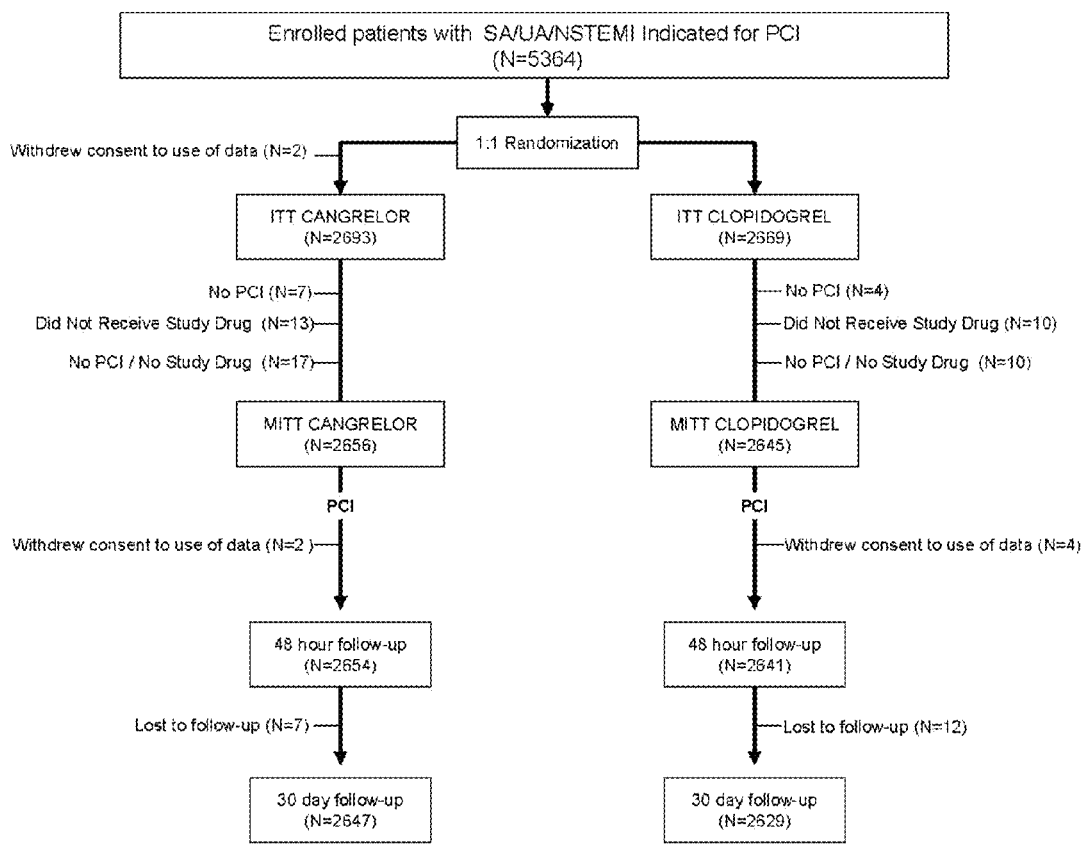
FIG. 2 shows a diagram of the primary modified intent-to-treat analysis population in the study described in Example 1.

A total of 5362 patients were included in the intent-to-treat population; of these, 5301 formed the primary modified intent-to-treat analysis population (FIG. 2). There were 61 patients who were not included because they did not receive study drug or undergo PCI. Baseline characteristics were well-matched in the two groups (Table 1).

TABLE 1

Baseline characteristics for ITT, MITT, and Safety populations.

| | ITT | | MITT | | Safety | |
|---|---|---|---|---|---|---|
| | Cangrelor (N = 2693) | Clopidogrel (N = 2669) | Cangrelor (N = 2656) | Clopidogrel (N = 2645) | Cangrelor (N = 2662) | Clopidogrel (N = 2650) |
| Age, yrs | 63.0 (54.0, 71.0) | 63.0 (54.0, 71.0) | 63.0 (54.0, 71.0) | 63.0 (54.0, 71.0) | 63.0 (54.0, 71.0) | 63.0 (54.0, 71.0) |
| Sex, No. (%) | | | | | | |
| Male | 1938 (72.0) | 1877 (70.3) | 1909 (71.9) | 1863 (70.4) | 1915 (71.9) | 1866 (70.4) |
| Female | 755 (28.0) | 792 (29.7) | 747 (28.1) | 782 (29.6) | 747 (28.1) | 784 (29.6) |
| Race, No. (%) | | | | | | |
| White | 2039 (76.0) | 2024 (76.0) | 2015 (76.1) | 2006 (76.0) | 2017 (76.0) | 2009 (76.0) |
| Asian | 482 (18.0) | 476 (17.9) | 475 (17.9) | 473 (17.9) | 477 (18.0) | 474 (17.9) |
| Black | 80 (3.0) | 73 (2.7) | 75 (2.8) | 72 (2.7) | 76 (2.9) | 73 (2.8) |
| Hispanic | 75 (2.8) | 85 (3.2) | 74 (2.8) | 84 (3.2) | 75 (2.8) | 84 (3.2) |
| Other | 8 (0.3) | 5 (0.2) | 8 (0.3) | 5 (0.2) | 8 (0.3) | 5 (0.2) |
| Weight, kg | 80.0 (70.0, 92.0) | 80.0 (70.0, 92.0) | 80.0 (70.0, 92.0) | 80.0 (70.0, 92.0) | 80.0 (70.0, 92.0) | 80.0 (70.0, 92.0) |
| Height, cm | 170.0 (163.0, 176.0) | 170.0 (163.0, 176.0) | 170.0 (163.0, 176.0) | 170.0 (163.0, 176.0) | 170.0 (163.0, 176.0) | 170.0 (163.0, 176.0) |
| Stable angina, No. (%) | 145 (5.4) | 142 (5.3) | 139 (5.2) | 140 (5.3) | 138 (5.2) | 141 (5.3) |
| Unstable angina, No. (%) | 949 (35.2) | 918 (34.4) | 939 (35.4) | 909 (34.4) | 940 (35.3) | 911 (34.4) |
| NSTEMI, No. (%) | 1599 (59.4) | 1609 (60.3) | 1578 (59.4) | 1596 (60.3) | 1584 (59.5) | 1598 (60.3) |
| Medical history, No. (%) | | | | | | |
| Diabetes mellitus | 828 (30.8) | 868 (32.6) | 812 (30.6) | 862 (32.6) | 815 (30.6) | 862 (32.6) |
| Current smoker | 850 (31.8) | 806 (30.4) | 842 (31.9) | 799 (30.4) | 845 (31.9) | 799 (30.3) |
| Hypertension | 1994 (74.3) | 1979 (74.5) | 1972 (74.5) | 1962 (74.5) | 1974 (74.4) | 1966 (74.5) |
| Hyperlipidemia | 1342 (53.5) | 1347 (54.0) | 1324 (53.6) | 1332 (53.9) | 1325 (53.5) | 1335 (53.9) |
| Stroke/TIA | 162 (6.0) | 160 (6.0) | 159 (6.0) | 158 (6.0) | 160 (6.0) | 158 (6.0) |
| Family history of CAD | 918 (36.4) | 901 (36.0) | 902 (36.2) | 890 (35.9) | 907 (36.4) | 891 (35.9) |

TABLE 1-continued

Baseline characteristics for ITT, MITT, and Safety populations.

|  | ITT | | MITT | | Safety | |
|---|---|---|---|---|---|---|
|  | Cangrelor (N = 2693) | Clopidogrel (N = 2669) | Cangrelor (N = 2656) | Clopidogrel (N = 2645) | Cangrelor (N = 2662) | Clopidogrel (N = 2650) |
| MI | 645 (24.1) | 683 (25.7) | 640 (24.2) | 679 (25.8) | 641 (24.2) | 680 (25.7) |
| PTCA/PCI | 381 (14.2) | 411 (15.5) | 374 (14.1) | 409 (15.5) | 377 (14.2) | 409 (15.5) |
| CABG | 203 (7.5) | 223 (8.4) | 199 (7.5) | 221 (8.4) | 200 (7.5) | 221 (8.3) |
| Congestive HF | 210 (7.8) | 192 (7.2) | 206 (7.8) | 191 (7.2) | 208 (7.8) | 191 (7.2) |
| PAD | 126 (4.8) | 143 (5.5) | 122 (4.7) | 142 (5.5) | 124 (4.8) | 142 (5.5) |
| Periprocedural medications, No (%) | | | | | | |
| Bivalirudin | 565 (21.0) | 561 (21.0) | 559 (21.0) | 555 (21.0) | 561 (21.1) | 556 (21.0) |
| UFH | 1714 (63.7) | 1709 (64.1) | 1699 (64.0) | 1695 (64.1) | 1701 (63.9) | 1699 (64.1) |
| LMWH | 487 (18.1) | 501 (18.8) | 481 (18.1) | 497 (18.8) | 484 (18.2) | 497 (18.8) |
| GP IIb/IIIa | 245 (9.1) | 247 (9.3) | 241 (9.1) | 244 (9.2) | 242 (9.1) | 244 (9.2) |
| Study treatment Number of target vessels, No. (%) | | | | | | |
| 1 | 2231 (83.7) | 2211 (83.3) | 2218 (83.6) | 2201 (83.3) | 2217 (83.6) | 2202 (83.3) |
| 2 | 414 (15.5) | 412 (15.5) | 414 (15.6) | 412 (15.6) | 414 (15.6) | 412 (15.6) |
| 3 | 19 (0.7) | 29 (1.1) | 19 (0.7) | 29 (1.1) | 19 (0.7) | 29 (1.1) |
| Drug-eluting stent, No. (%) | 1037 (38.9) | 1023 (38.6) | 1033 (38.9) | 1021 (38.6) | 1032 (38.9) | 1022 (38.7) |
| Non-drug-eluting stent, No. (%) | 1514 (56.8) | 1515 (57.1) | 1509 (56.9) | 1510 (57.1) | 1509 (56.9) | 1510 (57.1) |
| Angiographic complications (site reported) | | | | | | |
| Threatened abrupt closure | 10 (0.4) | 9 (0.3) | 10 (0.4) | 9 (0.3) | 10 (0.4) | 9 (0.3) |
| Unsuccessful procedure | 84 (3.1) | 97 (3.7) | 81 (3.1) | 95 (3.6) | 81 (3.1) | 95 (3.6) |
| Abrupt vessel closure | 13 (0.5) | 16 (0.6) | 13 (0.5) | 16 (0.6) | 13 (0.5) | 16 (0.6) |
| New thrombus or suspected thrombus | 14 (0.5) | 15 (0.6) | 14 (0.5) | 15 (0.6) | 14 (0.5) | 15 (0.6) |
| Acute stent thrombosis | 1 (0.0) | 5 (0.2) | 1 (0.0) | 5 (0.2) | 1 (0.0) | 5 (0.2) |
| Need for urgent CABG | 5 (0.2) | 4 (0.2) | 5 (0.2) | 3 (0.1) | 5 (0.2) | 3 (0.1) |
| IV study drug administered, No. (%) | 2663 (98.9) | 2649 (99.3) | 2656 (100.0) | 2645 (100.0) | 2662 (100.0) | 2650 (100.0) |
| Bolus administered, No. (%) | 2663 (98.9) | 2649 (99.3) | 2656 (100.0) | 2645 (100.0) | 2662 (100.0) | 2650 (100.0) |
| Infusion administered, No. (%) | 2659 (98.7) | 2649 (99.3) | 2654 (99.9) | 2645 (100.0) | 2658 (99.8) | 2650 (100.0) |
| Duration of infusion, hrs | 2.1 (2.0, 2.3) | 2.1 (2.0, 2.3) | 2.1 (2.0, 2.3) | 2.1 (2.0, 2.3) | 2.1 (2.0, 2.3) | 2.1 (2.0, 2.3) |
| Oral study drug administered, No. (%) | 2630 (97.7) | 2626 (98.4) | 2629 (99.0) | 2625 (99.2) | 2629 (98.8) | 2627 (99.1) |

Variables are presented as median (25th, 75th) unless otherwise indicated. CABG denotes coronary artery bypass grafting; CAD, coronary artery disease; GP, glycoprotein; HF, heart failure; ITT, intent to treat; IV, intravenous; LMWH, low molecular weight heparin; MI, myocardial infarction; MITT, modified intent to treat; NSTEMI, non-ST-segment elevation myocardial infarction; PAD, peripheral artery disease; PCI, percutaneous coronary intervention; PTCA, percutaneous transluminal coronary angioplasty; TIA, transient ischemic attack; UFH, unfractionated heparin.

Figure 3A:
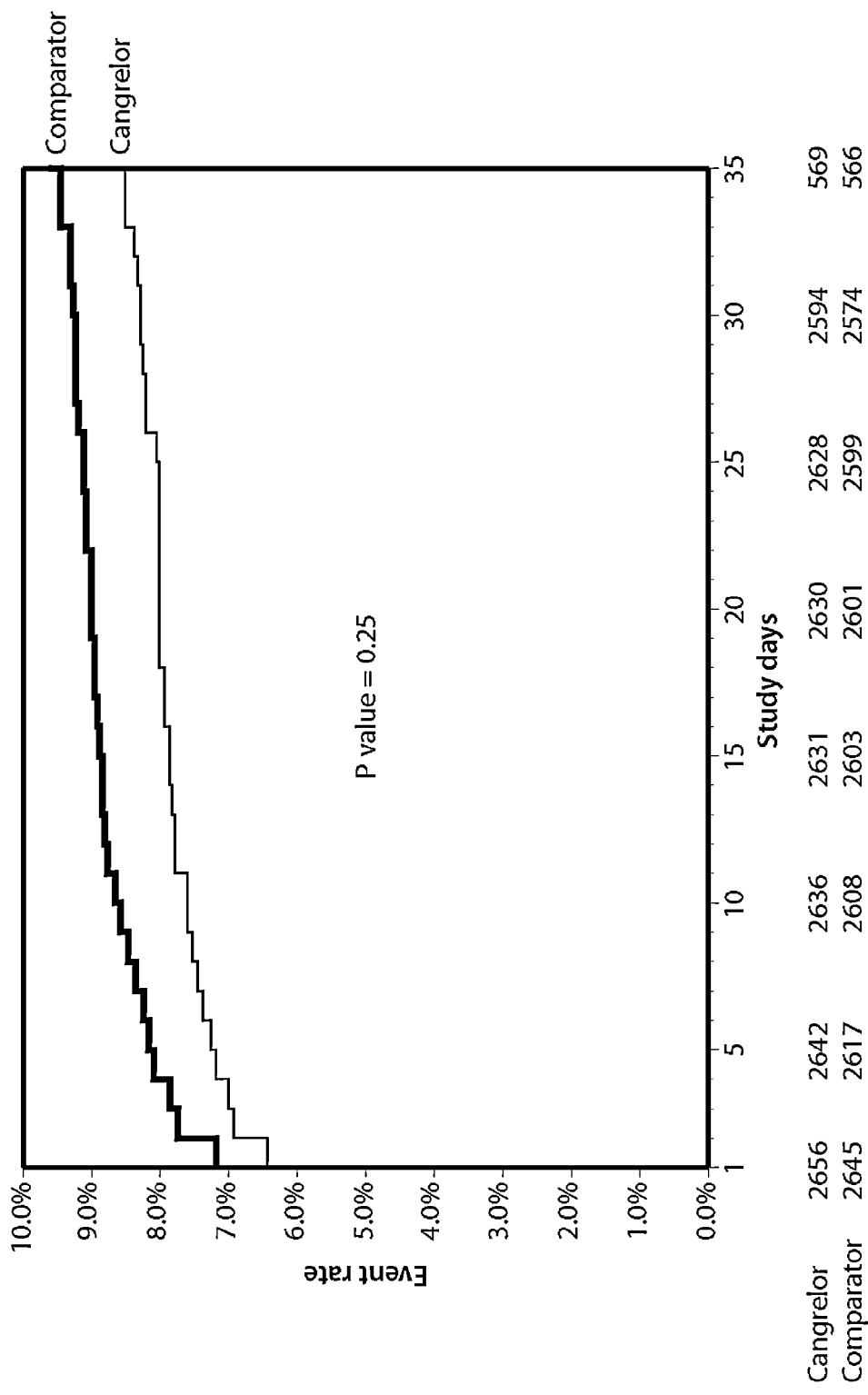
FIGS. 3A, 3B and 3C show landmark analysis of Kaplan-Meier curves for the primary efficacy endpoint (FIG. 3A), stent thrombosis (FIG. 3B), and mortality at 48 hours and 30 days (FIG. 3C) in the study described in Example 1.

The majority of patients were enrolled with non-ST-segment elevation myocardial infarction (59.8%). During PCI, unfractionated heparin was the most frequently used antithrombin (63.9%) and glycoprotein IIb/IIIa inhibitors were used sparingly (9.2%). Drug-eluting stents were used less often than bare metal stents (38.7% vs 56.9%). The time from hospital admission to PCI was short (median of 7.9 hours [3.3, 24.1]). The primary endpoint occurred in 7.0% of patients receiving cangrelor and 8.0% of patients receiving placebo (OR 0.87, 95% CI 0.71-1.07; P=0.17) (Table 2, FIG. 3A).

Figure 3B:
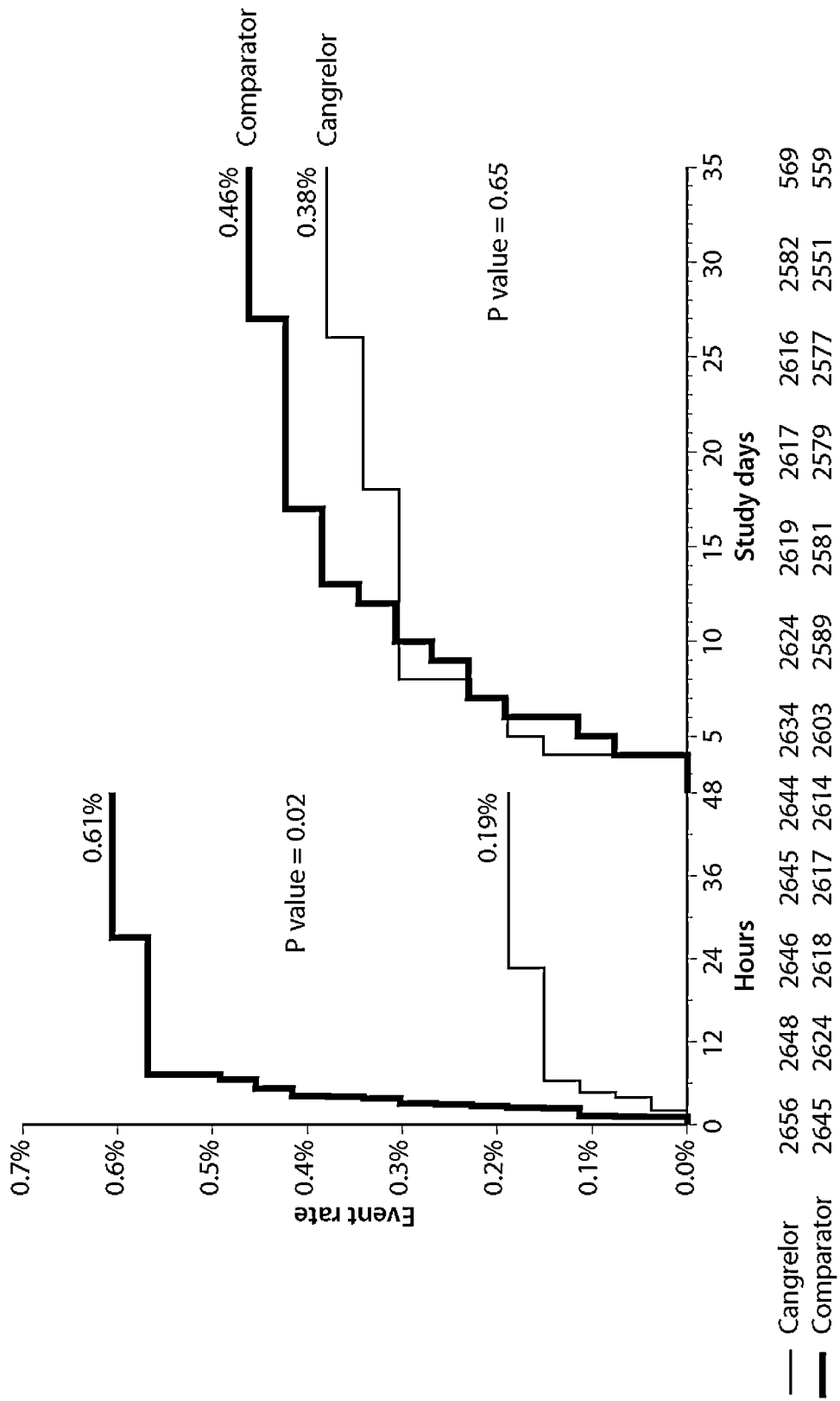

There was no significant difference in overall myocardial infarction, Q-wave myocardial infarction, or ischemia-driven revascularization (Table 2). Rates of stent thrombosis were significantly lower with cangrelor (0.2% vs 0.6% [OR 0.31, 95% CI 0.11-0.85; P=0.022]) (FIG. 3B). The rate of mortality

TABLE 2

48-hour endpoints for MITT, ITT, and Safety Populations.

MITT

| | Cangrelor (N = 2656) | Clopidogrel (N = 2645) | OR (95% CI) | P Value |
|---|---|---|---|---|
| Adjudicated endpoints | | | | |
| Mortality/MI/IDR (primary endpoint) | 185 (7.0) | 210 (8.0) | 0.867 (0.706, 1.065) | 0.1746 |
| MI | 177 (6.7) | 191 (7.2) | 0.917 (0.742, 1.133) | 0.4207 |
| IDR | 19 (0.7) | 24 (0.9) | 0.786 (0.430, 1.439) | 0.4354 |
| All-cause mortality | 6 (0.2) | 18 (0.7) | 0.330 (0.131, 0.833) | 0.0190 |
| Stroke | 7 (0.3) | 5 (0.2) | 1.394 (0.442, 4.398) | 0.5708 |
| Stent thrombosis | 5 (0.2) | 16 (0.6) | 0.310 (0.113, 0.847) | 0.0223 |
| Q-wave MI | 4 (0.2) | 8 (0.3) | 0.497 (0.149, 1.652) | 0.2538 |
| Exploratory endpoints | | | | |
| Mortality/Q-wave MI/IDR | 23 (0.9) | 41 (1.6) | 0.554 (0.332, 0.926) | 0.0243 |
| Mortality/Q-wave MI/Stent thrombosis | 13 (0.5) | 34 (1.3) | 0.377 (0.199, 0.717) | 0.0029 |

ITT

| | Cangrelor (N = 2693) | Clopidogrel (N = 2669) | OR (95% CI) | P Value |
|---|---|---|---|---|
| Adjudicated endpoints | | | | |
| Mortality/MI/IDR | 187 (6.9) | 213 (8.0) | 0.859 (0.701, 1.054) | 0.1456 |
| MI | 177 (6.6) | 192 (7.2) | 0.906 (0.734, 1.120) | 0.3632 |
| IDR | 19 (0.7) | 26 (1.0) | 0.721 (0.398, 1.307) | 0.2814 |
| All-cause mortality | 8 (0.3) | 19 (0.7) | 0.415 (0.181, 0.950) | 0.0374 |
| Stroke | 7 (0.3) | 6 (0.2) | 1.155 (0.388, 3.442) | 0.7954 |
| Stent thrombosis | 5 (0.2) | 16 (0.6) | 0.308 (0.113, 0.842) | 0.0218 |
| Q-wave MI | 4 (0.1) | 9 (0.3) | 0.439 (0.135, 1.428) | 0.1713 |
| Exploratory endpoints | | | | |
| Mortality/Q-wave MI/IDR | 25 (0.9) | 44 (1.7) | 0.558 (0.341, 0.915) | 0.0207 |
| Mortality/Q-wave MI/Stent thrombosis | 15 (0.6) | 36 (1.4) | 0.409 (0.224, 0.749) | 0.0038 |

Safety

| | Cangrelor (N = 2662) | Clopidogrel (N = 2650) | OR (95% CI) | P Value |
|---|---|---|---|---|
| Adjudicated endpoints | | | | |
| Mortality/MI/IDR | 185 (7.0) | 212 (8.0) | 0.858 (0.699, 1.053) | 0.1436 |
| MI | 176 (6.6) | 193 (7.3) | 0.901 (0.729, 1.113) | 0.3322 |
| IDR | 19 (0.7) | 25 (0.9) | 0.754 (0.414, 1.373) | 0.3561 |
| All-cause mortality | 7 (0.3) | 18 (0.7) | 0.385 (0.161, 0.924) | 0.0326 |
| Stroke | 7 (0.3) | 5 (0.2) | 1.394 (0.442, 4.396) | 0.5712 |
| Stent thrombosis | 5 (0.2) | 16 (0.6) | 0.310 (0.113, 0.846) | 0.0223 |
| Q-wave MI | 4 (0.2) | 9 (0.3) | 0.441 (0.136, 1.435) | 0.1738 |
| Exploratory endpoints | | | | |
| Mortality/Q-wave MI/IDR | 24 (0.9) | 42 (1.6) | 0.564 (0.341, 0.935) | 0.0263 |
| Mortality/Q-wave MI/Stent thrombosis | 14 (0.5) | 35 (1.3) | 0.395 (0.212, 0.735) | 0.0034 |

Figure 3C:
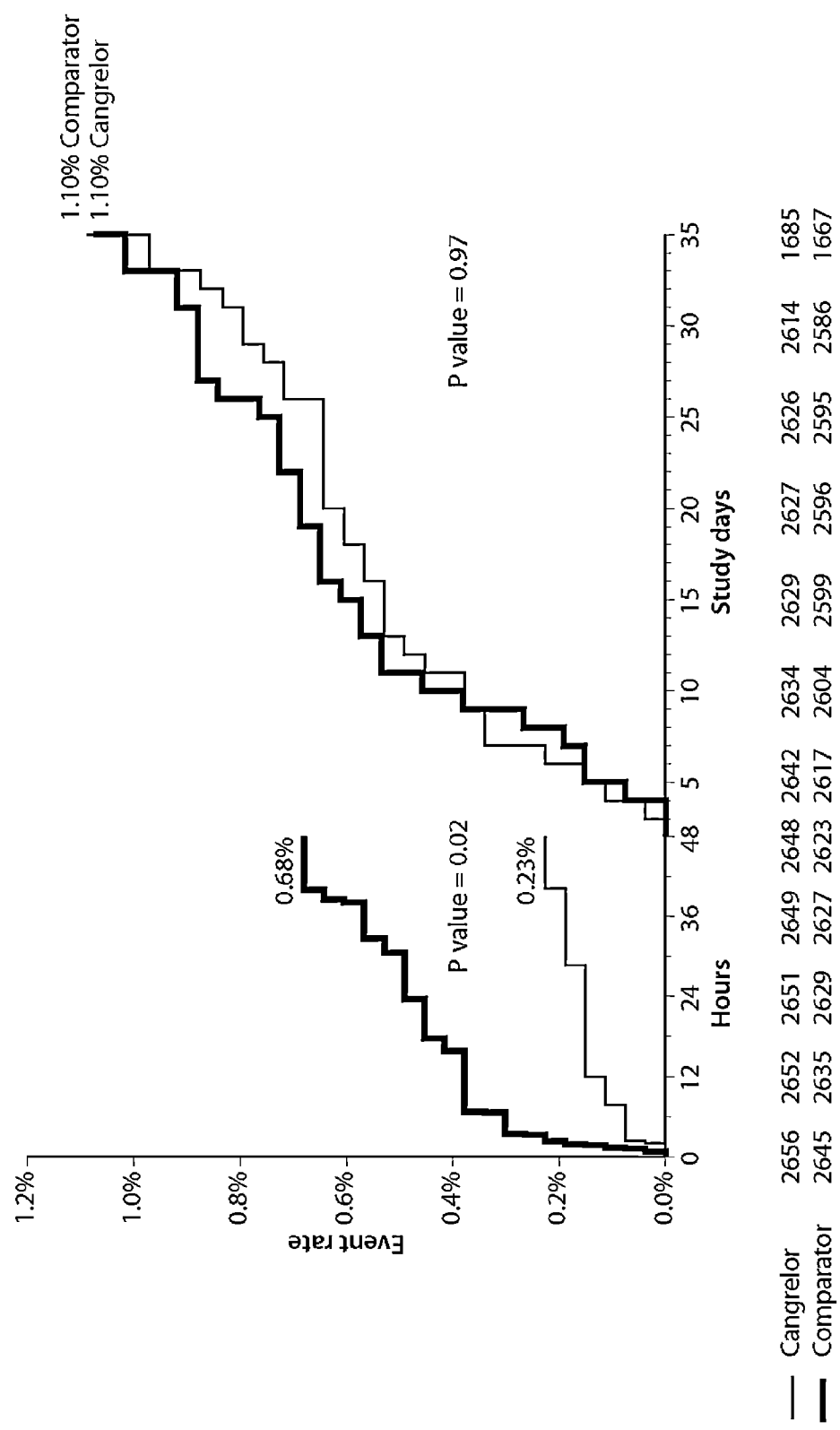

Variables are presented as no. (%) unless otherwise indicated.
CI denotes confidence interval;
IDR, ischemia-driven revascularization;
ITT, intent to treat;
MI, myocardial infarction;
MITT, modified intent to treat;
OR, odds ratio.

at 48 hours was significantly lower in the cangrelor arm (0.2% vs 0.7% [OR 0.33, 95% CI 0.13-0.83; P=0.019]), though by 30 days, this difference was no longer significant (Table 3, FIG. 3C).

TABLE 3

30-day endpoints for ITT, MITT, and Safety Populations.

ITT

|  | Cangrelor (N = 2693) | Clopidogrel (N = 2669) | OR (95% CI) | P Value |
|---|---|---|---|---|
| Adjudicated endpoints |  |  |  |  |
| Mortality/MI/IDR | 230 (8.6) | 254 (9.6) | 0.885 (0.734, 1.067) | 0.1999 |
| MI | 190 (7.1) | 202 (7.6) | 0.924 (0.752, 1.135) | 0.4515 |
| IDR | 37 (1.4) | 49 (1.8) | 0.743 (0.483, 1.142) | 0.1752 |
| All-cause mortality | 36 (1.3) | 47 (1.8) | 0.754 (0.487, 1.167) | 0.2048 |
| Stent thrombosis | 15 (0.6) | 29 (1.1) | 0.508 (0.272, 0.950) | 0.0340 |
| Q-wave MI | 8 (0.3) | 15 (0.6) | 0.526 (0.222, 1.242) | 0.1425 |
| Exploratory endpoints |  |  |  |  |
| Mortality/Q-wave MI/IDR | 69 (2.6) | 94 (3.5) | 0.718 (0.524, 0.984) | 0.0396 |
| Mortality/Q-wave MI/Stent thrombosis | 51 (1.9) | 77 (2.9) | 0.648 (0.453, 0.927) | 0.0174 |

MITT

|  | Cangrelor (N = 2656) | Clopidogrel (N = 2645) | OR (95% CI) | P Value |
|---|---|---|---|---|
| Adjudicated endpoints |  |  |  |  |
| Mortality/MI/IDR | 226 (8.5) | 249 (9.5) | 0.892 (0.739, 1.078) | 0.2365 |
| MI | 189 (7.1) | 201 (7.6) | 0.929 (0.756, 1.142) | 0.4831 |
| IDR | 37 (1.4) | 46 (1.7) | 0.796 (0.515, 1.231) | 0.3054 |
| All-cause mortality | 33 (1.2) | 45 (1.7) | 0.725 (0.461, 1.140) | 0.1635 |
| Stent thrombosis | 15 (0.6) | 28 (1.1) | 0.529 (0.282, 0.993) | 0.0477 |
| Q-wave MI | 8 (0.3) | 14 (0.5) | 0.566 (0.237, 1.352) | 0.2003 |
| Exploratory endpoints |  |  |  |  |
| Mortality/Q-wave MI/IDR | 66 (2.5) | 89 (3.4) | 0.730 (0.528, 1.008) | 0.0560 |
| Mortality/Q-wave MI/Stent thrombosis | 48 (1.8) | 73 (2.8) | 0.647 (0.447, 0.935) | 0.0203 |

TABLE 3-continued 30-day endpoints for ITT, MITT, and Safety Populations.

Safety

|  | Cangrelor (N = 2662) | Clopidogrel (N = 2650) | OR (95% CI) | P Value |
|---|---|---|---|---|
| Adjudicated endpoints |  |  |  |  |
| Mortality/MI/IDR | 226 (8.5) | 251 (9.5) | 0.884 (0.732, 1.067) | 0.1999 |
| MI | 188 (7.1) | 203 (7.7) | 0.913 (0.743, 1.122) | 0.3887 |
| IDR | 37 (1.4) | 47 (1.8) | 0.779 (0.504, 1.202) | 0.2584 |
| All-cause mortality | 34 (1.3) | 45 (1.7) | 0.747 (0.477, 1.170) | 0.2024 |
| Stent thrombosis | 15 (0.6) | 28 (1.1) | 0.529 (0.282, 0.993) | 0.0475 |
| Q-wave MI | 8 (0.3) | 15 (0.6) | 0.528 (0.224, 1.248) | 0.1455 |
| Exploratory endpoints |  |  |  |  |
| Mortality/Q-wave MI/IDR | 67 (2.5) | 90 (3.4) | 0.732 (0.531, 1.010) | 0.0572 |
| Mortality/Q-wave MI/Stent thrombosis | 49 (1.8) | 74 (2.8) | 0.651 (0.452, 0.938) | 0.0212 |

Variables are presented as no. (%) unless otherwise indicated.
CI denotes confidence interval;
IDR, ischemia-driven revascularization;
ITT, intent to treat;
MI, myocardial infarction;
MITT, modified intent to treat;
OR, odds ratio.

In the subgroup of 1659 patients enrolled without baseline troponin elevation, the primary efficacy endpoint was reduced with cangrelor from 7.2% to 4.6% (OR 0.62, 95% CI 0.41, 0.95; P=0.0266). Therefore, exploratory analyses were performed in the overall study population examining the following two clinical endpoints: mortality, Q-wave myocardial infarction, or stent thrombosis; and mortality, Q-wave myocardial infarction, or ischemia-driven revascularization. These endpoints were significantly reduced in favor of cangrelor.

The rates of Thrombolysis in Myocardial Infarction (TIMI) major or minor or Global Utilization of Streptokinase and Tissue Plasminogen Activator for Occluded Coronary Arteries (GUSTO) severe or moderate bleeding were not significantly different between the groups, though the rates of Acute Catheterization and Urgent Intervention Triage Strategy (ACUITY) major and minor bleeding and of GUSTO mild bleeding were significantly higher with cangrelor (Table 4).

TABLE 4

48-hour bleeding events for safety population.

| Bleeding Events | Cangrelor (N = 2662) | Placebo (N = 2650) | Odds Ratio (95% CI) | P Value |
|---|---|---|---|---|
| Access site bleeding requiring radiologic or surgical intervention | 8 (0.3) | 10 (0.4) | 0.796 (0.314, 2.019) | 0.6307 |
| Hematoma ≥5 cm at puncture site | 115 (4.3) | 71 (2.7) | 1.640 (1.214, 2.216) | 0.0013 |
| Intracranial hemorrhage | 2 (0.1) | 1 (0.0) | 1.992 (0.180, 21.978) | 0.5738 |
| Intraocular | 0 (0.0) | 0 (0.0) |  |  |
| Reoperation for bleeding | 1 (0.0) | 1 (0.0) | 0.995 (0.062, 15.924) | 0.9975 |
| Retroperitoneal | 2 (0.1) | 1 (0.0) | 1.992 (0.180, 21.978) | 0.5738 |
| Ecchymosis | 95 (3.6) | 57 (2.2) | 1.684 (1.207, 2.349) | 0.0022 |
| Epistaxis | 6 (0.2) | 12 (0.5) | 0.497 (0.186, 1.325) | 0.1622 |
| Hematoma <5 cm at puncture site | 150 (5.6) | 119 (4.5) | 1.270 (0.992, 1.626) | 0.0577 |
| Oozing at puncture site | 125 (4.7) | 91 (3.4) | 1.385 (1.052, 1.825) | 0.0204 |
| Thrombocytopenia | 2 (0.1) | 3 (0.1) | 0.663 (0.111, 3.973) | 0.6532 |
| Hemodynamic compromise | 7 (0.3) | 5 (0.2) | 1.395 (0.442, 4.400) | 0.5704 |
| Any blood transfusion | 26 (1.0) | 16 (0.6) | 1.624 (0.869, 3.034) | 0.1285 |

TABLE 4-continued 48-hour bleeding events for safety population.

| Bleeding Events | Cangrelor (N = 2662) | Placebo (N = 2650) | Odds Ratio (95% CI) | P Value |
|---|---|---|---|---|
| Any platelet transfusion | 4 (0.2) | 2 (0.1) | 1.992 (0.365, 10.887) | 0.4263 |
| Any red blood cell transfusion | 25 (0.9) | 15 (0.6) | 1.665 (0.876, 3.166) | 0.1197 |
| Drop in hemoglobin and/or hematocrit | 33 (1.2) | 35 (1.3) | 0.938 (0.581, 1.514) | 0.7927 |
| Bleed scoring criteria | | | | |
| ACUITY criteria | | | | |
| Minor bleeding | 320 (12.0) | 246 (9.3) | 1.335 (1.120, 1.592) | 0.0013 |
| Major bleeding | 147 (5.5) | 93 (3.5) | 1.607 (1.232, 2.096) | 0.0005 |
| GUSTO criteria | | | | |
| Mild bleeding | 427 (16.0) | 310 (11.7) | 1.442 (1.232, 1.688) | <.0001 |
| Moderate bleeding | 20 (0.8) | 13 (0.5) | 1.536 (0.762, 3.093) | 0.2300 |
| Severe/life-threatening bleeding | 9 (0.3) | 6 (0.2) | 1.495 (0.531, 4.205) | 0.4462 |
| TIMI criteria | | | | |
| Minor bleeding | 22 (0.8) | 16 (0.6) | 1.372 (0.719, 2.618) | 0.3376 |
| Major bleeding | 4 (0.2) | 9 (0.3) | 0.442 (0.136, 1.436) | 0.1742 |

Variables are presented as no. (%) unless otherwise indicated. The bleeding options under each criterion are not mutually exclusive. For example, a patient may have a clinically significant bleed and a minor bleed based on the ACUITY criteria, if more than 1 bleed is present. Each patient was counted only once for each criteria level, regardless of the number of bleeds identified under each criterion. Bleeding listed here included CABG-related bleeding.

Figure 4:
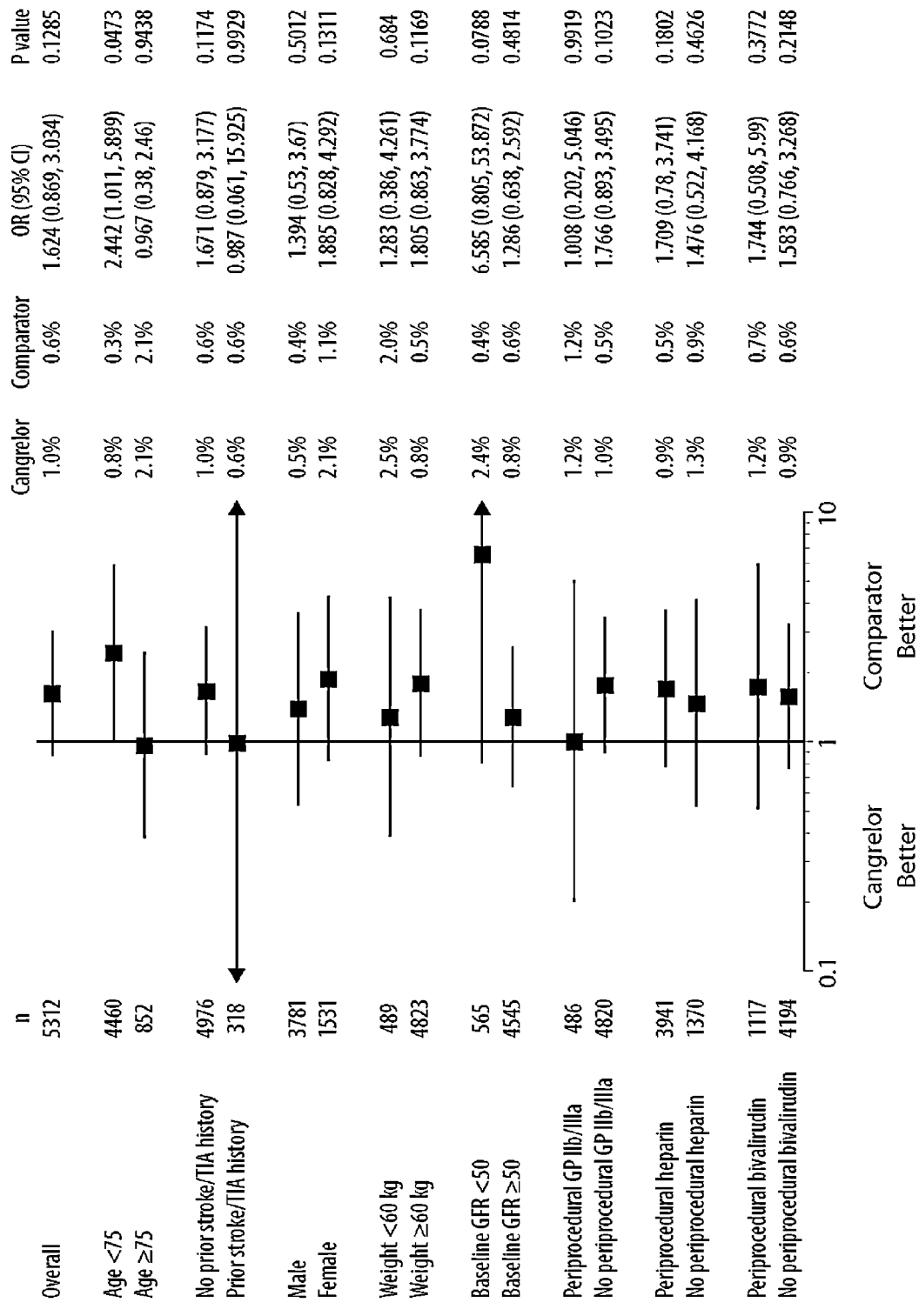
FIG. 4 shows a diagram of transfusion rates for all patients (including coronary artery bypass graft) in subgroups at high risk of bleeding in the study described in Example 1.

The difference in ACUITY major bleeding was due to an excess of groin hematomas, but not more serious forms of bleeding. The rates of red blood cell transfusion were not significantly different (0.9% with cangrelor vs 0.6% with placebo; P=0.12). Notably, patients at higher risk of bleeding, such as the elderly or those with prior stroke or transient ischemic attack, did not have a higher rate of transfusion with cangrelor (FIG. 4). There was no difference in the rate of arrhythmia (2.3% vs 2.4%; P=0.7664) and the incidence of dyspnea was higher with cangrelor (1.4% [37] vs 0.5% [14]; P=0.0019).

The results demonstrate that important prespecified endpoints, including stent thrombosis and mortality, were significantly reduced by cangrelor.

Example 2

Platelet Inhibition with Cangrelor in Patients with Acute Coronary Syndromes Undergoing Percutaneous Coronary Intervention In this example, the efficacy of cangrelor versus clopidogrel was examined when administered to patients before percutaneous coronary intervention (PCI).

Patients were eligible for enrollment if they had stable angina, unstable angina, or non-ST-segment elevation (NSTE) MI with obstructive coronary artery disease and were scheduled to undergo PCI. An additional 1000 patients with STEMI for whom primary PCI was planned were also eligible. A protocol amendment issued in May 2007 required that patients have definite features of an acute coronary syndrome (either STEMI undergoing planned primary PCI or a NSTE acute coronary syndrome with positive cardiac biomarkers or chest pain with dynamic electrocardiographic changes in patients ≥65 years or with diabetes). Patients could not have received fibrinolysis or glycoprotein IIb/IIIa inhibitors within the prior 12 hours or clopidogrel >75 mg/day in the prior 5 days.

Figure 5:
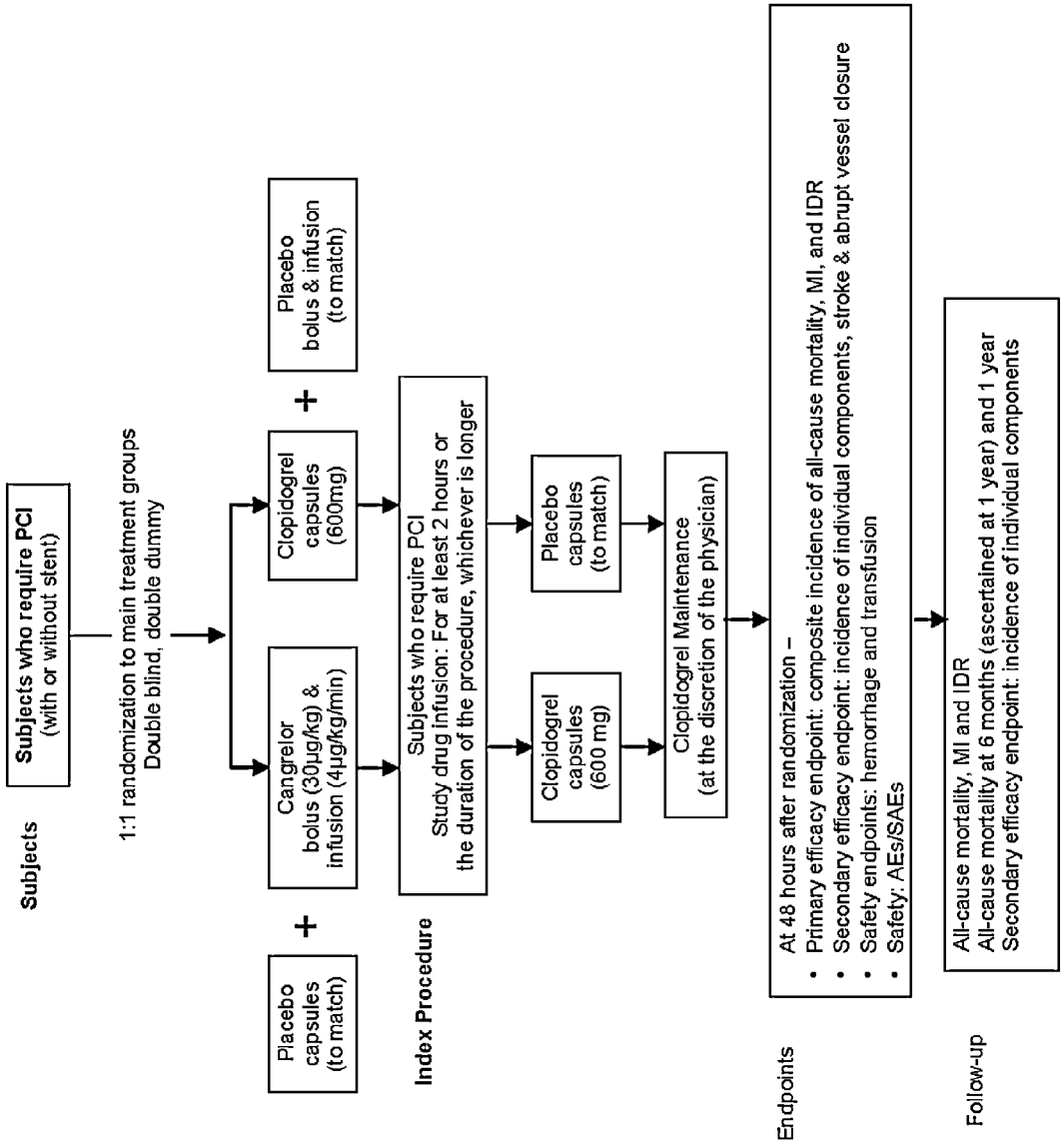
FIG. 5 shows a diagram of the trial design for the study described in Example 2.

Patients were randomized in a 1:1 double-blind, double-dummy fashion using an IVRS system to either cangrelor or clopidogrel. All patients received a 30 µg/kg intravenous bolus of cangrelor or placebo followed by a 4 µg/kg/min intravenous infusion (FIG. 5). The infusion began within 30 minutes prior to PCI and continued for at least 2 hours or until the conclusion of the index procedure, whichever was longer. At the treating physician's discretion, the infusion could be continued for 4 hours. Patients received 600 mg encapsulated clopidogrel (four 150 mg capsules) or placebo at the time of infusion. To allow the transition from intravenous cangrelor to oral clopidogrel, patients ingested another four capsules (clopidogrel for cangrelor patients, placebo for clopidogrel patients) at the cessation of study drug infusion. The duration of daily clopidogrel following the procedure was left to the discretion of the treating physician, though additional clopidogrel beyond the prescribed study medication was not allowed until the day following the index procedure.

All patients received aspirin 75-325 mg per local site standards. Adjunctive anticoagulants (unfractionated heparin, low molecular weight heparin, bivalirudin, or fondaparinux) and the procedural use of glycoprotein IIb/IIIa inhibitors were determined by the treating physician.

The primary efficacy endpoint was the 48-hour composite of all-cause mortality, MI, or ischemia-driven revascularization. Prespecified secondary efficacy endpoints included the composite of mortality or MI at 48 hours and 30 days; the composite of mortality, MI, or ischemia-driven revascularization at 30 days; the components of the composite endpoints at 48 hours and 30 days; stroke at 48 hours; abrupt closure, threatened abrupt closure, need for urgent coronary artery bypass grafting, or unsuccessful procedure during the index PCI; acute (24 hours) and 48 hours stent thrombosis; and all-cause mortality at 6 months and 1 year.

Rates of MI and ischemia-driven revascularization up to 30 days following the index procedure were assessed. Ischemia-driven revascularization was defined as symptoms of myocardial ischemia leading to urgent (within 24 hours of the last episode of ischemia) revascularization, which must have occurred after the index procedure concluded (i.e., guidewire removal). New electrocardiographic changes, acute pulmonary edema, ventricular arrhythmias, or hemodynamic instability could also constitute evidence of ischemia.

MI was defined by a new Q wave (duration >0.03 seconds) in two contiguous electrocardiographic leads or elevations in creatine kinase (CK) and CK-MB, including a rise of CK- MB≥3 times the local upper limit or normal and, when biomarkers were elevated prior to PCI, an additional 50% above baseline. One baseline troponin measurement was required for patients undergoing urgent PCI. Measurements of CK-MB were obtained at 2, 10, 17, and 24 hours post-PCI. Stent thrombosis was defined using Academic Research Consortium criteria (Cutlip D. E. et al., *Circulation* 115:2344-51 (2007)).

Bleeding was assessed up to 48 hours using clinical and laboratory definitions. Multiple definitions of bleeding were used for full disclosure of bleeding risks associated with cangrelor: (1) The Global Utilization of Streptokinase and Tissue Plasminogen Activator for Occluded Coronary Arteries (GUSTO) criteria (The GUSTO Investigators. *N Engl J Med* 329:673-82 (1993); mild, moderate, or severe/life-threatening based on transfusion use and presence/absence of hemodynamic compromise); (2) Thrombolysis in Myocardial Infarction (TIMI) criteria (Chesebro J. H. et al., *Circulation* 76:142-54 (1987); minor or major bleeding based on clinical and laboratory findings); (3) Acute Catheterization and Urgent Intervention Triage Strategy (ACUITY) criteria (Stone G. W. et al., *N Engl J Med* 355:2203-16 (2006); using detailed clinical assessment, changes in hemoglobin, hematomas >5 cm, and need for blood transfusion). Investigators reported adverse and serious adverse events according to International Conference on Harmonization guidance (International Conference on Harmonization (ICH) Guidance Documents. U.S. Food and Drug Administration Web site. (Accessed on Oct. 8, 2009, at the FDA website beginning with "www." and ending with "fda.gov/RegulatoryInformation/Guidances/ucm122049.htm")).

An independent clinical events committee reviewed and adjudicated suspected MI, ischemia-driven revascularization, stent thrombosis, and stroke blinded to knowledge of the study medication (Mahaffey K. W. et al., *Am Heart J* 143: 242-8 (2002)).

Determination of periprocedural MI can be challenging when most patients have elevated biomarkers and a single baseline sample. After the initial analyses were completed and reviewed, additional post-hoc composites were performed to better understand the potential effect of the drug on periprocedural outcomes less reliant on biomarkers (e.g., mortality, stent thrombosis, and Q-wave MI).

The sample size was based on the estimated composite incidence of all-cause mortality, MI, and ischemia-driven revascularization at 48 hours. Since there was no prior information about the use of cangrelor in the setting of STEMI and primary PCI and given the challenge of measuring re-infarction in the early hours of STEMI, the primary efficacy endpoint excluded these patients from the analysis, though they were included in analyses of safety. The composite event rate was estimated at 7% in the control clopidogrel arm. The trial was designed as a superiority trial to demonstrate a benefit of cangrelor over 600 mg clopidogrel. Assuming a 22% risk reduction, a sample size of 8000 patients would provide approximately 82% power with an alpha level of 0.05. The plan was to include up to 1000 patients with STEMI, raising the sample size to 9000 patients.

The primary efficacy analysis was to be determined in the modified intent-to-treat (mITT) population, defined as all randomized patients (excluding STEMI cohort) who received at least one dose of study drug and underwent the index PCI. The safety population consisted of all randomized patients who received any study drug. Patients in the safety analyses were assigned to a treatment arm based on treatment received, not as randomized. The ITT analysis with and without the STEMI cohort is reported.

All statistical tests were two-tailed using a level of significance of 0.05. The primary endpoint comparison between the cangrelor and placebo arms was performed by calculating an odds ratio (OR), with accompanying 95% confidence intervals (CI), using logistic regression. Logistic regression was used to analyze the majority of the remaining secondary endpoints. Continuous variables are summarized by medians and interquartile ranges. Categorical variables are summarized by frequencies and percentages. In the secondary efficacy analyses, there was no attempt to adjust the P values for the multiplicity issue. These analyses were considered exploratory and hypothesis-generating.

At the end of the study, 98% (n=8877) of the expected 9000 patients had been enrolled at 268 sites across 14 countries. For the 48-hour and 30-day endpoints, vital status follow-up was 99.7% and 98.6% complete, respectively.

Baseline demographics on the ITT population are shown in Table 5. Baseline demographics for the MITT and safety populations are shown in Tables 6 and 7.

TABLE 6

MITT and MITT NSTEMI Population.

| Baseline characteristics | MITT | | MITT NSTEMI | |
|---|---|---|---|---|
| | Cangrelor (N = 4347) | Clopidogrel (N = 4320) | Cangrelor (N = 3897) | Clopidogrel (N = 3871) |
| Age, yrs | 62.0 (54.0, 70.0) | 62.0 (54.0, 71.0) | 63.0 (55.0, 70.0) | 62.0 (54.0, 71.0) |
| Sex, No. (%) | | | | |
| Male | 3212 (73.9) | 3124 (72.3) | 2854 (73.2) | 2786 (72.0) |
| Female | 1135 (26.1) | 1196 (27.7) | 1043 (26.8) | 1085 (28.0) |
| Race, No. (%) | | | | |
| White | 3589 (82.7) | 3516 (81.5) | 3193 (82.0) | 3127 (80.9) |
| Asian | 306 (7.0) | 312 (7.2) | 289 (7.4) | 299 (7.7) |
| Black | 208 (4.8) | 230 (5.3) | 185 (4.8) | 205 (5.3) |
| Hispanic | 205 (4.7) | 214 (5.0) | 194 (5.0) | 201 (5.2) |
| Other | 34 (0.8) | 42 (1.0) | 31 (0.8) | 34 (0.9) |
| Weight, kg | 84.0 (73.0, 97.0) | 84.0 (73.0, 97.0) | 84.0 (73.0, 97.0) | 84.0 (73.0, 97.0) |
| Height, cm | 172.0 (165.0, 178.0) | 172.0 (165.0, 178.0) | 172.0 (165.0, 178.0) | 172.0 (165.0, 178.0) |
| Stable angina, No. (%) | 659 (15.2) | 645 (14.9) | 659 (16.9) | 645 (16.7) |
| Unstable angina, No. (%) | 1088 (25.0) | 1071 (24.8) | 1088 (27.9) | 1071 (27.7) |
| Urgent NSTEMI, No. (%) | 627 (14.4) | 632 (14.6) | 627 (16.1) | 632 (16.3) |
| NSTEMI, No. (%) | 1523 (35.0) | 1523 (35.3) | 1523 (39.1) | 1523 (39.3) |
| STEMI, No. (%) | 450 (10.4) | 449 (10.4) | 0 (0.0) | 0 (0.0) |

TABLE 6-continued

MITT and MITT NSTEMI Population.

| Baseline characteristics | MITT | | MITT NSTEMI | |
| --- | --- | --- | --- | --- |
| | Cangrelor (N = 4347) | Clopidogrel (N = 4320) | Cangrelor (N = 3897) | Clopidogrel (N = 3871) |
| Medical history, No. (%) | | | | |
| Diabetes mellitus | 1327 (30.5) | 1313 (30.4) | 1233 (31.7) | 1238 (32.0) |
| Current smoker | 1229 (28.6) | 1245 (29.0) | 1025 (26.6) | 1057 (27.5) |
| Hypertension | 3122 (72.2) | 3045 (70.9) | 2865 (73.8) | 2788 (72.3) |
| Hyperlipidemia | 2771 (66.6) | 2705 (65.7) | 2555 (68.3) | 2491 (67.3) |
| Stroke/TIA | 220 (5.1) | 218 (5.1) | 206 (5.3) | 201 (5.2) |
| Family history of CAD | 1809 (45.9) | 1825 (46.6) | 1637 (46.1) | 1656 (47.1) |
| MI | 1059 (24.7) | 1054 (24.7) | 991 (25.9) | 983 (25.8) |
| PTCA/PCI | 1247 (28.8) | 1229 (28.6) | 1181 (30.4) | 1172 (30.4) |
| CABG | 546 (12.6) | 537 (12.4) | 533 (13.7) | 521 (13.5) |
| Congestive HF | 325 (7.5) | 326 (7.6) | 314 (8.1) | 311 (8.1) |
| PAD | 320 (7.5) | 304 (7.2) | 292 (7.6) | 282 (7.4) |
| Periprocedural medications, No. (%) | | | | |
| Bivalirudin | 1298 (29.9) | 1316 (30.5) | 1232 (31.6) | 1232 (31.8) |
| UFH | 2399 (55.2) | 2404 (55.7) | 2134 (54.8) | 2132 (55.1) |
| LMWH | 364 (8.4) | 334 (7.7) | 319 (8.2) | 297 (7.7) |
| GP IIb/IIIa | 1148 (26.4) | 1160 (26.9) | 903 (23.2) | 921 (23.8) |
| Study treatment Number of target vessels, No. (%) | | | | |
| 1 | 3818 (88.0) | 3772 (87.4) | 3395 (87.3) | 3345 (86.5) |
| 2 | 482 (11.1) | 506 (11.7) | 455 (11.7) | 485 (12.5) |
| 3 | 38 (0.9) | 36 (0.8) | 38 (1.0) | 35 (0.9) |
| Drug-eluting stent, No. (%) | 2572 (59.3) | 2547 (59.0) | 2415 (62.1) | 2375 (61.4) |
| Non-drug-eluting stent, No. (%) | 1632 (37.6) | 1628 (37.7) | 1362 (35.0) | 1375 (35.6) |
| Angiographic complications (site reported) | | | | |
| Threatened abrupt closure | 13 (0.3) | 12 (0.3) | 9 (0.2) | 10 (0.3) |
| Unsuccessful procedure | 90 (2.1) | 103 (2.4) | 81 (2.1) | 92 (2.4) |
| Abrupt vessel closure | 24 (0.6) | 22 (0.5) | 20 (0.5) | 19 (0.5) |
| New thrombus or suspected thrombus | 17 (0.4) | 22 (0.5) | 16 (0.4) | 16 (0.4) |
| Acute stent thrombosis | 2 (0.0) | 5 (0.1) | 2 (0.1) | 5 (0.1) |
| Need for urgent CABG | 8 (0.2) | 6 (0.1) | 7 (0.2) | 6 (0.2) |
| IV study drug administered, No. (%) | 4345 (100.0) | 4317 (99.9) | 3895 (99.9) | 3868 (99.9) |
| Bolus administered, No. (%) | 4345 (100.0) | 4316 (99.9) | 3895 (99.9) | 3868 (99.9) |
| Infusion administered, No. (%) | 4344 (99.9) | 4317 (99.9) | 3894 (99.9) | 3868 (99.9) |
| Duration of infusion, hrs | 2.1 (2.0, 2.2) | 2.1 (2.0, 2.2) | 2.1 (2.0, 2.2) | 2.1 (2.0, 2.2) |
| Oral study drug administered, No. (%) | 4329 (99.6) | 4305 (99.7) | 3884 (99.7) | 3863 (99.8) |

Variables are presented as median (25th, 75th) unless otherwise indicated.
CABG denotes coronary artery bypass grafting;
CAD, coronary artery disease;
GP, glycoprotein;
HF, heart failure;
IV, intravenous;
LMWH, low molecular weight heparin;
MI, myocardial infarction;
MITT, modified intent to treat;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

TABLE 5

Baseline characteristics for ITT Population.

| Baseline characteristics | ITT Cangrelor (N = 4433) | ITT Clopidogrel (N = 4444) | ITT Without STEMI Cangrelor (N = 3946) | ITT Without STEMI Clopidogrel (N = 3935) | ITT With STEMI Cangrelor (N = 487) | ITT With STEMI Clopidogrel (N = 509) |
|---|---|---|---|---|---|---|
| Age, yrs | 62.0 (54.0, 70.0) | 62.0 (54.0, 71.0) | 63.0 (55.0, 71.0) | 62.0 (54.0, 71.0) | 58.0 (51.0, 67.0) | 61.0 (52.0, 70.0) |
| Sex, No. (%) | | | | | | |
| Male | 3275 (73.9) | 3209 (72.2) | 2891 (73.3) | 2831 (71.9) | 384 (78.9) | 378 (74.3) |
| Female | 1158 (26.1) | 1235 (27.8) | 1055 (26.7) | 1104 (28.1) | 103 (21.1) | 131 (25.7) |
| Race, No. (%) | | | | | | |
| White | 3658 (82.6) | 3626 (81.7) | 3229 (81.9) | 3184 (81.0) | 429 (88.1) | 442 (87.0) |
| Asian | 311 (7.0) | 313 (7.1) | 294 (7.5) | 300 (7.6) | 17 (3.5) | 13 (2.6) |
| Black | 215 (4.9) | 239 (5.4) | 190 (4.8) | 208 (5.3) | 25 (5.1) | 31 (6.1) |
| Hispanic | 209 (4.7) | 218 (4.9) | 197 (5.0) | 204 (5.2) | 12 (2.5) | 14 (2.8) |
| Other | 35 (0.8) | 42 (1.0) | 31 (0.8) | 34 (0.9) | 4 (0.8) | 8 (1.6) |
| Weight, kg | 84.0 (73.0, 97.0) | 84.0 (73.0, 97.0) | 84.0 (73.0, 97.0) | 84.0 (73.0, 98.0) | 83 (72.0, 95.0) | 82.0 (72.0, 95.0) |
| Height, cm | 172.0 (165.0, 178.0) | 172.0 (165.0, 178.0) | 172.0 (165.0, 178.0) | 172.0 (165.0, 178.0) | 173.0 (167.6, 178.0) | 172.0 (165.0, 178.0) |
| Stable angina, No. (%) | 668 (15.1) | 665 (15.0) | 668 (16.9) | 665 (16.9) | 0 (0.0) | 0 (0.0) |
| Unstable angina, No. (%) | 1097 (24.7) | 1088 (24.5) | 1097 (27.8) | 1088 (27.6) | 0 (0.0) | 0 (0.0) |
| Urgent NSTEMI, No. (%) | 639 (14.4) | 640 (14.4) | 639 (16.2) | 640 (16.3) | 0 (0.0) | 0 (0.0) |
| NSTEMI, No. (%) | 1542 (34.8) | 1542 (34.7) | 1542 (39.1) | 1542 (39.2) | 0 (0.0) | 0 (0.0) |
| STEMI, No. (%) | 487 (11.0) | 509 (11.5) | 0 (0.0) | 0 (0.0) | 487 (100.0) | 509 (100.0) |
| Medical history, No. (%) | | | | | | |
| Diabetes mellitus | 1350 (30.5) | 1352 (30.5) | 1248 (31.6) | 1263 (32.1) | 102 (20.9) | 89 (17.5) |
| Current smoker | 1247 (28.5) | 1283 (29.1) | 1035 (26.6) | 1076 (27.6) | 212 (43.7) | 207 (41.2) |
| Hypertension | 3181 (72.1) | 3139 (71.0) | 2900 (73.8) | 2839 (72.4) | 281 (58.1) | 300 (60.0) |
| Hyperlipidemia | 2825 (66.6) | 2777 (65.5) | 2590 (68.4) | 2536 (67.4) | 235 (51.5) | 241 (50.8) |
| Stroke/TIA | 223 (5.1) | 227 (5.1) | 208 (5.3) | 205 (5.2) | 15 (3.1) | 22 (4.4) |
| Family history of CAD | 1843 (45.9) | 1873 (46.5) | 1656 (46.1) | 1686 (47.1) | 187 (43.7) | 187 (41.6) |
| MI | 1075 (24.6) | 1089 (24.8) | 1003 (25.9) | 1007 (26.0) | 72 (14.9) | 82 (16.2) |
| PTCA/PCI | 1266 (28.6) | 1261 (28.5) | 1193 (30.3) | 1198 (30.6) | 73 (15.0) | 63 (12.4) |
| CABG | 557 (12.6) | 552 (12.4) | 541 (13.7) | 532 (13.5) | 16 (3.3) | 20 (3.9) |
| Congestive HF | 333 (7.6) | 338 (7.7) | 319 (8.2) | 322 (8.3) | 14 (2.9) | 16 (3.2) |
| PAD | 323 (7.4) | 315 (7.2) | 294 (7.6) | 290 (7.5) | 29 (6.0) | 25 (5.0) |
| Periprocedural medications, No. (%) | | | | | | |
| Bivalirudin | 1313 (29.6) | 1337 (30.1) | 1244 (31.5) | 1250 (31.8) | 69 (14.2) | 87 (17.1) |
| UFH | 2437 (55.0) | 2452 (55.3) | 2154 (54.6) | 2155 (54.8) | 283 (58.2) | 297 (58.5) |
| LMWH | 368 (8.3) | 340 (7.7) | 322 (8.2) | 298 (7.6) | 46 (9.5) | 42 (8.3) |
| GP IIb/IIIa | 1163 (26.3) | 1183 (26.7) | 909 (23.0) | 927 (23.6) | 254 (52.3) | 256 (50.4) |
| Study treatment | | | | | | |
| Number of target vessels, No. (%) | | | | | | |
| 1 | 3836 (88.0) | 3796 (87.4) | 3406 (87.3) | 3360 (86.5) | 430 (94.1) | 436 (95.2) |
| 2 | 484 (11.1) | 509 (11.7) | 457 (11.7) | 488 (12.6) | 27 (5.9) | 21 (4.6) |
| 3 | 38 (0.9) | 36 (0.8) | 38 (1.0) | 35 (0.9) | 0 (0.0) | 1 (0.2) |
| Drug-eluting stent, No. (%) | 2581 (59.2) | 2560 (59.0) | 2422 (62.1) | 2383 (61.4) | 159 (34.8) | 177 (38.6) |
| Non-drug-eluting stent, No. (%) | 1640 (37.6) | 1635 (37.7) | 1367 (35.0) | 1380 (35.5) | 273 (59.7) | 255 (55.7) |
| Angiographic complications (site reported) | | | | | | |
| Threatened abrupt closure | 13 (0.3) | 12 (0.3) | 9 (0.2) | 10 (0.3) | 4 (0.9) | 2 (0.4) |
| Unsuccessful procedure | 90 (2.1) | 103 (2.4) | 81 (2.1) | 92 (2.4) | 9 (2.0) | 11 (2.4) |
| Abrupt vessel closure | 24 (0.6) | 22 (0.5) | 20 (0.5) | 19 (0.5) | 4 (0.9) | 3 (0.7) |
| New thrombus or suspected thrombus | 17 (0.4) | 23 (0.5) | 16 (0.4) | 16 (0.4) | 1 (0.2) | 7 (1.5) |
| Acute stent thrombosis | 2 (0.0) | 5 (0.1) | 2 (0.1) | 5 (0.1) | 0 (0.0) | 0 (0.0) |
| Need for urgent CABG | 10 (0.2) | 7 (0.2) | 8 (0.2) | 7 (0.2) | 2 (0.4) | 0 (0.0) |
| IV study drug administered, No. (%) | 4367 (98.5) | 4355 (98.0) | 3904 (99.0) | 3883 (98.7) | 463 (95.1) | 472 (92.7) |
| Bolus administered, No. (%) | 4367 (98.5) | 4354 (98.0) | 3904 (99.0) | 3883 (98.7) | 463 (95.1) | 471 (92.5) |
| Infusion administered, No. (%) | 4364 (98.5) | 4353 (98.0) | 3901 (98.9) | 3882 (98.7) | 463 (95.1) | 471 (92.5) |
| Duration of infusion, hrs | 2.1 (2.0, 2.2) | 2.1 (2.0, 2.2) | 2.1 (2.0, 2.2) | 2.1 (2.0, 2.2) | 2.0 (2.0, 2.2) | 2.1 (2.0, 2.2) |
| Oral study drug administered, No. (%) | 4351 (98.2) | 4345 (97.8) | 3896 (98.8) | 3882 (98.7) | 455 (93.4) | 463 (91.0) |

Variables are presented as median (25th, 75th) unless otherwise indicated. CABG denotes coronary artery bypass grafting; CAD, coronary artery disease; GP, glycoprotein; HF, heart failure; ITT, intent to treat; IV, intravenous; LMWH, low molecular weight heparin; MI, myocardial infarction; NSTEMI, non-ST-segment elevation myocardial infarction; PAD, peripheral artery disease; PCI, percutaneous coronary intervention; PTCA, percutaneous transluminal coronary angioplasty; STEMI, ST-segment elevation myocardial infarction; TIA, transient ischemic attack; UFH, unfractionated heparin.

TABLE 7

Safety Population.

| Baseline characteristics | Cangrelor (N = 4374) | Clopidogrel (N = 4365) |
|---|---|---|
| Age, yrs | 62.0 (54.0, 70.0) | 62.0 (54.0, 71.0) |
| Sex, No. (%) | | |
| Male | 3229 (73.8) | 3149 (72.1) |
| Female | 1145 (26.2) | 1216 (27.9) |
| Race, No. (%) | | |
| White | 3610 (82.6) | 3558 (81.6) |
| Asian | 309 (7.1) | 312 (7.2) |
| Black | 208 (4.8) | 233 (5.3) |
| Hispanic | 206 (4.7) | 215 (4.9) |
| Other | 36 (0.8) | 41 (1.0) |
| Weight, kg | 84.0 (73.0, 97.0) | 84.0 (73.0, 97.0) |
| Height, cm | 172.0 (165.0, 178.0) | 172.0 (165.0, 178.0) |
| Stable angina, No. (%) | 661 (15.1) | 654 (15.0) |
| Unstable angina, No. (%) | 1091 (24.9) | 1074 (24.6) |
| Urgent NSTEMI, No. (%) | 629 (14.4) | 634 (14.5) |
| NSTEMI, No. (%) | 1529 (35.0) | 1529 (35.0) |
| STEMI, No. (%) | 463 (10.6) | 475 (10.9) |
| Medical history, No. (%) | | |
| Diabetes mellitus | 1337 (30.6) | 1325 (30.4) |
| Current smoker | 1233 (28.5) | 1257 (29.0) |
| Hypertension | 3143 (72.2) | 3083 (71.0) |
| Hyperlipidemia | 2787 (66.6) | 2728 (65.6) |
| Stroke/TIA | 220 (5.1) | 221 (5.1) |
| Family history of CAD | 1818 (45.8) | 1838 (46.5) |
| MI | 1064 (24.7) | 1067 (24.8) |
| PTCA/PCI | 1253 (28.7) | 1237 (28.4) |
| CABG | 550 (12.6) | 540 (12.4) |
| Congestive HF | 328 (7.6) | 332 (7.7) |
| PAD | 321 (7.5) | 309 (7.2) |
| Periprocedural medications, No. (%) | | |
| Bivalirudin | 1299 (29.7) | 1320 (30.2) |
| UFH | 2413 (55.2) | 2424 (55.5) |
| LMWH | 365 (8.4) | 340 (7.8) |
| GP IIb/IIIa | 1154 (26.4) | 1170 (26.8) |
| Study treatment | | |
| Number of target vessels, No. (%) | | |
| 1 | 3819 (88.0) | 3771 (87.4) |
| 2 | 482 (11.1) | 506 (11.7) |
| 3 | 38 (0.9) | 36 (0.8) |
| Drug-eluting stent, No. (%) | 2572 (59.3) | 2547 (59.0) |
| Non-drug-eluting stent, No. (%) | 1633 (37.6) | 1627 (37.7) |
| Angiographic complications (site reported) | | |
| Threatened abrupt closure | 13 (0.3) | 12 (0.3) |
| Unsuccessful procedure | 90 (2.1) | 103 (2.4) |
| Abrupt vessel closure | 24 (0.6) | 22 (0.5) |
| New thrombus or suspected thrombus | 17 (0.4) | 22 (0.5) |
| Acute stent thrombosis | 2 (0.0) | 5 (0.1) |
| Need for urgent CABG | 8 (0.2) | 6 (0.1) |
| IV study drug administered, No. (%) | 4368 (99.9) | 4354 (99.7) |
| Bolus administered, No. (%) | 4368 (99.9) | 4353 (99.7) |
| Infusion administered, No. (%) | 4365 (99.8) | 4352 (99.7) |
| Duration of infusion, hrs | 2.1 (2.0, 2.2) | 2.1 (2.0, 2.2) |
| Oral study drug administered, No. (%) | 4352 (99.5) | 4344 (99.5) |

Variables are presented as median (25th, 75th) unless otherwise indicated. CABG denotes coronary artery bypass grafting; CAD, coronary artery disease; GP, glycoprotein; HF, heart failure; IV, intravenous; LMWH, low molecular weight heparin; MI, myocardial infarction; NSTEMI, non-ST-segment elevation myocardial infarction; PAD, peripheral artery disease; PCI, percutaneous coronary intervention; PTCA, percutaneous transluminal coronary angioplasty; STEMI, ST-segment elevation myocardial infarction; TIA, transient ischemic attack; UFH, unfractionated heparin.

There were no significant differences regarding baseline characteristics. Enrolled patients were typical of a contemporary PCI population, being mostly men and having a median age of 62 years (54.0, 71.0). Diabetes was noted in 30.5% while hypertension or hyperlipidemia was present in the majority of patients. Previous cardiac events included MI in 24.7% and revascularization in 41.1% (28.6% PCI, 12.5% bypass grafting). Almost half (49%) of enrolled patients had NSTEMI at baseline while stable angina and unstable angina were the baseline diagnoses in 15.0% and 24.6%, respectively. The STEMI cohort included 996 (11.2%) patients.

During the index procedure, a majority of patients (55.1%) received unfractionated heparin, and 29.9% received bivalirudin. Glycoprotein IIb/IIIa inhibitors were used in 26.5% with most receiving eptifibatide (75.0%). Almost all (98%) patients in the ITT population received study drug. Sites were instructed to start PCI within 30 minutes of clopidogrel capsules.

PCI was attempted in all but 161 patients (1.8%), 65 in the cangrelor group (1.5%) and 96 in the clopidogrel group (2.2%). The median duration of PCI was 0.4 hours (0.2, 0.6) and the median time from hospital admission to PCI was 6.3 hours (2.6, 23.7). Most procedures involved single-vessel or two-vessel PCI (87.7% and 11.4%, respectively). Drug-eluting stents were used in the majority of interventions (59.1%), bare-metal stents were used in 37.6%.

Cangrelor was equivalent to 600 mg clopidogrel in the primary composite of all-cause mortality, MI, or ischemia-driven revascularization at 48 hours (7.5% vs 7.1%; OR 1.05, 95% CI 0.88, 1.24; P=0.59) (Table 8).

TABLE 8

48-hour endpoints for MITT Without STEMI Population.

| | MITT Without STEMI | | | |
|---|---|---|---|---|
| | Cangrelor (N = 3897) | Clopidogrel (N = 3871) | OR (95% CI) | P Value |
| Adjudicated endpoints | | | | |
| Mortality/MI/IDR (primary endpoint) | 290 (7.5) | 276 (7.1) | 1.05 (0.88, 1.24) | 0.59 |
| MI | 278 (7.1) | 256 (6.6) | 1.09 (0.91, 1.29) | 0.36 |
| IDR | 13 (0.3) | 23 (0.6) | 0.56 (0.28, 1.11) | 0.10 |
| All-cause mortality | 8 (0.2) | 5 (0.1) | 1.59 (0.52, 4.87) | 0.42 |
| Stent thrombosis | 7 (0.2) | 11 (0.3) | 0.63 (0.25, 1.63) | 0.34 |
| Stroke | 6 (0.2) | 7 (0.2) | 0.85 (0.29, 2.54) | 0.77 |
| Q-wave MI | 4 (0.1) | 10 (0.3) | 0.40 (0.12, 1.27) | 0.12 |
| Exploratory endpoints | | | | |
| Mortality/Q-wave MI/IDR | 23 (0.6) | 34 (0.9) | 0.67 (0.39, 1.14) | 0.14 |
| Mortality/Q-wave MI/Stent thrombosis | 18 (0.5) | 23 (0.6) | 0.78 (0.42, 1.44) | 0.42 |

Figure 6A:
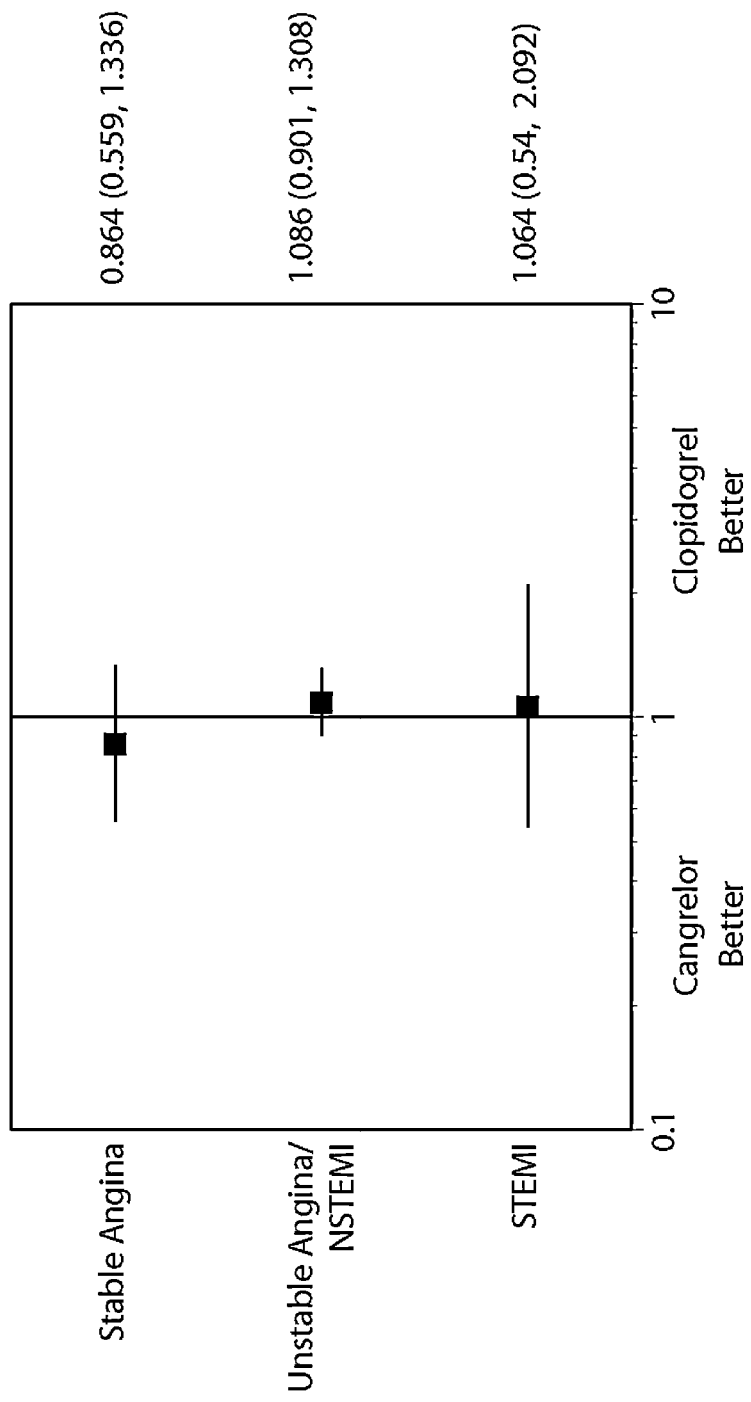
FIGS. 6A and 6B display the primary endpoint odds ratio (OR) data for key subgroups in the study described in Example 2.
Figure 6B:
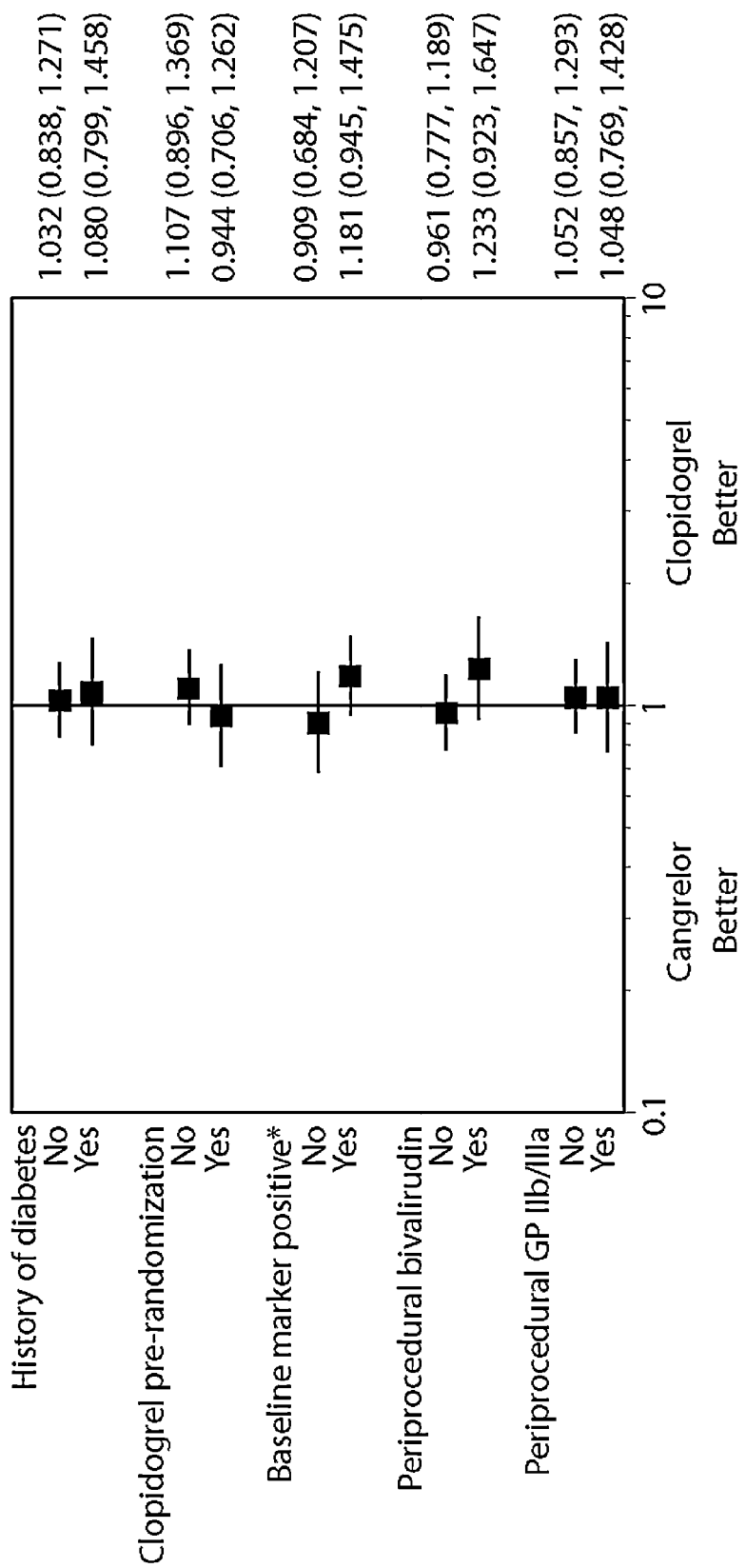

The primary efficacy composite did not differ at 30 days (Table 9). FIGS. 6A and 6B display the primary endpoint OR data for key subgroups.

TABLE 9

30-day endpoints for ITT, MITT, and Safety Populations.

ITT

|  | Cangrelor (N = 4433) | Clopidogrel (N = 4444) | OR (95% CI) | P Value |
|---|---|---|---|---|
| Mortality/MI/IDR | 381 (8.7) | 373 (8.5) | 1.026 (0.884, 1.192) | 0.7332 |
| MI | 318 (7.3) | 293 (6.7) | 1.095 (0.929, 1.291) | 0.2799 |
| IDR | 62 (1.4) | 69 (1.6) | 0.899 (0.637, 1.271) | 0.5475 |
| All-cause mortality | 40 (0.9) | 47 (1.1) | 0.852 (0.558, 1.301) | 0.4583 |
| Stent thrombosis | 27 (0.6) | 30 (0.7) | 0.902 (0.535, 1.519) | 0.6973 |
| Q-wave MI | 9 (0.2) | 15 (0.3) | 0.601 (0.263, 1.374) | 0.2273 |
| Mortality/Q-wave MI/IDR | 102 (2.3) | 119 (2.7) | 0.856 (0.655, 1.119) | 0.2550 |
| Mortality/Q-wave MI/Stent thrombosis | 68 (1.6) | 82 (1.9) | 0.829 (0.599, 1.146) | 0.2560 |

ITT Without STEMI

|  | Cangrelor (N = 3946) | Clopidogrel (N = 3935) | OR (95% CI) | P Value |
|---|---|---|---|---|
| Mortality/MI/IDR | 345 (8.8) | 332 (8.6) | 1.037 (0.886, 1.215) | 0.6481 |
| MI | 298 (7.6) | 276 (7.1) | 1.081 (0.912, 1.281) | 0.3718 |
| IDR | 46 (1.2) | 54 (1.4) | 0.846 (0.569, 1.257) | 0.4072 |
| All-cause mortality | 32 (0.8) | 31 (0.8) | 1.027 (0.626, 1.687) | 0.9148 |
| Stent thrombosis | 20 (0.5) | 20 (0.5) | 0.995 (0.535, 1.852) | 0.9877 |
| Q-wave MI | 7 (0.2) | 15 (0.4) | 0.463 (0.189, 1.138) | 0.0933 |
| Mortality/Q-wave MI/IDR | 79 (2.0) | 88 (2.3) | 0.891 (0.656, 1.211) | 0.4620 |
| Mortality/Q-wave MI/Stent thrombosis | 54 (1.4) | 56 (1.4) | 0.959 (0.658, 1.397) | 0.8276 |

ITT With STEMI

|  | Cangrelor (N = 487) | Clopidogrel (N = 509) | OR (95% CI) | P Value |
|---|---|---|---|---|
| Mortality/MI/IDR | 36 (7.6) | 41 (8.2) | 0.929 (0.582, 1.480) | 0.7553 |
| MI | 20 (4.2) | 17 (3.4) | 1.263 (0.653, 2.441) | 0.4882 |
| IDR | 16 (3.4) | 15 (3.0) | 1.139 (0.557, 2.331) | 0.7210 |
| All-cause mortality | 8 (1.7) | 16 (3.2) | 0.524 (0.222, 1.235) | 0.1397 |
| Stent thrombosis | 7 (1.5) | 10 (2.0) | 0.741 (0.280, 1.962) | 0.5460 |
| Q-wave MI | 2 (0.4) | 0 (0.0) | — | — |
| Mortality/Q-wave MI/IDR | 23 (4.9) | 31 (6.2) | 0.778 (0.447, 1.355) | 0.3760 |
| Mortality/Q-wave MI/Stent thrombosis | 14 (3.0) | 26 (5.2) | 0.560 (0.289, 1.085) | 0.0859 |

MITT

|  | Cangrelor (N = 4347) | Clopidogrel (N = 4320) | OR (95% CI) | P Value |
|---|---|---|---|---|
| Mortality/MI/IDR | 376 (8.7) | 360 (8.4) | 1.042 (0.895, 1.211) | 0.5979 |
| MI | 315 (7.3) | 292 (6.8) | 1.078 (0.914, 1.271) | 0.3747 |
| IDR | 60 (1.4) | 66 (1.5) | 0.902 (0.634, 1.283) | 0.5660 |
| All-cause mortality | 40 (0.9) | 38 (0.9) | 1.046 (0.670, 1.635) | 0.8419 |
| Stent thrombosis | 27 (0.6) | 30 (0.7) | 0.894 (0.530, 1.506) | 0.6728 |
| Q-wave MI | 9 (0.2) | 15 (0.4) | 0.595 (0.260, 1.362) | 0.2194 |
| Mortality/Q-wave MI/IDR | 100 (2.3) | 107 (2.5) | 0.927 (0.703, 1.222) | 0.5904 |
| Mortality/Q-wave MI/Stent thrombosis | 68 (1.6) | 73 (1.7) | 0.924 (0.663, 1.290) | 0.6439 |

MITT Without STEMI

|  | Cangrelor (N = 3897) | Clopidogrel (N = 3871) | OR (95% CI) | P Value |
|---|---|---|---|---|
| Mortality/MI/IDR | 342 (8.9) | 326 (8.5) | 1.044 (0.891, 1.224) | 0.5950 |
| MI | 297 (7.7) | 276 (7.2) | 1.072 (0.905, 1.272) | 0.4208 |
| IDR | 44 (1.1) | 52 (1.4) | 0.837 (0.559, 1.254) | 0.3882 |
| All-cause mortality | 32 (0.8) | 27 (0.7) | 1.177 (0.704, 1.967) | 0.5355 |
| Stent thrombosis | 20 (0.5) | 20 (0.5) | 0.991 (0.533, 1.846) | 0.9783 |
| Q-wave MI | 7 (0.2) | 15 (0.4) | 0.462 (0.188, 1.134) | 0.0917 |
| Mortality/Q-wave MI/IDR | 77 (2.0) | 82 (2.1) | 0.930 (0.679, 1.273) | 0.6489 |

TABLE 9-continued 30-day endpoints for ITT, MITT, and Safety Populations.

|  | | | | |
|---|---|---|---|---|
| Mortality/Q-wave MI/Stent thrombosis | 54 (1.4) | 52 (1.4) | 1.030 (0.702, 1.511) | 0.8799 |

MITT With STEMI

|  | Cangrelor (N = 450) | Clopidogrel (N = 449) | OR (95% CI) | P Value |
|---|---|---|---|---|
| Mortality/MI/IDR | 34 (7.8) | 34 (7.7) | 1.015 (0.619, 1.665) | 0.9534 |
| MI | 18 (4.1) | 16 (3.6) | 1.146 (0.577, 2.278) | 0.6965 |
| IDR | 16 (3.7) | 14 (3.2) | 1.165 (0.561, 2.416) | 0.6825 |
| All-cause mortality | 8 (1.8) | 11 (2.5) | 0.732 (0.292, 1.838) | 0.5072 |
| Stent thrombosis | 7 (1.6) | 10 (2.3) | 0.705 (0.266, 1.869) | 0.4821 |
| Q-wave MI | 2 (0.5) | 0 (0.0) | — | — |
| Mortality/Q-wave MI/IDR | 23 (5.3) | 25 (5.6) | 0.929 (0.519, 1.663) | 0.8039 |
| Mortality/Q-wave MI/Stent thrombosis | 14 (3.2) | 21 (4.7) | 0.665 (0.334, 1.325) | 0.2464 |

Safety

|  | Cangrelor (N = 4374) | Clopidogrel (N = 4365) | OR (95% CI) | P Value |
|---|---|---|---|---|
| Mortality/MI/IDR | 379 (8.8) | 365 (8.5) | 1.040 (0.895, 1.209) | 0.6074 |
| MI | 318 (7.4) | 293 (6.8) | 1.090 (0.925, 1.285) | 0.3039 |
| IDR | 60 (1.4) | 67 (1.6) | 0.893 (0.628, 1.268) | 0.5257 |
| All-cause mortality | 40 (0.9) | 41 (0.9) | 0.974 (0.629, 1.508) | 0.9053 |
| Stent thrombosis | 27 (0.6) | 30 (0.7) | 0.898 (0.533, 1.513) | 0.6858 |
| Q-wave MI | 9 (0.2) | 15 (0.3) | 0.598 (0.262, 1.368) | 0.2236 |
| Mortality/Q-wave MI/IDR | 100 (2.3) | 111 (2.6) | 0.897 (0.682, 1.179) | 0.4364 |
| Mortality/Q-wave MI/Stent thrombosis | 68 (1.6) | 76 (1.8) | 0.892 (0.641, 1.240) | 0.4954 |

Variables are presented as no. (%) unless otherwise indicated. CI denotes confidence internal; IDR, ischemia-driven revascularization; ITT, intent to treat; MI, myocardial infarction; MITT, modified intent to treat; OR, odds ratio; STEMI, ST-segment elevation myocardial infarction.

Forty-eight-hour bleeding events as observed in the safety population (including those with STEMI) are in Table 10. Reported adverse events were comparable between the groups (26.4% cangrelor, 25.7% clopidogrel) and discontinuation of study drug due to an adverse event was unusual in both groups (0.5% in both). Serious adverse events were infrequent and similar between the groups (2.7% in both). Dyspnea was reported in 1.0% of cangrelor patients compared with 0.4% of clopidogrel patients (P=0.001).

TABLE 10

48-hour bleeding events for safety population.

| Bleeding events | Cangrelor (N = 4374) | Clopidogrel (N = 4365) | OR (95% CI) | P Value |
|---|---|---|---|---|
| Access site bleeding requiring radiologic or surgical intervention | 6 (0.1) | 10 (0.2) | 0.60 (0.22, 1.65) | 0.32 |
| Hematoma ≥5 cm at puncture site | 85 (1.9) | 76 (1.7) | 1.12 (0.82, 1.53) | 0.48 |
| Intracranial hemorrhage | 1 (0.0) | 0 (0.0) | | |
| Intraocular | 2 (0.0) | 0 (0.0) | | |
| Reoperation for bleeding | 1 (0.0) | 1 (0.0) | 1.00 (0.06, 15.96) | 1.00 |
| Retroperitoneal | 15 (0.3) | 10 (0.2) | 1.50 (0.67, 3.34) | 0.32 |
| Ecchymosis | 284 (6.5) | 234 (5.4) | 1.23 (1.03, 1.47) | 0.03 |
| Epistaxis | 9 (0.2) | 22 (0.5) | 0.41 (0.19, 0.89) | 0.02 |
| Hematoma <5 cm at puncture site | 251 (5.7) | 222 (5.1) | 1.14 (0.94, 1.37) | 0.18 |
| Oozing at puncture site | 400 (9.1) | 319 (7.3) | 1.28 (1.10, 1.49) | 0.002 |
| Thrombocytopenia | 6 (0.1) | 7 (0.2) | 0.86 (0.29, 2.55) | 0.78 |
| Hemodynamic compromise | 9 (0.2) | 11 (0.3) | 0.82 (0.34, 1.97) | 0.65 |
| Any blood transfusion | 46 (1.1) | 42 (1.0) | 1.09 (0.72, 1.67) | 0.68 |
| Any platelet transfusion | 6 (0.1) | 5 (0.1) | 1.20 (0.37, 3.93) | 0.77 |
| Drop in hemoglobin and/or hematocrit | 91 (2.1) | 63 (1.4) | 1.45 (1.05, 2.01) | 0.02 |
| Bleed scoring criteria | | | | |
| ACUITY criteria | | | | |
| Minor bleeding | 768 (17.6) | 663 (15.2) | 1.19 (1.06, 1.33) | 0.003 |
| Major bleeding | 158 (3.6) | 126 (2.9) | 1.26 (0.99, 1.60) | 0.06 |

TABLE 10-continued 48-hour bleeding events for safety population.

| Bleeding events | Cangrelor (N = 4374) | Clopidogrel (N = 4365) | OR (95% CI) | P Value |
|---|---|---|---|---|
| GUSTO criteria | | | | |
| Mild bleeding | 858 (19.6) | 739 (16.9) | 1.20 (1.07, 1.34) | 0.001 |
| Moderate bleeding | 41 (0.9) | 34 (0.8) | 1.21 (0.76, 1.90) | 0.42 |
| Severe/life-threatening bleeding | 10 (0.2) | 11 (0.3) | 0.91 (0.39, 2.14) | 0.82 |
| TIMI criteria | | | | |
| Minor bleeding | 36 (0.8) | 26 (0.6) | 1.39 (0.84, 2.30) | 0.21 |
| Major bleeding | 19 (0.4) | 14 (0.3) | 1.36 (0.68, 2.71) | 0.39 |

Variables are presented as no. (%) unless otherwise indicated. The bleeding options under each criterion are not mutually exclusive. For example, a patient may have a clinically significant bleed and a minor bleed based on the ACUITY criteria, if more than 1 bleed is present. Each patient will be counted for each criteria level, regardless of the number of bleeds identified under each criterion.

Key secondary and composite exploratory (post-hoc) endpoints are displayed in Table 11.

TABLE 11

48-hour endpoints for ITT, MITT, and Safety Populations.

| | MITT Without STEMI | | | |
|---|---|---|---|---|
| | Cangrelor (N = 3897) | Clopidogrel (N = 3871) | OR (95% CI) | P Value |
| Mortality/MI/IDR (Prespecified primary endpoint) | 290 (7.5) | 276 (7.1) | 1.048 (0.883, 1.243) | 0.5929 |
| MI | 278 (7.1) | 256 (6.6) | 1.085 (0.910, 1.294) | 0.3616 |
| IDR | 13 (0.3) | 23 (0.6) | 0.560 (0.283, 1.108) | 0.0957 |
| All-cause mortality | 8 (0.2) | 5 (0.1) | 1.591 (0.520, 4.869) | 0.4155 |
| Stent thrombosis | 7 (0.2) | 11 (0.3) | 0.632 (0.245, 1.631) | 0.3427 |
| Stroke | 6 (0.2) | 7 (0.2) | 0.852 (0.286, 2.536) | 0.7730 |
| Q-wave MI | 4 (0.1) | 10 (0.3) | 0.397 (0.124, 1.267) | 0.1186 |
| Mortality/Q-wave MI/IDR | 23 (0.6) | 34 (0.9) | 0.670 (0.394, 1.140) | 0.1399 |
| Mortality/Q-wave MI/Stent thrombosis | 18 (0.5) | 23 (0.6) | 0.777 (0.419, 1.442) | 0.4233 |

| | ITT | | | |
|---|---|---|---|---|
| | Cangrelor (N = 4433) | Clopidogrel (N = 4444) | OR (95% CI) | P Value |
| Mortality/MI/IDR | 312 (7.1) | 297 (6.7) | 1.058 (0.898, 1.248) | 0.4990 |
| MI | 294 (6.7) | 265 (6.0) | 1.122 (0.945, 1.331) | 0.1899 |
| IDR | 21 (0.5) | 31 (0.7) | 0.678 (0.389, 1.182) | 0.1710 |
| All-cause mortality | 9 (0.2) | 11 (0.2) | 0.821 (0.340, 1.983) | 0.6607 |
| Stent thrombosis | 11 (0.2) | 15 (0.3) | 0.735 (0.337, 1.603) | 0.4393 |
| Stroke | 6 (0.1) | 8 (0.2) | 0.752 (0.261, 2.170) | 0.5986 |
| Q-wave MI | 4 (0.1) | 10 (0.2) | 0.401 (0.126, 1.279) | 0.1226 |
| Mortality/Q-wave MI/IDR | 32 (0.7) | 48 (1.1) | 0.667 (0.425, 1.045) | 0.0770 |
| Mortality/Q-wave MI/Stent thrombosis | 23 (0.5) | 33 (0.7) | 0.698 (0.409, 1.191) | 0.1869 |

| | ITT Without STEMI | | | |
|---|---|---|---|---|
| | Cangrelor (N = 3946) | Clopidogrel (N = 3935) | OR (95% CI) | P Value |
| Mortality/MI/IDR | 292 (7.4) | 277 (7.1) | 1.056 (0.890, 1.252) | 0.5323 |
| MI | 278 (7.1) | 256 (6.5) | 1.090 (0.914, 1.299) | 0.3378 |
| IDR | 15 (0.4) | 23 (0.6) | 0.649 (0.338, 1.246) | 0.1943 |
| All-cause mortality | 8 (0.2) | 6 (0.2) | 1.331 (0.461, 3.839) | 0.5969 |
| Stent thrombosis | 7 (0.2) | 11 (0.3) | 0.634 (0.246, 1.638) | 0.3469 |
| Stroke | 6 (0.2) | 7 (0.2) | 0.855 (0.287, 2.546) | 0.7784 |
| Q-wave MI | 4 (0.1) | 10 (0.3) | 0.398 (0.125, 1.272) | 0.1202 |
| Mortality/Q-wave MI/IDR | 25 (0.6) | 35 (0.9) | 0.711 (0.425, 1.190) | 0.1941 |
| Mortality/Q-wave MI/Stent thrombosis | 18 (0.5) | 24 (0.6) | 0.747 (0.405, 1.379) | 0.3511 |

TABLE 11-continued 48-hour endpoints for ITT, MITT, and Safety Populations.

ITT With STEMI

| | Cangrelor (N = 487) | Clopidogrel (N = 509) | OR (95% CI) | P Value |
|---|---|---|---|---|
| Mortality/MI/IDR | 20 (4.1) | 20 (3.9) | 1.054 (0.560, 1.985) | 0.8703 |
| MI | 16 (3.3) | 9 (1.8) | 1.900 (0.831, 4.341) | 0.1280 |
| IDR | 6 (1.2) | 8 (1.6) | 0.786 (0.271, 2.283) | 0.6584 |
| All-cause mortality | 1 (0.2) | 5 (1.0) | 0.209 (0.024, 1.793) | 0.1534 |
| Stent thrombosis | 4 (0.8) | 4 (0.8) | 1.052 (0.262, 4.321) | 0.9428 |
| Stroke | 0 (0.0) | 1 (0.2) | — | — |
| Q-wave MI | 0 (0.0) | 0 (0.0) | — | — |
| Mortality/Q-wave MI/IDR | 7 (1.5) | 13 (2.6) | 0.560 (0.222, 1.416) | 0.2204 |
| Mortality/Q-wave MI/Stent thrombosis | 5 (1.0) | 9 (1.8) | 0.580 (0.193, 1.743) | 0.3320 |

MITT

| | Cangrelor (N = 4347) | Clopidogrel (N = 4320) | OR (95% CI) | P Value |
|---|---|---|---|---|
| Mortality/MI/IDR | 308 (7.1) | 293 (6.8) | 1.049 (0.889, 1.238) | 0.5709 |
| MI | 292 (6.7) | 264 (6.1) | 1.107 (0.932, 1.315) | 0.2451 |
| IDR | 19 (0.4) | 30 (0.7) | 0.628 (0.353, 1.118) | 0.1140 |
| All-cause mortality | 9 (0.2) | 9 (0.2) | 0.995 (0.394, 2.508) | 0.9910 |
| Stent thrombosis | 11 (0.3) | 15 (0.3) | 0.729 (0.334, 1.588) | 0.4261 |
| Stroke | 6 (0.1) | 7 (0.2) | 0.852 (0.286, 2.538) | 0.7742 |
| Q-wave MI | 4 (0.1) | 10 (0.2) | 0.397 (0.125, 1.268) | 0.1190 |
| Mortality/Q-wave MI/IDR | 30 (0.7) | 45 (1.0) | 0.661 (0.416, 1.051) | 0.0801 |
| Mortality/Q-wave MI/Stent thrombosis | 23 (0.5) | 31 (0.7) | 0.737 (0.429, 1.265) | 0.2681 |

MITT With STEMI

| | Cangrelor (N = 450) | Clopidogrel (N = 449) | OR (95% CI) | P Value |
|---|---|---|---|---|
| Mortality/MI/IDR | 18 (4.0) | 17 (3.8) | 1.064 (0.541, 2.092) | 0.8578 |
| MI | 14 (3.1) | 8 (1.8) | 1.778 (0.739, 4.282) | 0.1991 |
| IDR | 6 (1.3) | 7 (1.6) | 0.857 (0.286, 2.571) | 0.7833 |
| All-cause mortality | 1 (0.2) | 4 (0.9) | 0.249 (0.028, 2.235) | 0.2143 |
| Stent thrombosis | 4 (0.9) | 4 (0.9) | 1.002 (0.249, 4.033) | 0.9975 |
| Stroke | 0 (0.0) | 0 (0.0) | — | — |
| Q-wave MI | 0 (0.0) | 0 (0.0) | — | — |
| Mortality/Q-wave MI/IDR | 7 (1.6) | 11 (2.5) | 0.632 (0.243, 1.645) | 0.3473 |
| Mortality/Q-wave MI/Stent thrombosis | 5 (1.1) | 8 (1.8) | 0.622 (0.202, 1.917) | 0.4084 |

Safety

| | Cangrelor (N = 4374) | Clopidogrel (N = 4365) | OR (95% CI) | P Value |
|---|---|---|---|---|
| Mortality/MI/IDR | 310 (7.1) | 294 (6.7) | 1.058 (0.896, 1.248) | 0.5073 |
| MI | 294 (6.7) | 265 (6.1) | 1.116 (0.940, 1.325) | 0.2091 |
| IDR | 19 (0.4) | 30 (0.7) | 0.631 (0.355, 1.123) | 0.1175 |
| All-cause mortality | 9 (0.2) | 9 (0.2) | 0.999 (0.396, 2.519) | 0.9984 |
| Stent thrombosis | 11 (0.3) | 15 (0.3) | 0.732 (0.336, 1.595) | 0.4326 |
| Stroke | 6 (0.1) | 7 (0.2) | 0.856 (0.288, 2.550) | 0.7803 |
| Q-wave MI | 4 (0.1) | 10 (0.2) | 0.399 (0.125, 1.273) | 0.1207 |
| Mortality/Q-wave MI/IDR | 30 (0.7) | 45 (1.0) | 0.664 (0.417, 1.056) | 0.0834 |
| Mortality/Q-wave MI/Stent thrombosis | 23 (0.5) | 31 (0.7) | 0.740 (0.431, 1.271) | 0.2751 |

Variables are presented as a no. (%) unless otherwise indicated. CI denotes confidence interval; IDR, ischemia-driven revascularization; ITT, intent to treat; MI, myocardial infarction; MITT, modified intent to treat; OR, odds ratio; STEMI, ST-segment elevation myocardial infarction.

A substudy was conducted at 15 sites to evaluate platelet function during infusion and to assess whether the administration of a cangrelor infusion prior to administration of clopidogrel 600 mg has any effect on platelet inhibition by clopidogrel. Patients in the substudy were required to be clopidogrel naïve and could not have received glycoprotein IIb/IIIa inhibition during the procedure. Platelet function parameters were measured using the VerifyNow® P2Y12 Assay (Accumetrics, San Diego, Calif.). Samples were taken before study drug administration, at approximately 2 hours (during cangrelor/placebo infusion), and 10 hours or next day following randomization.

The median baseline P2Y12 reaction units (PRU) from the VerifyNow® P2Y12 assay were 335 in the cangrelor arm (264, 384; n=97) and 329 in the clopidogrel arm (285.5, 376.5; n=100). During the study drug infusion, the median PRU was significantly lower in the cangrelor arm (93.5; 40.0, 173.5; n=64) compared with the clopidogrel arm during the same time period (277; 206.0, 355.0; n=74). At 12-24 hours after discontinuation of the cangrelor infusion, the median PRU was 228 in the cangrelor arm (156.0, 298.0; n=87) and 206 in the clopidogrel arm (135.0, 274.0; n=87).

The percent of individuals achieving less than 20% change in PRU between baseline and greater than 10 h after PCI was higher with cangrelor+clopidogrel (32/84, 38.1%) compared with placebo+clopidogrel (21/83, 25.3%), but this was not statistically significant (difference: 12.79%, 95% CI: −1.18%, 26.77%; p=0.076).

Example 3

Comparison of Cangrelor to Clopidogrel Standard of Care Therapy in Patients Who Require Percutaneous Coronary Intervention The efficacy and safety of cangrelor versus clopidogrel standard of care therapy was examined in patients with atherosclerosis undergoing PCI in a double-blind, placebo-controlled, double-dummy study.

Figure 7:
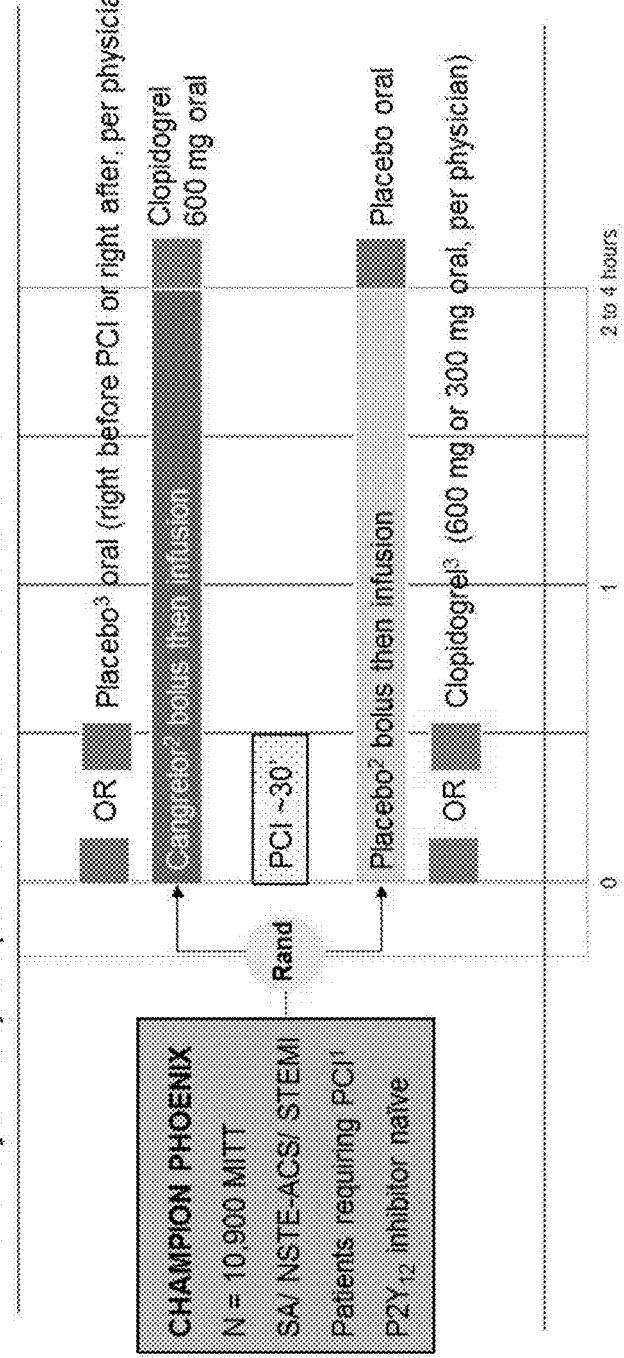
FIG. 7 shows a diagram of the trial design for the study described in Example 3.

A total of 11,145 patients underwent randomization at 153 sites in 12 countries from Sep. 30, 2010 to Oct. 3, 2012. Randomization was performed before PCI with the use of an interactive voice-response or Web-response system, with stratification according to site, baseline status (normal or abnormal, as defined by a combination of biomarker levels, electrocardiographic changes, and symptoms), and intended loading dose of clopidogrel (600 mg or 300 mg). Randomization divided the patients into two groups: the cangrelor group and the clopidogrel group. Patients assigned to the cangrelor group were administered: (i) placebo capsules (before or immediately after PCI to match clopidogrel capsules administered in the clopidogrel group); (ii) a cangrelor bolus (30 μg/kg)/infusion (4 μg/kg/min); and (iii) capsules containing 600 mg of clopidogrel administered at the end of infusion. Patients assigned to the clopidogrel group were administered: (i) clopidogrel capsules (300 mg or 600 mg before or immediately after PCI, with the dose and timing of administration determined at the discretion of the site investigator); (ii) a placebo bolus/infusion (to match the cangrelor bolus/infusion administered in the cangrelor group); and (iii) placebo capsules administered at the end of the infusion (to match the capsules containing 600 mg of clopidogrel administered at the end of the infusion in the cangrelor group). The cangrelor or placebo infusion was administered for at least 2 hours or the duration of the PCI procedure, whichever was longer. A summary of the study design is shown in FIG. 7.

The protocol called for aspirin (75 to 325 mg) to be administered to all patients. The protocol also called for a maintenance dose of clopidogrel (75 mg) to be administered during the first 48 hours after randomization; thereafter, clopidogrel or another $P2Y_{12}$ inhibitor could be administered at the discretion of the investigator, according to local guidelines. The choice of a periprocedural anticoagulant (bivalirudin, unfractionated heparin, low-molecular-weight heparin, or fondaparinux) was also at the discretion of the investigator. Glycoprotein IIb/IIIa inhibitors were allowed only as rescue therapy during PCI to treat new or persistent thrombus formation, slow or no reflow, side-branch compromise, dissection, or distal embolization. The investigator at the site determined the protocol for management of the arterial sheath.

The inclusion criteria for the trial were men or nonpregnant women, 18 years of age or older with coronary atherosclerosis who required PCI for stable angina, a non-ST-segment elevation acute coronary syndrome, or ST-segment elevation myocardial infarction (STEMI). Patients were required to provide written informed consent.

Major exclusion criteria were receipt of a $P2Y_{12}$ inhibitor or abciximab at any time in the 7 days before randomization and receipt of eptifibatide or tirofiban or fibrinolytic therapy in the 12 hours before randomization.

The primary efficacy end point was the composite rate of death from any cause, myocardial infarction, IDR, or stent thrombosis in the 48 hours after randomization in the modified intention-to-treat population (which comprised patients who actually underwent PCI and received the study drug). The protocol specified that if more than 15% of the patients received a 300-mg loading dose of clopidogrel (as compared with a 600-mg dose) at the time of randomization, the primary analysis was to be adjusted for loading dose in addition to baseline status. The key secondary end point was the incidence of stent thrombosis at 48 hours. This end point included definite stent thrombosis, defined according to the criteria of the Academic Research Consortium, or intraprocedural stent thrombosis, which was assessed, with group assignments concealed, at an angiographic core laboratory (Cardiovascular Research Foundation). Intraprocedural stent thrombosis was defined as any new or worsened thrombus related to the stent procedure that was confirmed angiographically. Events of death, myocardial infarction, IDR, and stent thrombosis that occurred during the first 30 days after randomization were adjudicated by the clinical events committee at the Duke Clinical Research Institute. The criteria that the clinical events committee used to define myocardial infarction are provided in Tables 12A and 12B. The study adhered to the universal definition of myocardial infarction for myocardial infarction unrelated to PCI but expanded on the definition of PCI-related myocardial infarction.

TABLE 12A

Baseline status assessment and trigger logic.*

| Baseline Status | Cardiac Markers (Troponin Preferred; use CKMB if not available) | ECG[1] (12 Lead) | Ischemic Symptoms[2] (Angina or equivalent symptoms at rest) |
|---|---|---|---|
| Baseline Normal (No MI at baseline) | | | |
| Stable angina / elective | All samples within 6 hours prior to access sample are normal (1 sample sufficient; samples can be <6 hr apart) | AND: no presumed new changes | AND: no ongoing ACS symptoms or symptoms within 6 hours prior to access site sample |

TABLE 12A-continued

Baseline status assessment and trigger logic.*

| Baseline Status | Cardiac Markers (Troponin Preferred; use CKMB if not available) | ECG[1] (12 Lead) | Ischemic Symptoms[2] (Angina or equivalent symptoms at rest) |
|---|---|---|---|
| NSTE-ACS | 2 normal samples ≥6 hours apart (sample 2 is the access sample) | AND: no presumed new changes | AND: no ongoing ACS symptoms or symptoms within 6 hours prior to access site sample |
| Baseline Abnormal (MI ongoing at baseline) | | | |
| Decreasing & returns to normal | 2 samples ≥6 hours apart with most recent access sample returned to normal | AND: no presumed new ECG changes | AND: no recent symptoms within 6 hours prior to access site sample |
| Decreasing & remains abnormal | 2 samples ≥6 hours apart with most recent access sample fallen at least 20% | AND: no presumed new ECG changes | AND: no recent symptoms within 6 hours prior to access site sample |
| Increasing | Insufficient biomarker data for all other categories | OR: Presumed new changes including STEMI | OR: recent symptoms within 6 hours prior to access site sample |
| Baseline unknown | No samples pre PCI available | | |

*CKMB denotes creatine kinase-myocardial band isoenzyme, ECG denotes electrocardiography, MI denotes myocardial infarction, NSTE-ACS denotes non-ST-segment elevation acute coronary syndrome, and STEMI denotes ST-segment elevation myocardial infarction.
[1]ECG changes: ST segment elevation/depression >0.1 mV (>1 mm) in at least 2 contiguous leads; new LBBB; new Q wave (greater than 0.03 seconds). ECG collection post PCI: within 1 hour after PCI; pre-discharge.
[2]Ischemic symptoms: angina or equivalent symptoms that need to be treated medically or lasting ≥20 min. Ischemic symptoms as determined by the treating physician include but are not limited to weakness, shortness of breath, wheezing, tiredness, fainting, sweating, nausea/vomiting, abdominal pain, back pain, jaw pain, palpitations, fast heartbeat, drug use for chest pain (nitroglycerin, morphine, beta blocker, etc).

TABLE 12B

Definition of PCI-related myocardial infarction.*

| Endpoint Definition | Baseline MI status | Non-biomarker Evidence of Ischemia | Biomarkers post PCI (core lab CKMB[1] mass) |
|---|---|---|---|
| MI | Baseline normal Stable angina/NSTE-ACS | Not required to qualify MI | elevation ≥3x ULN |
| Reinfarction | Baseline decreasing & returns to normal (No intervening event from elevated sample to PCI) | Not required to qualify MI | elevation ≥3x ULN |
| | Baseline decreasing & remains abnormal (No intervening event from elevated sample to PCI) | (1 of 3): Angiographic complications[2] OR Ischemic symptoms[3] OR New ECG changes[4] | AND: Re-elevation of CKMB ≥3x ULN and ≥50% |
| | Baseline abnormal & increasing OR Baseline unknown | (2 of 2): Angiographic complication AND New ECG changes | AND: Re-elevation of CKMB >3x ULN and ≥50% |

*MI denotes myocardial infarction, CKMB denotes creatine kinase-myocardial band isoenzyme, NSTE-ACS denotes non-ST-segment elevation acute coronary syndrome, ULN denotes upper limit of normal, and PCI denotes percutaneous coronary intervention.
[1]CKMB collection post PCI: 6 hourly collection through 24 hours (minimum of 3 samples required). Core lab values take priority; hospital labs may be used if core lab not available (CKMB priority but troponin may be used).
[2]Angiographic evidence of complication (assessed by the angiographic core laboratory):
New onset of vessel closure or compromise defined as TIMI 0/1 flow after baseline TIMI 2/3 flow (also termed acute closure or no reflow); or
TIMI 2 flow after baseline TIMI 3 flow (also termed slow reflow); or
Sustained distal embolization; or
Sustained side-branch closure of a vessel ≥2 mm in diameter; or
Intra-Procedural Thrombotic Event (IPTE): new or worsening thrombus formation at any time during the procedure. The occurrence of IPTE can be a stent related or not stent related complication phenomena or intra-procedural stent thrombosis (IPST) new or worsening thrombus related to the stent or abrupt closure due to thrombosis. Abrupt closure due to non-thrombotic causes, including major dissections, perforation, or other etiologies, will not be considered IPST. If a non-thrombotic cause of abrupt stent closure cannot be definitively determined, the cause will be considered IPST. IPST may present as either acute thrombotic stent closure after a stent was implanted in a patient with a patent vessel beforehand, or new thrombus formation within or adjacent to a stent in a vessel in which thrombus either was not present or had diminished or resolved before the stent was implanted.
[3]Ischemic symptoms: angina or equivalent symptoms that need to be treated medically or lasting ≥20 min. Ischemic symptoms as determined by the treating physician include but are not limited to weakness, shortness of breath, wheezing, tiredness, fainting, sweating, nausea/vomiting, abdominal pain, back pain, jaw pain, palpitations, fast heartbeat, drug use for chest pain (nitroglycerin, morphine, beta blocker, etc.).
[4]ECG changes: ST segment elevation/depression > 0.1 mV (>1 mm) in at least 2 contiguous leads; new LBBB; new Q wave (greater than 0.03 seconds). ECG collection post PCI: within 1 hour after PCI; pre-discharge.

The primary safety end point was severe bleeding not related to coronary-artery bypass grafting, according to the Global Use of Strategies to Open Occluded Coronary Arteries (GUSTO) criteria, at 48 hours. Several other bleeding definitions were also applied.

On the basis of prior studies, it was assumed that the rate of the composite primary end point would be 5.1% in the clopidogrel group and 3.9% in the cangrelor group, representing a 24.5% reduction in the odds ratio with cangrelor. It was estimated that approximately 10,900 patients would need to be enrolled for the study to have 85% power to detect that reduction. A two-sided overall alpha level of 0.05 was used for all analyses. This study had an adaptive design with conditional power calculation and potential for reestimation of the sample size, if necessary, after the interim analysis that was scheduled to be performed after 70% of the patients were enrolled.

The numbers and percentages of patients within each analysis population (modified intention-to-treat, intention-to-treat, and safety) were summarized according to treatment group. The primary efficacy analysis of the rate of the composite end point of death from any cause, myocardial infarction, IDR, or stent thrombosis (with all events adjudicated by the clinical events committee) in the 48 hours after randomization was conducted in the modified intention-to-treat population. The primary safety analysis was conducted in the safety population, which comprised all patients who underwent randomization and received at least one dose of the study drug; patients were classified according to the actual treatment received. All calculations and statistical analyses were performed with the use of SAS software, version 9.2.

Figure 8:
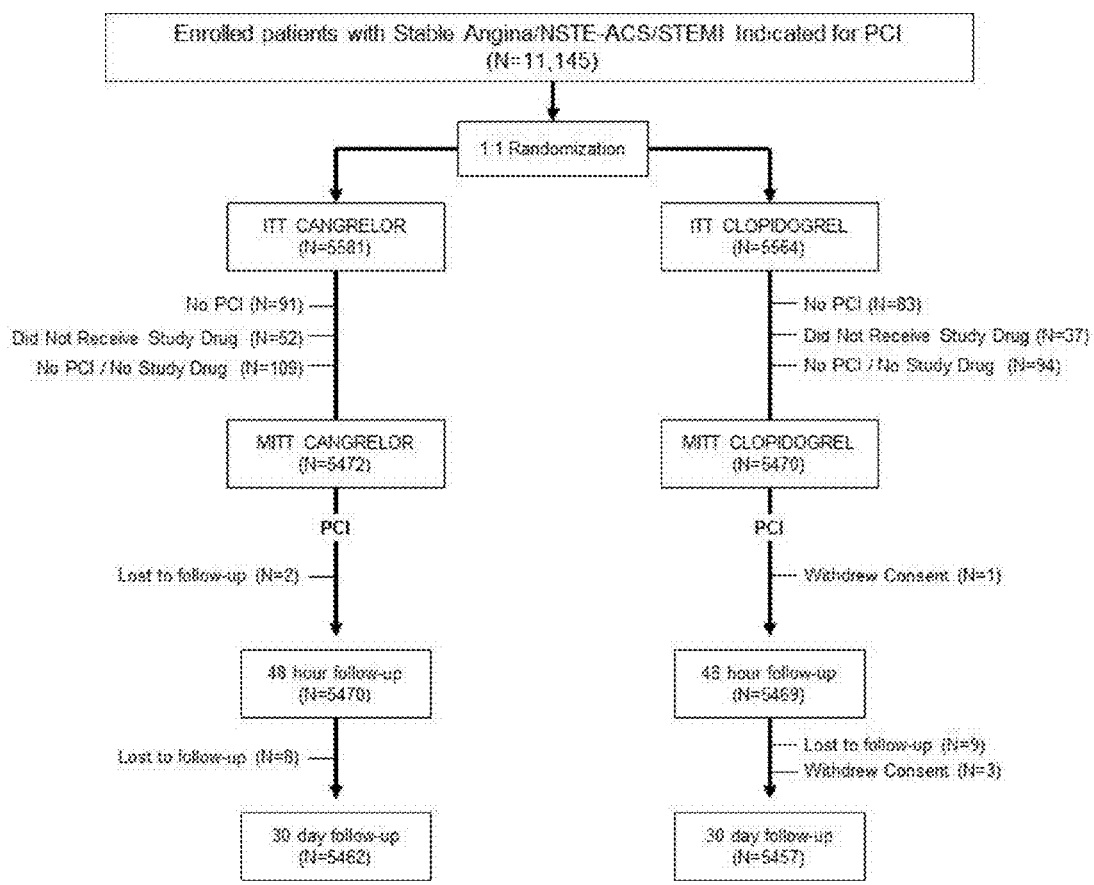
FIG. 8 shows a diagram of the modified intention-to-treat population in the study described in Example 3.

Of the 11,145 patients who underwent randomization, 203 did not undergo PCI or did not receive a study drug; therefore, the modified intention-to-treat population comprised 10,942 patients (FIG. 8). The baseline characteristics were well balanced between the two groups. The characteristics of the patients and the procedure are shown in Tables 13 and 14.

TABLE 13

Baseline characteristics of the patients and characteristics of the procedure in the modified intention-to-treat population, according to treatment group.*

| Characteristic | Cangrelor (N = 5472) | Clopidogrel (N = 5470) |
|---|---|---|
| Age - yr | | |
| Median | 64.0 | 64.0 |
| Interquartile range | 56-72 | 56-72 |
| Female sex - no. (%) | 1558 (28.5) | 1493 (27.3) |
| White race - no./total no. (%)† | 5132/5469 (93.8) | 5120/5463 (93.7) |
| Weight - kg | | |
| Median | 84.0 | 84.0 |
| Interquartile range | 73-95 | 74-96 |
| Diagnosis at presentation - no. (%) | | |
| Stable angina | 3121 (57.0) | 3019 (55.2) |
| NSTE-ACS | 1389 (25.4) | 1421 (26.0) |
| STEMI | 962 (17.6) | 1030 (18.8) |
| Region - no. (%) | | |
| United States | 2048 (37.4) | 2049 (37.5) |
| Other countries | 3424 (62.6) | 3421 (62.5) |
| Cardiac-biomarker status - no./total no. (%)‡ | | |
| Normal | 3520/5467 (64.4) | 3432/5466 (62.8) |
| Abnormal | 1947/5467 (35.6) | 2034/5466 (37.2) |

TABLE 13-continued

Baseline characteristics of the patients and characteristics of the procedure in the modified intention-to-treat population, according to treatment group.*

| Characteristic | Cangrelor (N = 5472) | Clopidogrel (N = 5470) |
|---|---|---|
| Medical history - no./total no (%) | | |
| Diabetes mellitus | 1519/5464 (27.8) | 1536/5463 (28.1) |
| Current smoker | 1504/5339 (28.2) | 1549/5339 (29.0) |
| Hypertension | 4374/5459 (80.1) | 4332/5454 (79.4) |
| Hyperlipidemia | 3363/4851 (69.3) | 3338/4836 (69.0) |
| Prior stroke or TIA | 271/5455 (5.0) | 244/5452 (4.5) |
| Prior myocardial infarction | 1092/5441 (20.1) | 1175/5431 (21.6) |
| PTCA or PCI | 1268/5462 (23.2) | 1333/5461 (24.4) |
| CABG | 578/5466 (10.6) | 500/5464 (9.2) |
| Congestive heart failure | 552/5460 (10.1) | 584/5456 (10.7) |
| Peripheral artery disease | 447/5407 (8.3) | 385/5419 (7.1) |
| Periprocedural medications - no./total no. (%) | | |
| Clopidogrel, 300-mg loading dose | 1405/5472 (25.7) | 1401/5470 (25.6) |
| Clopidogrel, 600-mg loading dose | 4067/5472 (74.3) | 4069/5470 (74.4) |
| Bivalirudin | 1252/5472 (22.9) | 1269/5468 (23.2) |
| Unfractionated heparin | 4272/5472 (78.1) | 4276/5469 (78.2) |
| Low-molecular-weight heparin | 732/5472 (13.4) | 753/5468 (13.8) |
| Fondaparinux | 156/5471 (2.9) | 135/5470 (2.5) |
| Aspirin | 5164/5469 (94.4) | 5148/5465 (94.2) |
| Duration of PCI - min | | |
| Median | 18 | 17 |
| Interquartile range | 10-30 | 10-30 |
| Drug-eluting stent - no. (%) | 3061 (55.9) | 3020 (55.2) |
| Bare-metal stent - no. (%) | 2308 (42.2) | 2344 (42.9) |
| Balloon angioplasty - no. (%) | 292 (5.3) | 273 (5.0) |

*Denominators exclude patients in whom the status was reported as unknown by the study center. There were no significant differences between the two groups, except for a history of coronary-artery bypass grafting (CABG) (P = 0.01), prior myocardial infarction (P = 0.04), and peripheral-artery disease (P = 0.02). NSTE-ACS denotes non-ST-segment elevation acute coronary syndrome, PCI percutaneous coronary intervention, PTCA percutaneous transluminal coronary angioplasty, STEMI ST-segment elevation myocardial infarction, and TIA transient ischemic attack.
†Race was self-reported.
‡Cardiac biomarker status was considered to be abnormal if at least one of the baseline troponin I or T levels, obtained within 72 hours before randomization or after randomization but before initiation of the study drug, was greater than the upper limit of the normal range, as determined by the local laboratory. If the baseline troponin level was not available, the baseline MB fraction of creatine kinase was used.

TABLE 14

Additional baseline and procedural characteristics for the modified intention-to-treat population, according to the treatment group.*

| Characteristic | Cangrelor (N = 5472) | Clopidogrel (N = 5470) |
|---|---|---|
| Age | | |
| ≥65 years | 2645/5472 (48.3) | 2615/5470 (47.8) |
| ≥75 years | 1022/5472 (18.7) | 988/5470 (18.1) |
| Sex, No. (%) | | |
| Male | 3914/5472 (71.5) | 3977/5470 (72.7) |
| Female | 1558/5472 (28.5) | 1493/5470 (27.3) |
| Race, No. (%) | | |
| White | 5132/5469 (93.8) | 5120/5463 (93.7) |
| Asian | 171/5469 (3.1) | 175/5463 (3.2) |
| Black | 149/5469 (2.7) | 146/5463 (2.7) |
| Other | 17/5469 (0.3) | 22/5463 (0.4) |
| Hispanic or Latino, No. (%) | 193/5472 (3.5) | 196/5470 (3.6) |
| Height, cm | 172.0 (165, 178) | 172.0 (165, 178) |
| Diabetes Type, No. (%) | | |
| IDDM | 459/5464 (8.4) | 404/5463 (7.4) |
| Non-IDDM | 1020/5464 (18.7) | 1108/5463 (20.3) |
| Unknown Type | 40/5464 (0.7) | 23/5463 (0.4) |
| Family history of CAD, No. (%) | 2088/5120 (40.8) | 2079/5115 (40.6) |

TABLE 14-continued

Additional baseline and procedural characteristics for the modified intention-to-treat population, according to the treatment group.*

| Characteristic | Cangrelor (N = 5472) | Clopidogrel (N = 5470) |
|---|---|---|
| Catheter Access Site, No. (%) | | |
| Femoral | 4053/5472 (74.1) | 4011/5470 (73.3) |
| Radial | 1410/5472 (25.8) | 1445/5470 (26.4) |
| Brachial | 9/5472 (0.2) | 14/5470 (0.3) |
| Number of vessels treated, index PCI, No. (%) | | |
| 0 | 49/5472 (0.9) | 49/5470 (0.9) |
| 1 | 4545/5472 (83.1) | 4604/5470 (84.2) |
| 2 | 768/5472 (14.0) | 723/5470 (13.2) |
| 3 | 103/5472 (1.9) | 89/5470 (1.6) |
| 4 | 7/5472 (0.1) | 5/5470 (0.1) |

*Denominators exclude patients in whom the status was reported as unknown by the site. There were no significant differences between the two groups, except for type of diabetes (p <0.05). CAD denotes coronary artery disease; IDDM denotes insulin-dependent diabetes mellitus; and MITT denotes modified intent to treat.

The results of the analyses of the efficacy and safety end points at 48 hours after randomization are provided in Tables 15, 16, and 17.

Figure 9A:
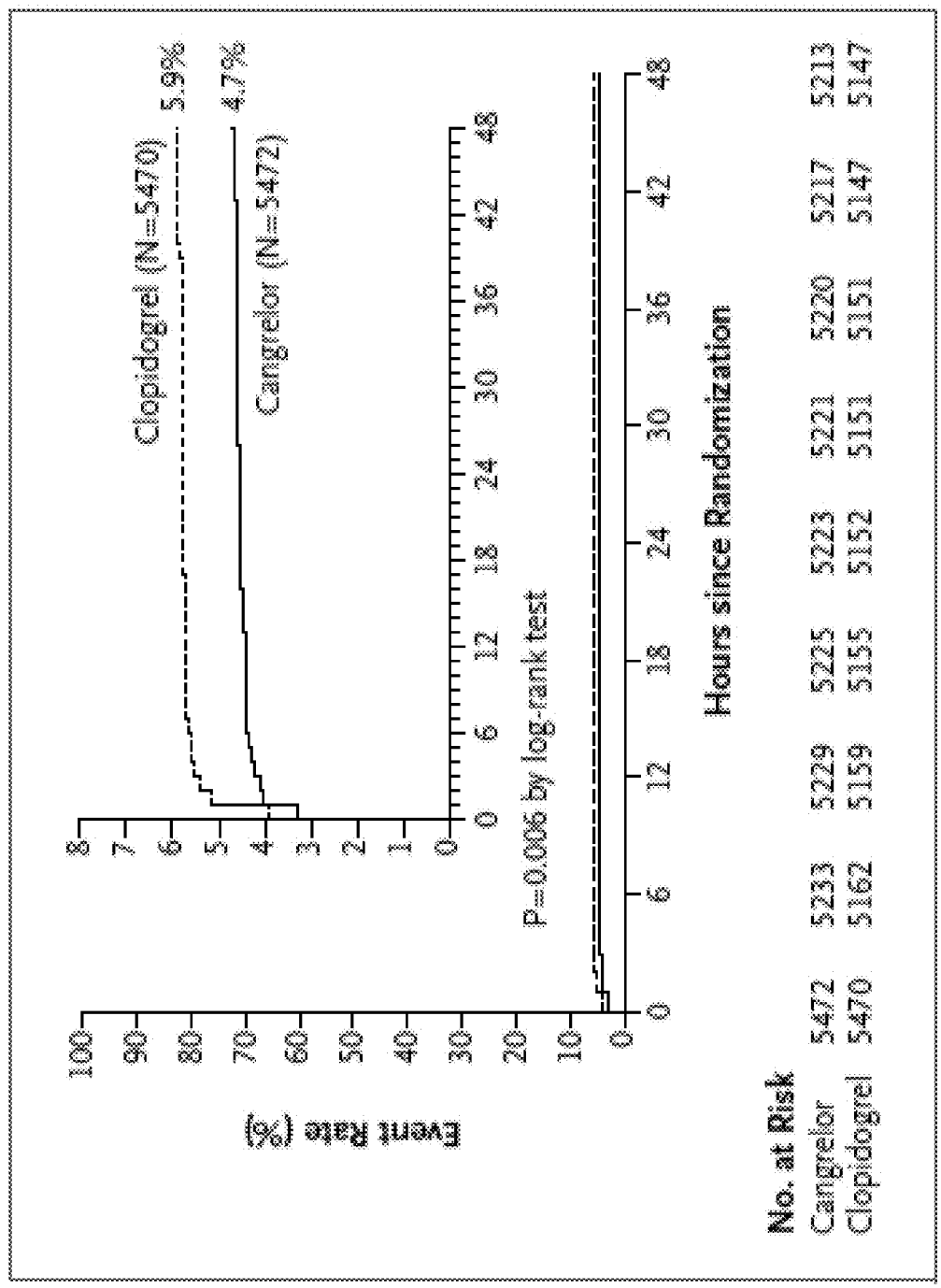
FIGS. 9A and 9B shows landmark analysis of Kaplan Meier curves for the primary endpoint (FIG. 9A) and the key secondary end point of stent thrombosis (FIG. 9B) in the study described in Example 3.

The rate of the primary composite efficacy end point of death from any cause, myocardial infarction, IDR, or stent thrombosis at 48 hours was significantly lower in the cangrelor group than in the clopidogrel group (4.7% vs. 5.9%; odds ratio, 0.78; 95% confidence interval [CI], 0.66 to 0.93; P=0.005), on the basis of the prespecified logistic-regression analysis, which adjusted for baseline status (normal vs. abnormal) and clopidogrel loading dose (600 mg vs. 300 mg) (Table 15). The result of the crude analysis was similar (odds ratio, 0.79; 95% CI, 0.67 to 0.93; P=0.006). FIG. 9A shows the Kaplan-Meier estimates of the time-to-event distributions for the primary end point. The number needed to treat with cangrelor to prevent one primary end-point event is 84 (95% CI, 49 to 285).

Figure 9B:
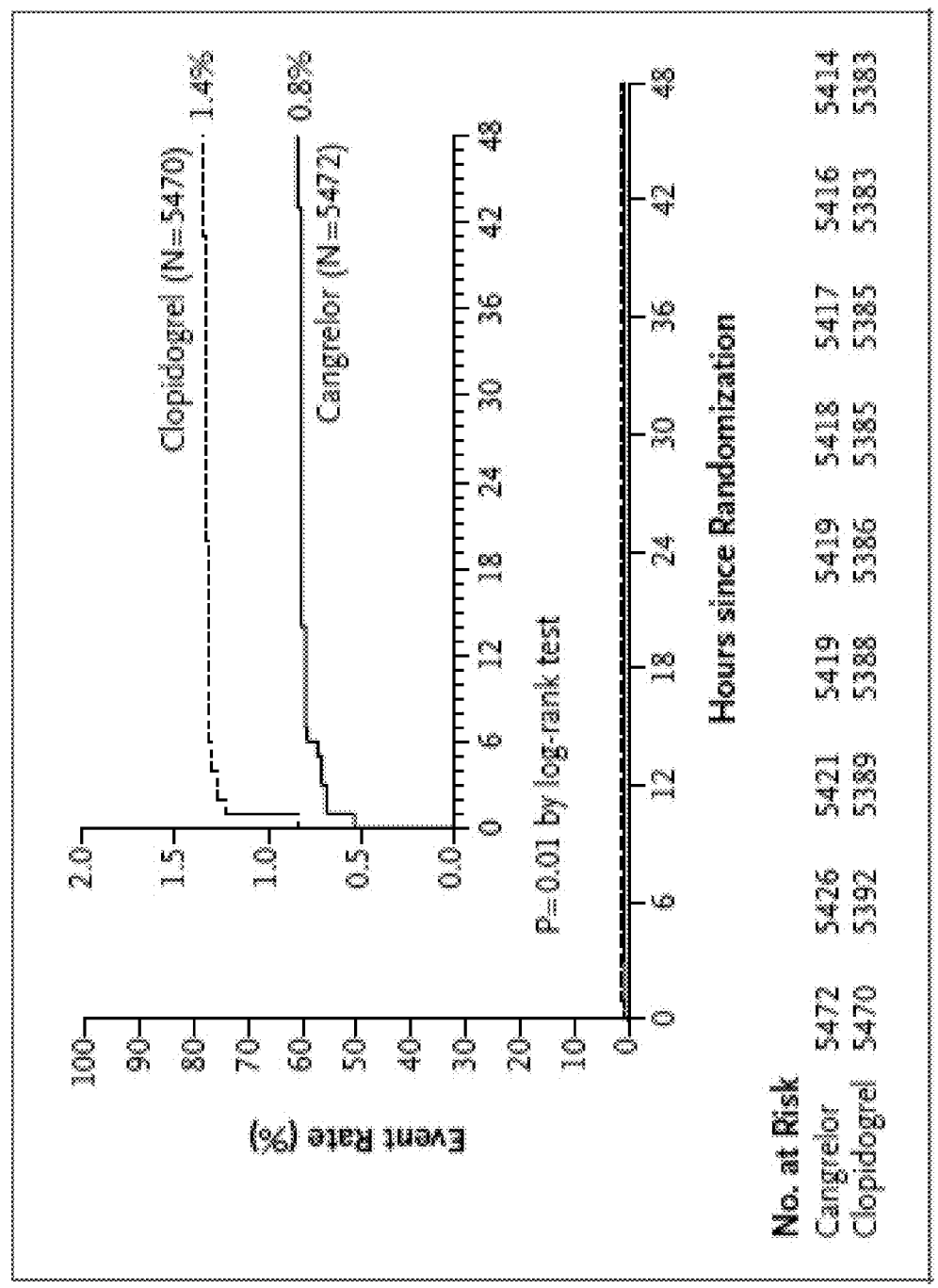

The rate of the key secondary efficacy end point of stent thrombosis at 48 hours was also lower in the cangrelor group than in the clopidogrel group (0.8% vs. 1.4%; odds ratio, 0.62; 95% CI, 0.43 to 0.90; P=0.01) (Table 15). FIG. 9B shows the Kaplan-Meier estimates of the time-to-event distributions for the key secondary end point.

The rate of the primary safety end point, GUSTO-defined severe bleeding, was 0.16% in the cangrelor group as compared with 0.11% in the clopidogrel group (odds ratio, 1.50; 95% CI, 0.53 to 4.22; P=0.44) (Table 15). Bleeding events according to several other bleeding definitions were also examined (Table 17). In a post hoc analysis, the primary efficacy end point and the primary safety end point were combined to provide a composite end point of the net rate of adverse clinical events, which was 4.8% in the cangrelor group as compared with 6.0% in the clopidogrel group (odds ratio, 0.80; 95% CI, 0.68 to 0.94; P=0.008) (Table 15).

TABLE 15

Efficacy and safety end points at 48 hours after randomization.*

| End Point | Cangrelor | Clopidogrel | Odds Ratio (95% CI) | P Value |
|---|---|---|---|---|
| | number/total number (percent) | | | |
| Efficacy | | | | |
| No. of Patients in modified intention-to-treat population | 5472 | 5470 | | |
| Primary end point: death from any cause, myocardial infarction, ischemia-driven revascularization, or stent thrombosis† | 257/5470 (4.7) | 322/5469 (5.9) | 0.78 (0.66-0.93) | 0.005 |
| Key secondary end point: stent thrombosis | 46/5470 (0.8) | 74/5469 (1.4) | 0.62 (0.43-0.90) | 0.01 |
| Myocardial infarction | 207/5470 (3.8) | 255/5469 (4.7) | 0.80 (0.67-0.97) | 0.02 |
| Q-wave myocardial infarction | 11/5470 (0.2) | 18/5469 (0.3) | 0.61 (0.29-1.29) | 0.19 |
| Ischemia-driven revascularization | 28/5470 (0.5) | 38/5469 (0.7) | 0.74 (0.45-1.20) | 0.22 |
| Death from any cause | 18/5470 (0.3) | 18/5469 (0.3) | 1.00 (0.52-1.92) | >0.999 |
| Death from cardiovascular causes | 18/5470 (0.3) | 18/5469 (0.3) | 1.00 (0.52-1.92) | >0.999 |
| Death or stent thrombosis | 59/5470 (1.1) | 87/5469 (1.6) | 0.67 (0.48-0.94) | 0.02 |
| Death, Q-wave myocardial infarction, or ischemia-driven revascularization | 49/5470 (0.9) | 64/5469 (1.2) | 0.76 (0.53-1.11) | 0.16 |
| Safety: non-CABG-related bleeding | | | | |
| No. of patients in safety population | 5529 | 5527 | | |
| GUSTO-defined bleeding | | | | |
| Primary safety end point: severe or life-threatening bleeding | 9/5529 (0.2) | 6/5527 (0.1) | 1.50 (0.53-4.22) | 0.44 |
| Moderate bleeding | 22/5529 (0.4) | 13/5527 (0.2) | 1.69 (0.85-3.37) | 0.13 |
| Severe or moderate bleeding | 31/5529 (0.6) | 19/5527 (0.3) | 1.63 (0.92-2.90) | 0.09 |
| TIMI-defined bleeding | | | | |
| Major bleeding | 5/5529 (0.1) | 5/5527 (0.1) | 1.00 (0.29)-3.45) | >0.999 |
| Minor bleeding | 9/5529 (0.2) | 3/5527 (0.1) | 3.00 (0.81-11.10) | 0.08 |
| Major or minor bleeding | 14/5529 (0.3) | 8/5527 (0.3) | 1.75 (0.73-4.18) | 0.20 |
| Any blood transfusion | 25/5529 (0.5) | 16/5527 (0.3) | 1.56 (0.83-2.93) | 0.16 |

TABLE 15-continued

Efficacy and safety end points at 48 hours after randomization.*

| End Point | Cangrelor | Clopidogrel | Odds Ratio (95% CI) | P Value |
|---|---|---|---|---|
| Efficacy and safety: net adverse clinical events‡ | | | | |
| Death, myocardial infarction, ischemia-driven revascularization, stent thrombosis, or GUSTO-defined severe bleeding | 264/5470 (4.8) | 327/5469 (6.0) | 0.80 (0.68-0.94) | 0.008 |

*GUSTO denotes Global Use of Strategies to Open Occluded Coronary Arteries, and TIMI denotes Thrombolysis in Myocardial Infarction.
†The prespecified logistic-regression analysis was adjusted for baseline status (normal vs. abnormal) and clopidogrel loading dose (600 mg vs. 300 mg.)
‡The primary efficacy and primary safety end points were combined to provide a composite end point of net adverse clinical events in the modified intention-to-treat population.

TABLE 16

Additional efficacy endpoints at 48 hours after randomization for the modified intention-to-treat population.*

| End Point | Cangrelor (N = 5472) | Clopidogrel (N = 5470) | OR (95% CI) | P Value |
|---|---|---|---|---|
| Death/MI | 220/5470 (4.0) | 272/5469 (5.0) | 0.80 (0.67, 0.96) | 0.02 |
| Death/MI/ST | 249/5470 (4.6) | 312/5469 (5.7) | 0.79 (0.66, 0.94) | 0.006 |
| Death/MI/IDR | 230/5470 (4.2) | 286/5469 (5.2) | 0.80 (0.67, 0.95) | 0.01 |
| Death/MI/IDR/Definite ST | 230/5470 (4.2) | 286/5469 (5.2) | 0.80 (0.67, 0.95) | 0.01 |
| Death/MI/Definite ST | 222/5470 (4.1) | 276/5469 (5.0) | 0.80 (0.66, 0.95) | 0.01 |
| Definite ST | 12/5470 (0.2) | 22/5469 (0.4) | 0.54 (0.27, 1.10) | 0.09 |

*MI denotes myocardial infarction, ST denotes stent thrombosis, and IDR denotes ishemia-driven revascularization.

TABLE 17

Additional efficacy and safety endpoints at 48 hours after randomization.*

| | Intention-to-Treat (ITT) | | | |
|---|---|---|---|---|
| Ischemic | Cangrelor (N = 5581) | Clopidogrel (N = 5564) | OR (95% CI) | P Value |
| Death/MI/IDR/ST | 260/5573 (4.7) | 325/5561 (5.8) | 0.79 (0.67, 0.93) | 0.005 |
| Stent thrombosis | 46/5573 (0.8) | 74/5561 (1.3) | 0.62 (0.43, 0.89) | 0.01 |
| MI | 207/5573 (3.7) | 255/5561 (4.6) | 0.80 (0.67, 0.97) | 0.02 |
| Q-wave MI | 11/5573 (0.2) | 18/5561 (0.3) | 0.61 (0.29, 1.29) | 0.19 |
| IDR | 29/5573 (0.5) | 38/5561 (0.7) | 0.76 (0.47, 1.23) | 0.27 |
| Death | 20/5573 (0.4) | 21/5561 (0.4) | 0.95 (0.51, 1.75) | 0.87 |
| CV Death | 20/5573 (0.4) | 21/5561 (0.4) | 0.95 (0.51, 1.75) | 0.87 |
| Death/ST | 61/5573 (1.1) | 90/5561 (1.6) | 0.67 (0.49, 0.93) | 0.02 |
| Death/MI | 222/5573 (4.0) | 275/5561 (5.0) | 0.80 (0.67, 0.96) | 0.01 |
| Death/MI/ST | 251/5573 (4.5) | 315/5561 (5.7) | 0.79 (0.66, 0.93) | 0.005 |
| Death/MI/IDR | 233/5573 (4.2) | 289/5561 (5.2) | 0.80 (0.67, 0.95) | 0.01 |
| Death/Q-wave MI/IDR | 52/5573 (0.9) | 67/5561 (1.2) | 0.77 (0.54, 1.11) | 0.16 |
| Death/MI/IDR/ST/GUSTO Severe Bleeding (Net Adverse Clinical Events, NACE) | 267/5573 (4.8) | 330/5561 (5.9) | 0.80 (0.68, 0.94) | 0.007 |
| | Safety | | | |
| Non-CABG Related Bleeding | Cangrelor (N = 5529) | Clopidogrel (N = 5527) | OR (95% CI) | P Value |
| ACUITY criteria | | | | |
| Major bleeding | 235/5529 (4.3) | 139/5527 (2.5) | 1.72 (1.39, 2.13) | <0.001 |
| Major without ≥ 5 cm hematoma | 42/5529 (0.8) | 26/5527 (0.5) | 1.62 (0.99, 2.64) | 0.05 |
| Minor bleeding | 653/5529 (11.8) | 475/5527 (8.6) | 1.42 (1.26, 1.61) | <0.001 |
| BARC criteria* | | | | |
| Type 3 | 22/5529 (0.4) | 13/5527 (0.2) | 1.69 (0.85, 3.37) | 0.13 |
| Type 3a | 11/5529 (0.2) | 4/5527 (0.1) | 2.75 (0.88, 8.65) | 0.07 |

TABLE 17-continued

Additional efficacy and safety endpoints at 48 hours after randomization.*

| | | | | |
|---|---|---|---|---|
| Type 3b | 9/5529 (0.2) | 8/5527 (0.1) | 1.12 (0.43, 2.92) | 0.81 |
| Type 3c | 2/5529 (0.0) | 1/5527 (0.0) | 2.00 (0.18, 22.06) | 0.56 |

*MI denotes myocardial infarction, ST denotes stent thrombosis, and IDR denotes ischemia-driven revascularization, CV denotes cardiovascular, GUSTO denotes global use of Strategies to Open Occluded Coronary Arteries, ACUITY denotes Acute Catheterization and Urgent Intervention Triage Strategy trial, and BARC denotes Bleeding Academic Research Consortium.

The rate of intraprocedural stent thrombosis was lower in the cangrelor group than in the clopidogrel group (0.6% vs. 1.0%; odds ratio, 0.65; 95% CI, 0.42 to 0.99; P=0.04). The use of rescue therapy with a glycoprotein IIb/IIIa inhibitor was 2.3% with cangrelor as compared with 3.5% with clopidogrel (odds ratio, 0.65; 95% CI, 0.52 to 0.82; P<0.001). The rate of procedural complications was lower with cangrelor than with clopidogrel (3.4% vs. 4.5%; odds ratio, 0.74; 95% CI, 0.61 to 0.90; P=0.002).

At 30 days, the rate of the composite efficacy end point remained significantly lower in the cangrelor group than in the clopidogrel group (6.0% vs. 7.0%; odds ratio, 0.85; 95% CI, 0.73 to 0.99; P=0.03); the relative reduction in stent thrombosis also persisted (1.3% vs. 1.9%; odds ratio, 0.68; 95% CI, 0.50 to 0.92; P=0.01) (Table 18).

TABLE 18

Efficacy outcomes at 30 days after randomization.

| End Points | Cangrelor | Clopidogrel | Odds Ratio (95% CI) | P Value |
|---|---|---|---|---|
| | number/total number (percent) | | | |
| No. of Patients in modified intention-to-treat population | 5472 | 5470 | | |
| Death from any cause, myocardial infarction, ischemia-driven revascularization, or stent thrombosis† | 326/5462 (6.0) | 380/5457 (7.0) | 0.85 (0.73-0.99) | 0.03 |
| Stent thrombosis | 71/5462 (1.3) | 104/5457 (1.9) | 0.68 (0.50-0.92) | 0.01 |
| Myocardial infarction | 225/5462 (4.1) | 272/5457 (5.0) | 0.82 (0.68-0.98) | 0.03 |
| Q-wave myocardial infarction | 14/5462 (0.3) | 22/5457 (0.4) | 0.63 (0.32-1.24) | 0.18 |
| Ischemia-driven revascularization | 56/5462 (1.0) | 66/5457 (1.2) | 0.85 (0.59-1.21) | 0.36 |
| Death from any cause | 60/5462 (1.1) | 55/5457 (1.0) | 1.09 (0.76-1.58) | 0.64 |
| Death from cardiovascular causes | 48/5462 (0.9) | 46/5457 (0.8) | 1.04 (0.69-1.57) | 0.84 |

†The prespecified logistic-regression analysis was for baseline biomarker status (normal vs. abnormal) and clopidogrel loading dose (600-mg vs. 300-mg).

The rate of adverse events related to treatment was similar in the cangrelor and clopidogrel groups (20.2% and 19.1%, respectively; P=0.13); 0.5% of these adverse events in the cangrelor group and 0.4% of those in the clopidogrel group led to discontinuation of the study drug (P=0.21). There were significantly more cases of transient dyspnea with cangrelor than with clopidogrel (1.2% vs. 0.3%, P<0.001) (Table 19).

TABLE 19

Statistically significant treatment emergent adverse events at 48 hours after randomization (safety population).

| System Organ Class Preferred Term | Cangrelor (N = 5529) | Clopidogrel (N = 5527) | Chi-square P value | Fisher exact P value |
|---|---|---|---|---|
| Psychiatric disorders | | | | |
| Agitation | 11/5529 (0.2) | 3/5527 (0.1) | 0.03 | 0.06 |
| Gastrointestinal disorders | | | | |
| Diarrhea | 15/5529 (0.3) | 6/5527 (0.1) | 0.05 | 0.08 |
| General disorders and administration site conditions | | | | |
| Chest Pain | 55/5529 (1.0) | 93/5527 (1.7) | 0.002 | 0.002 |
| Respiratory, thoracic, and mediastinal disorders | | | | |
| Dyspnea | 64/5529 (1.2) | 18/5527 (0.3) | <0.001 | <0.001 |

TABLE 19-continued

Statistically significant treatment emergent adverse events at 48 hours after randomization (safety population).

| System Organ Class<br>Preferred Term | Cangrelor<br>(N = 5529) | Clopidogrel<br>(N = 5527) | Chi-square<br>P value | Fisher<br>exact<br>P value |
|---|---|---|---|---|
| Injury, poisoning, and procedural complications | | | | |
| Procedural Pain | 4/5529 (0.1) | 12/5527 (0.2) | 0.05 | 0.05 |

P values not adjusted for multiple comparisons.

Figure 10:
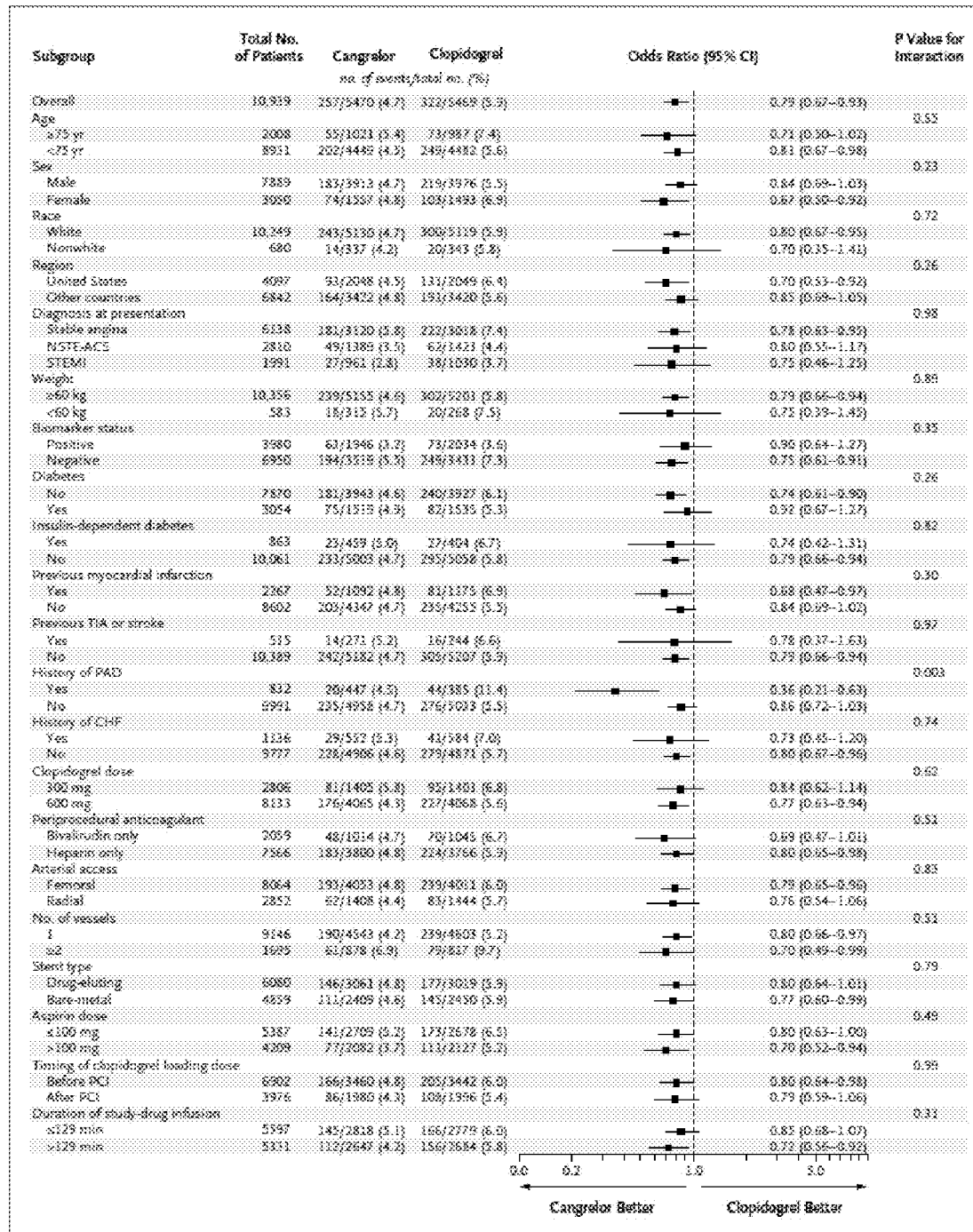
FIG. 10 shows odds ratio plots of the subgroup analysis of the primary efficacy end point in the study described in Example 3.

The reduction in the primary efficacy end point with cangrelor was consistent across multiple subgroups, with no significant interactions with baseline variables except for status with respect to a history of peripheral-artery disease. The benefit with cangrelor was similar among patients presenting with STEMI, those presenting with non-ST-segment elevation acute coronary syndrome, and those presenting with stable angina. There was no heterogeneity of treatment effect between patients in the United States and those in other countries (P=0.26) (FIG. 10).

According to the protocol, patients received a loading dose of clopidogrel or placebo after their coronary anatomy was delineated. The majority of patients received the loading dose before PCI was started (63.4%). The rest of the patients received the loading dose in the catheterization laboratory before PCI was completed (6.4%), within 1 hour after PCI was completed (30.1%), or more than 1 hour after PCI was completed (0.1%). There was no significant difference in the effect of cangrelor on the primary end point between patients who received the loading dose immediately before PCI (odds ratio, 0.80; 95% CI, 0.64 to 0.98) and those who received it during or after PCI (odds ratio, 0.79; 95% CI, 0.59 to 1.06) (P=0.99 for interaction). Similarly, there was no significant difference in the effect of cangrelor on the primary end point between patients who received a 600-mg loading dose of clopidogrel (74.4% of the population) and those who received a 300-mg loading dose (25.6% of the population):the odds ratio for the primary end point with cangrelor was 0.77 (95% CI, 0.63 to 0.94) with the 600-mg loading dose and 0.84 (95% CI, 0.62 to 1.14) with the 300-mg loading dose (P=0.62 for interaction). The protocol required at least 2 hours of study-drug infusion; the median duration of infusion in the cangrelor group was 129 minutes (interquartile range, 120 to 146); the duration of infusion was similar in the clopidogrel group (in which patients received a placebo infusion). A subgroup analysis showed a similar effect of cangrelor among patients who received the infusion for 129 minutes or less (odds ratio, 0.85; 95% CI, 0.68 to 1.07) and those who received the infusion for more than 129 minutes (odds ratio, 0.72; 95% CI, 0.56 to 0.92) (P=0.31 for interaction) (FIG. 10).

Figure 11:
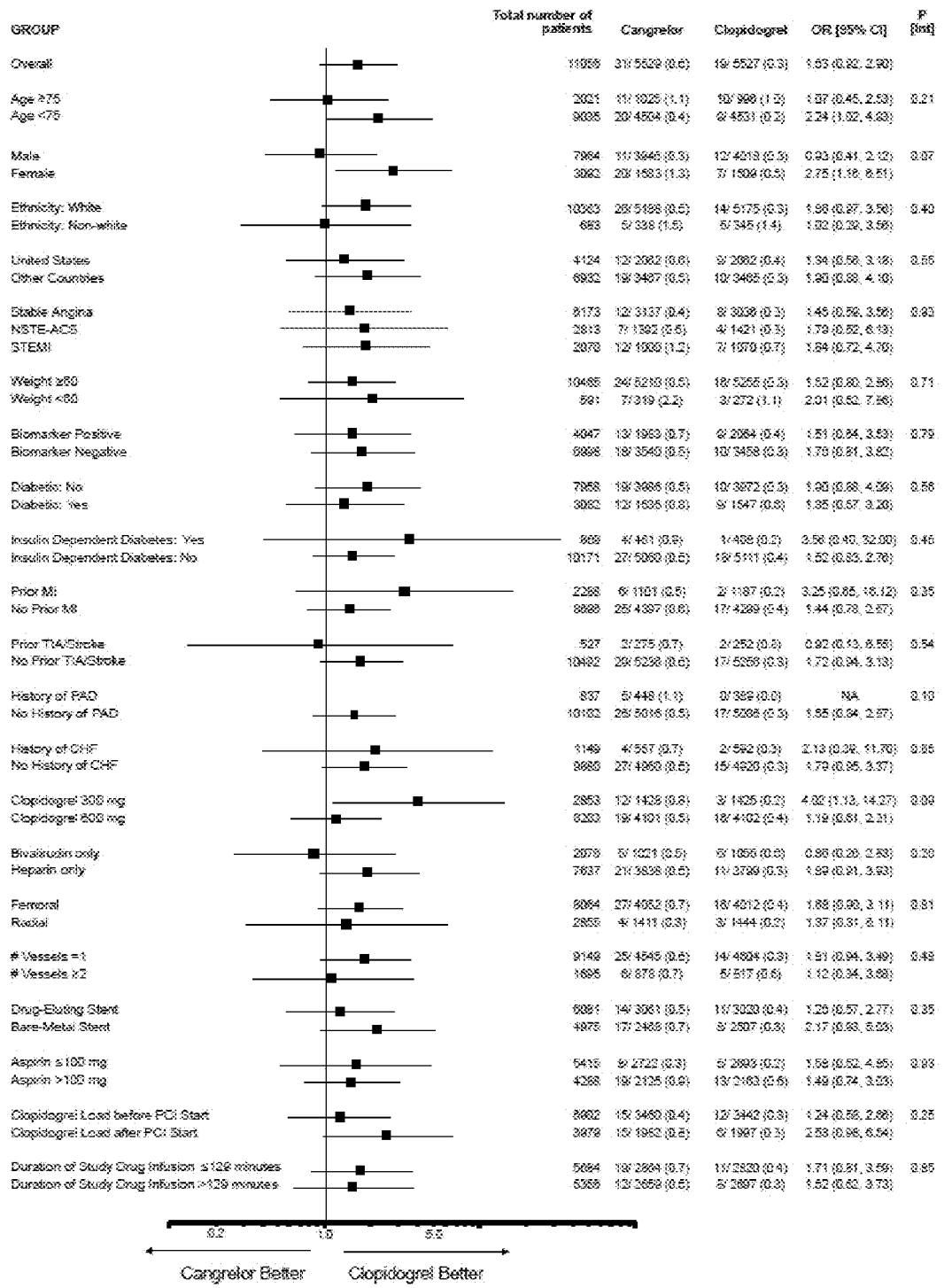
FIG. 11 shows a diagram of the subgroup analysis of Global Use of Strategies to Open Occluded Coronary Arteries (GUSTO) severe or moderate bleeding in the study described in Example 3.

Since the rate of the primary safety end point, GUSTO-defined severe bleeding, was very low, severe bleeding according to GUSTO criteria was combined with moderate bleeding to provide a larger number of events for an analysis of potential subgroup interactions. There were no interactions at P<0.05 (FIG. 11).

As compared with clopidogrel administered immediately before or after PCI, intravenous ADP-receptor blockade with cangrelor significantly reduced the rate of periprocedural complications of PCI, including stent thrombosis. A reduction in the rate of acute periprocedural myocardial infarction accounted for most of the benefit. The odds of an ischemic event were 22% lower with cangrelor than with clopidogrel, and this benefit was not accompanied by a significant increase in severe bleeding or in the need for transfusions. In addition, the odds of stent thrombosis were 38% lower with cangrelor than with clopidogrel. The use of cangrelor resulted in a reduction in ischemic complications across the full spectrum of patients undergoing contemporary PCI, with a consistent benefit in major subgroups.

Example 1 and Example 2 suggested a clinical benefit of cangrelor, including a significant reduction in the secondary end point of stent thrombosis. However, the rate of the primary end point was not reduced in the previous examples, probably because the definition of periprocedural myocardial infarction in those studies did not allow discrimination of reinfarction in patients presenting for PCI soon after admission with a biomarker-positive acute coronary syndrome. In the trial described in Example 3, the definition of periprocedural myocardial infarction required careful assessment of patients' baseline biomarker status. In addition, the use of an angiographic core laboratory allowed objective determination of intraprocedural complications. Table 20 lists the differences between the trials described in Example 1/Example 2 and the trial described in Example 3.

TABLE 20

Differences between the study of Example 3 and the studies of Examples 1 and 2.*†

| | Examples 1 and 2 | Example 3 |
|---|---|---|
| Patient population | 70% Troponin (Tn) elevated at baseline<br>Clopidogrel maintenance (PCI only)<br>PCI required with following:<br>STEMI: safety only (PCI)<br>NSTEMI: Tn elevated<br>Unstable angina: ECG changes and pain and age/diabetes<br>Stable angina: capped (15%) | Assumed 35% Tn elevated at baseline<br>$P2Y_{12}$ inhibitor naive<br>PCI required (Stable angina, NSTE-ACS, STEMI) |
| Comparator | 600 mg clopidogrel | 300 mg or 600 mg (per hospital standard of care) |
| End point | Primary: Death/MI/IDR at 48hr | Primary: Death/MI/IDR/ST at 48hr<br>Key Secondary: ST at 48hr |

TABLE 20-continued

Differences between the study of Example 3 and the studies of Examples 1 and 2.*†

| | Examples 1 and 2 | Example 3 |
|---|---|---|
| Myocardial infarction definition | Not UDMI: reliance on cardiac markers alone to define PCI MI<br>1 baseline sample<br>Biomarker normal at baseline: MI defined as CKMB ≥ 3× ULN post PCI<br>Biomarker elevated at baseline: elevation in CKMB ≥ 3× ULN and 50% increase from baseline sample or ECG changes | UDMI implemented: reliance on cardiac markers and other evidence of ischemia to define PCI MI<br>2 baseline samples at least 6 hours apart required in NSTE-ACS patients to confirm resolving MI at baseline<br>Baseline normal patients: MI defined as CKMB ≥ 3 × ULN post PCI<br>Baseline abnormal patients were classified into MI increasing or decreasing at baseline:<br>Increasing: re-elevation in CKMB post PCI (≥ 3 × ULN and 50% increase from baseline) + additional evidence of ischemia (2 of 2): ECG changes AND angiographic evidence<br>Decreasing: re-elevation in CKMB post PCI (≥ 3 × ULN and 50% increase from baseline) + additional evidence of ischemia (1 of 3): ischemic symptoms, ECG changes or angiographic evidence |
| Stent thrombosis definition | Non-standard definition in IDR patients but confirmed by CEC using angiographic source data | ARC definition in patients<br>IPST (Intra-procedural stent thrombosis) = any procedural new or worsened thrombus related to the stent based on angiographic evidence |
| Statistics | Event rate placebo: 7.7%;<br>Effect size: 22.5-25% | Assumed Event rate placebo: 5.1%;<br>Assumed Effect size: 24.5% |

*PCI denotes percutaneous coronary intervention, STEMI denotes ST-segment elevation myocardial infarction, NSTHMI denotes non-ST-elevated myocardial infarction, ECG denotes denotes electrocardiography, NSTE-ACS denotes non ST-segment elevation acute coronary syndrome, MI denotes myocardial infarction, IDR denotes ischemia-driven revascularization, ST denotes stent thrombosis, UDMI denotes universal definition of myocardial infarction, CKMB denotes creatine kinase-myocardial band isoenzyme, and ULN denotes upper limit of normal.
†Bhatt DL, et al. N Engl J Med 2009;361 2330-41.
Harrington RA, et al. N Engl J Med 2009;361 2318-29
White HD, Am Heart J 2012; 163:182-190.e4
Thygesen, J Am Coll Cardiol 2007:50:2173-95.

Example 4

Pharmacodynamic Effects During the Transition from Cangrelor to Ticagrelor and from Ticagrelor to Cangrelor The objective of this study was to determine whether pharmacodynamic effects of cangrelor would be maintained if ticagrelor was given during infusion of cangrelor and whether previous treatment with ticagrelor altered pharmacodynamic effects of cangrelor.

Methods

The study involved 12 patients who met the criteria of being 18-75 years of age, having coronary artery disease (CAD) documented by a previous MI or coronary revascularization, and taking 81 mg of aspirin daily. Exclusion criterion included an acute coronary syndrome within the past 12 months, treatment with an anticoagulant or antiplatelet agent other than aspirin, a history of a bleeding diathesis, anemia (hematocrit <35%), severe renal insufficiency (creatinine clearance less than 30 ml/min), and moderate or severe hepatic insufficiency. Prohibited concomitant medications included strong and potent CYP3A inhibitors, simvastatin and lovastatin at doses more than 40 mg/day, omeprazole or esomeprazole, and digoxin. Use of non-steroidal anti-inflammatory agents was discouraged during study participation but not prohibited.

Each patient was administered a 30 µg/kg bolus of cangrelor followed immediately by a 2 hr infusion at a rate of 4.0 µg/kg/min. A loading dose of ticagrelor (180 mg) was given after 0.5 hr or 1.25 hr (n=6 for each). Blood for pharmacodynamic platelet function studies was taken after 0.5 or 1.25 hr (corresponding to the time of ticagrelor load, n=6 for each), and then at 1.75, 2, 2.25, 2.5, 2.75, 3, 4, and 5.25 hr. Patients were assigned randomly to receive either 6 (n=6) or 7 (n=6) doses of ticagrelor to be taken every 12 hours following the discontinuation of the infusion of cangrelor. On study day 5, each patient was administered a 30 µg/kg bolus of cangrelor followed immediately by a 2 hr infusion at a rate of 4.0 µg/kg/min. Blood for pharmacodynamic assessment was taken after 1 and 2 hr. Adverse events were queried throughout study participation that ended with a telephone interview performed on study day 10-12.

Pharmacodynamic assessment included light transmission aggregometry (LTA), VerifyNow® P2Y12 assay, vasodilator-stimulated phosphoprotein (VASP) index, and platelet activation measured with the use of flow cytometry. Assessment of LTA, VerifyNow®, and platelet activation with the use of flow cytometry was performed within 30 min of blood being taken. In the case of flow cytometry, samples were processed to fixation and then batched for analysis. For VASP, index samples were batched and processed as recommended by the vendor within 2 h of blood being taken. This approach limited the time from fixation of VASP index to flow analysis to less than 1 h.

LTA induced by 5 µM and 20 µM adenosine diphosphate (ADP) was quantified ex vivo (i.e. in non-adjusted platelet rich plasma). Platelet-poor plasma was set as 100% aggregation, and both maximal (peak) and terminal (at 300 s) aggregation were measured with a PAP4 aggregometer (BioData, Horsham, Pa.). VerifyNow® P2Y12 assay (Accumetrics Inc, San Diego, Calif.) that measures the effects of drugs on the $P2Y_{12}$ receptor by activating platelets with prostaglandin El in addition to ADP was used in accordance with the instructions provided by the manufacturer. Platelet reactivity was expressed in P2Y12 reaction units (PRU). Activation of platelets was identified with the use of flow cytometry as previously described.[17]. And to determine the VASP index, a com mercially available kit (Diagnostica Stago, Inc, Parsippany NJ) was used.

[17] Schneider D J, Sobel B E. Streamlining the design of promising clinical trials: in-vitro testing of antithrombotic regimens and multiple agonists of platelet activation. Coron Artery Dis. 2009; 20:175-8.

Results

The clinical characteristics of the patients are shown in Table 21.

TABLE 21

| Clinical Characteristics. | |
|---|---|
| | n/N (%) All Patients (N = 12) |
| Age | 66.4 ± 5.7 |
| Male | 12 (100) |
| Diabetes Mellitus | 2 (16.7) |
| Current smoker within past 30 days | 1 (8.3) |
| Hypertension | 10 (83.3) |
| Hyperlipidemia | 12 (100.0) |
| Cerebrovascular event | 0 |
| Family history of coronary artery disease | 4 (3.3) |
| Previous MI | 5 (41.7) |
| Previous PCI | 9 (75.0) |
| Previous CABG | 5 (41.7) |
| Heart failure | 0 |
| Peripheral artery disease | 0 |
| Treatment with | |
| Beta blocker | 11 (91.7) |
| ACEI/ARB | 8 (66.7) |
| Ca Channel Blocker | 3 (25) |
| Nitrate | 0 |
| Statin | 12 (100) |

Figure 12:
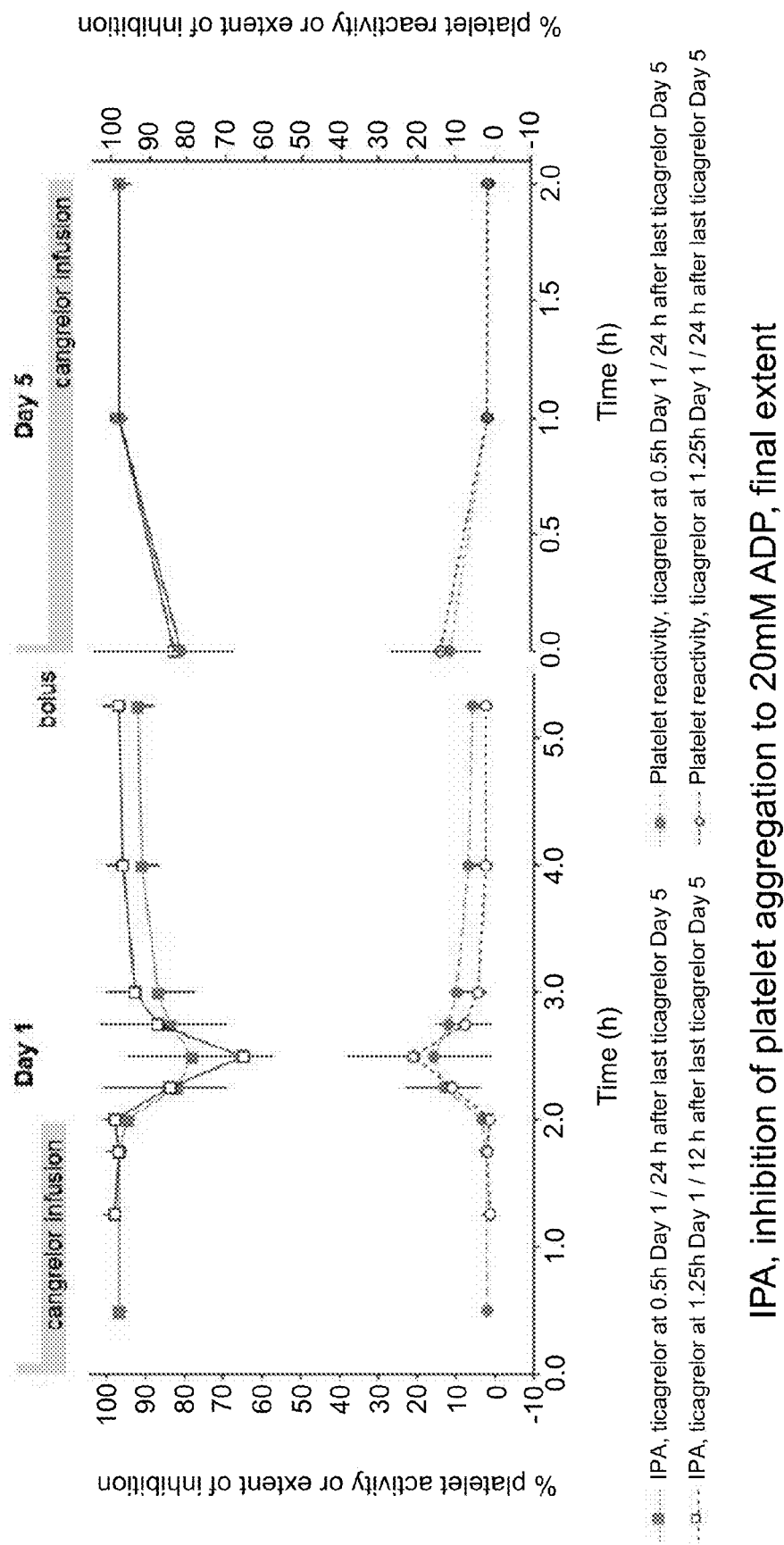
FIG. 12 shows final aggregation of platelets (LTA) induced by 20 μM adenosine diphosphate (ADP) in patients administered with 180 mg of ticagrelor during (at 0.5 hr or 1.25 hr) or after intravenous infusion with cangrelor.
Figure 13:
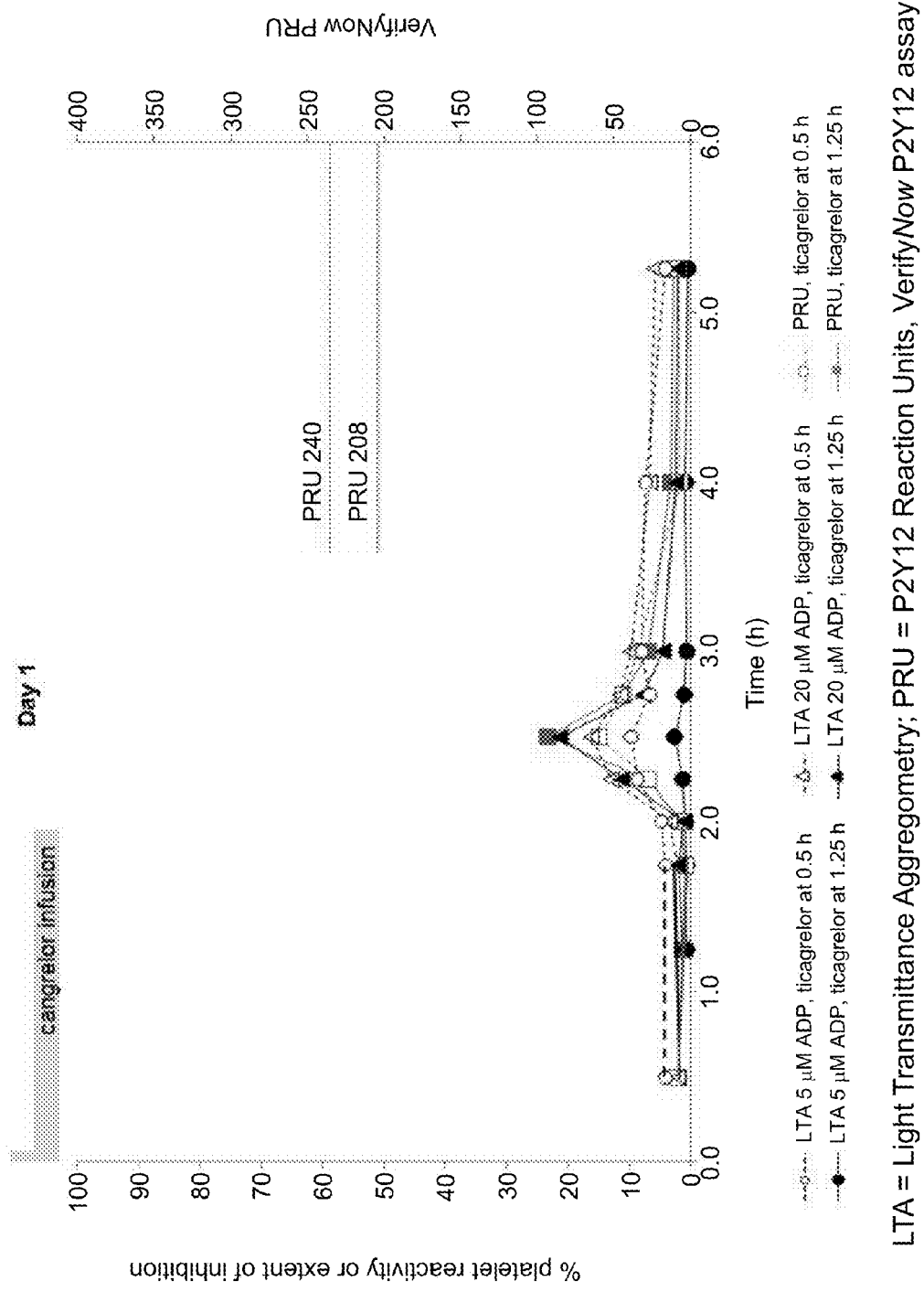
FIG. 13 shows LTA induced by 5 and 20 μM ADP and platelet reactivity measured by the VerifyNow® P2Y12 assay in patients administered with 180 mg of ticagrelor during (at 0.5 hr or 1.25 hr)

ACEI = angiotensin converting enzyme inhibitor; ARB = angiotensin receptor blocker; Ca = calcium; CABG = coronary artery bypass graft; MI = myocardial infarction; PCI = percutaneous coronary intervention;

The final (after 5 min) aggregation measured by LTA was extensively and consistently inhibited during the infusion of cangrelor, as shown in FIG. 12 Residual platelet reactivity was <4% and the extent of inhibition was >95% when cangrelor was being infused. Previous treatment with ticagrelor did not alter the inhibitory effect of cangrelor, and consistent pharmacodynamic effects were apparent with each of the secondary measures of platelet function, as shown in Table 22 and in FIG. 13.

TABLE 22

Pharmacodynamic effects of cangrelor.

| | | Study Day 1 | | | | Study Day 5 | |
|---|---|---|---|---|---|---|---|
| 20 µM ADP, LTA | | Reference 0.5/1.25 h | 1.75 h | 2.0 h | | 1.0 h | 2.0 h |
| All (n = 12) | PR | 1.7 ± 1.7 | 2.2 ± 1.4 | 2.3 ± 2.2 | All (n = 12) | 1.5 ± 1.5 | 1.3 ± 1.6 |
| | IPA | 98 ± 2 | 97 ± 2 | 97 ± 3 | | 98 ± 2 | 98 ± 2 |
| Ticagrelor at 1.25 hr (n = 6) | PR | 1.3 ± 2.0 | 2 ± 1.8 | 1.2 ± 1.9 | Ticagrelor 6 doses (n = 6) | 1.5 ± 1.6 | 1.2 ± 1.5 |
| | IPA | 98 ± 3 | 97 ± 3 | 98 ± 3 | | 98 ± 2 | 98 ± 1 |
| Ticagrelor at 0.5 hr (n = 6) | PR | 2 ± 1.5 | 2.3 ± 1.0 | 3.5 ± 1.9 | Ticagrelor 7 doses (n = 6) | 1.5 ± 1.5 | 1.5 ± 1.9 |
| | IPA | 97 ± 2 | 97 ± 2 | 95 ± 2 | | 98 ± 2 | 98 ± 3 |
| 5 µM ADP, LTA | | | | | | | |
| All (n = 12) | PR | 3.6 ± 1.8 | 3.4 ± 2.2 | 4.1 ± 2 | All (n = 12) | 2.1 ± 1.7 | 2.2 ± 2.2 |
| | IPA | 93 ± 3 | 92 ± 5 | 92 ± 3 | | 96 ± 3 | 96 ± 4 |
| Ticagrelor at 1.25 hr (n = 6) | PR | 3 ± 1.4 | 2.7 ± 1.8 | 3.3 ± 2 | Ticagrelor 6 doses (n = 6) | 1.5 ± 1.6 | 1.5 ± 1.5 |
| | IPA | 93 ± 2 | 93 ± 6 | 93 ± 3 | | 96 ± 4 | 97 ± 3 |
| Ticagrelor at 0.5 hr (n = 6) | PR | 4.2 ± 2.1 | 4.2 ± 2.4 | 4.8 ± 1.9 | Ticagrelor 7 doses (n = 6) | 2.7 ± 1.6 | 2.8 ± 2.7 |
| | IPA | 92 ± 4 | 92 ± 5 | 91 ± 3 | | 96 ± 3 | 95 ± 5 |
| VerifyNow ® | | | | | | | |
| All (n = 12) | PRU | 7.3 ± 9.3 | 3.8 ± 2.6 | 6.4 ± 7.5 | All (n = 12) | 3.3 ± 2 | 4.5 ± 6.4 |
| | IPR | 97 ± 3 | 99 ± 1 | 98 ± 3 | | 99 ± 1 | 98 ± 3 |
| Ticagrelor at 1.25 hr (n = 6) | PRU | 5.8 ± 7.3 | 3.7 ± 2.8 | 5.9 ± 9.9 | Ticagrelor 6 doses (n = 6) | 2.8 ± 1.9 | 2.4 ± 1.9 |
| | IPR | 98 ± 3 | 99 ± 1 | 98 ± 4 | | 99 ± 1 | 99 ± 1 |
| Ticagrelor at 0.5 hr (n = 6) | PRU | 8.8 ± 12 | 3.8 ± 2.6 | 6.9 ± 4.9 | Ticagrelor 7 doses (n = 6) | 3.9 ± 2.1 | 6.5 ± 8.8 |
| | IPR | 97 ± 4 | 99 ± 1 | 97 ± 2 | | 98 ± 1 | 97 ± 3 |
| VASP Index | | | | | | | |
| All (n = 12) | VI | 18 ± 10 | 13 ± 9 | 15 ± 9 | All (n = 12) | 16 ± 11 | 17 ± 5 |
| Ticagrelor at 1.25 hr (n = 6) | VI | 19 ± 8 | 13 ± 4 | 19 ± 7 | Ticagrelor 6 doses (n = 6) | 19 ± 14 | 20 ± 3 |
| Ticagrelor at 0.5 hr (n = 6) | VI | 18 ± 13 | 13 ± 9 | 11 ± 7 | Ticagrelor 7 doses (n = 6) | 12 ± 7 | 14 ± 6 |
| Flow Cytometry | | | | | | | |
| All (n = 12) | PR | 2.8 ± 1.2 | 2.5 ± 1 | 3.8 ± 4.5 | All (n = 12) | 4.1 ± 2.7 | 2.8 ± 1.3 |
| | IPR | 94 ± 4 | 94 ± 5 | 89 ± 30 | | 92 ± 4 | 95 ± 3 |
| Ticagrelor at 1.25 hr (n = 6) | PR | 1.5 ± 0.5 | 3 ± 1.1 | 5.3 ± 6.3 | Ticagrelor 6 doses (n = 6) | 3.5 ± 1.4 | 2.7 ± 1.2 |
| | IPR | 94 ± 3 | 92 ± 7 | 83 ± 28 | | 91 ± 3 | 93 ± 3 |
| Ticagrelor at 0.5 hr (n = 6) | PR | 3 ± 1.7 | 2 ± 0.6 | 2.3 ± 0.8 | Ticagrelor 7 doses (n = 6) | 4.7 ± 3.6 | 2.8 ± 1.5 |
| | IPR | 94 ± 5 | 96 ± 2 | 96 ± 2 | | 93 ± 5 | 96 ± 2 |

IPA/R = inhibition of platelet aggregation/reactivity; LTA = final (5 min) light transmission aggregometry; PR = platelet reactivity; PRU = P2Y12 reaction units; VASP = vasodilator-stimulated phosphoprotein; for flow cytometry P-selectin expression in response to 1 µM ADP shown, PAC-1 binding (not shown) was comparable

TABLE 23

Pharmacodynamic effects of ticagrelor.

| 20 μM ADP, LTA | | Reference 5.25 h | 2.25 h | 2.5 h | 2.75 h | 3 h | 4 h |
|---|---|---|---|---|---|---|---|
| All (n = 12) | PR | 4 ± 3.4 | 12 ± 11 | 19 ± 16 | 10 ± 9.2 | 7.1 ± 6.3 | 4.6 ± 3.6 |
|  | IPA | 95 ± 4 | 83 ± 14 | 72 ± 26 | 86 ± 15 | 90 ± 9 | 94 ± 4 |
| Ticagrelor at 1.25 h (n = 6) | PR | 2.2 ± 2.7 | 11 ± 12 | 21 ± 17 | 7.8 ± 7.2 | 4.5 ± 3.4 | 2.5 ± 1.9 |
|  | IPA | 97 ± 4 | 84 ± 17 | 65 ± 30 | 87 ± 15 | 93 ± 7 | 96 ± 4 |
| Ticagrelor at 0.5 h (n = 6) | PR | 5.8 ± 3.1 | 13 ± 9.3 | 16 ± 15 | 12 ± 11 | 10 ± 7.6 | 6.7 ± 3.7 |
|  | IPA | 92 ± 4 | 82 ± 13 | 78 ± 21 | 84 ± 15 | 87 ± 10 | 91 ± 4 |
| 5 μM ADP, LTA | | | | | | | |
| All (n = 12) | PR | 3.1 ± 2.8 | 7 ± 5 | 10 ± 7 | 5.8 ± 3 | 5.5 ± 5.2 | 5.5 ± 3.3 |
|  | IPA | 94 ± 5 | 87 ± 8 | 79 ± 15 | 86 ± 11 | 86 ± 17 | 88 ± 9 |
| Ticagrelor at 1.25 h (n = 6) | PR | 2 ± 2.3 | 5.3 ± 3.6 | 11 ± 9 | 4.8 ± 0.8 | 3 ± 1.5 | 3.7 ± 1 |
|  | IPA | 97 ± 4 | 89 ± 5 | 76 ± 18 | 85 ± 15 | 87 ± 21 | 89 ± 12 |
| Ticagrelor at 0.5 h (n = 6) | PR | 4.2 ± 2 | 7.7 ± 5.9 | 10 ± 5.7 | 6.7 ± 4.1 | 8 ± 6.5 | 7.3 ± 3.9 |
|  | IPA | 92 ± 6 | 84 ± 10 | 82 ± 13 | 87 ± 7 | 85 ± 15 | 87 ± 5 |
| VerifyNow ® | | | | | | | |
| All (n = 12) | PRU | 9.5 ± 9.7 | 28 ± 28 | 76 ± 79 | 44 ± 50 | 31 ± 46 | 10 ± 10 |
|  | IPR | 96 ± 4 | 89 ± 11 | 70 ± 31 | 83 ± 21 | 88 ± 19 | 96 ± 4 |
| Ticagrelor at 1.25 h (n = 6) | PRU | 11 ± 7 | 28 ± 32 | 93 ± 94 | 44 ± 62 | 28 ± 53 | 14 ± 14 |
|  | IPR | 96 ± 4 | 89 ± 14 | 62 ± 37 | 82 ± 27 | 88 ± 23 | 95 ± 5 |
| Ticagrelor at 0.5 h (n = 6) | PRU | 7.7 ± 5.3 | 28 ± 27 | 60 ± 64 | 44 ± 40 | 35 ± 42 | 7.3 ± 4.4 |
|  | IPR | 97 ± 2 | 90 ± 10 | 78 ± 24 | 84 ± 15 | 87 ± 16 | 97 ± 2 |
| VASP Index | | | | | | | |
| All (n = 12) | VI | 12 ± 12 | 35 ± 10 | 48 ± 49 | 22 ± 16 | 25 ± 19 | 17 ± 14 |
| Ticagrelor at 1.25 h (n = 6) | VI | 14 ± 15 | 32 ± 11 | 54 ± 32 | 22 ± 20 | 26 ± 20 | 19 ± 16 |
| Ticagrelor at 0.5 h (n = 6) | VI | 11 ± 10 | 37 ± 8 | 41 ± 25 | 21 ± 13 | 24 ± 19 | 16 ± 14 |
| Flow Cytometry | | | | | | | |
| All (n = 12) | PR | 5 ± 3.6 | 7.8 ± 3.7 | 14 ± 8.6 | 8.8 ± 5.6 | 6.5 ± 4.1 | 7.5 ± 6.2 |
|  | IPR | 91 ± 6 | 84 ± 8 | 67 ± 29 | 80 ± 17 | 86 ± 13 | 84 ± 15 |
| Ticagrelor at 1.25 h (n = 6) | PR | 4.5 ± 2 | 8 ± 4.9 | 19 ± 8.5 | 8.3 ± 6.9 | 6.2 ± 5.3 | 9.5 ± 8.2 |
|  | IPR | 91 ± 7 | 83 ± 9 | 53 ± 34 | 79 ± 22 | 86 ± 16 | 78 ± 20 |
| Ticagrelor at 0.5 h (n = 6) | PR | 5.5 ± 3.9 | 7.5 ± 2.4 | 9.2 ± 5.9 | 9.3 ± 4.7 | 6.8 ± 2.9 | 5.5 ± 2.4 |
|  | IPR | 91 ± 4 | 86 ± 8 | 81 ± 17 | 82 ± 13 | 87 ± 10 | 90 ± 4 |

IPA/R = inhibition of platelet aggregation/reactivity; LTA = final (5 min) light transmission aggregometry; PR = platelet reactivity; PRU = P2Y12 reaction units; VASP = vasodilator-stimulated phosphoprotein; for flow cytometry P-selectin expression in response to 1 μM ADP shown, PAC-1 binding (not shown) was comparable A modest increase in platelet reactivity was apparent during the first hour after discontinuation of cangrelor (see FIGS. 12 and 13). The increment was not significantly different than the reference time point (5.25 hr). Administration of ticagrelor earlier (at 0.5 hr rather than 1.25 hr) appeared to attenuate the increase in residual platelet reactivity and augment the extent of inhibition that was apparent. The residual platelet reactivity seen at 2.5 hr when ticagrelor was given at 0.5 hr (16±15%) was comparable to the residual platelet reactivity seen 12 hours after the last dose of ticagrelor measured on study day 5 (12±9%).

In the combined overall population, residual reactivity was maximal at 19% 0.5 h after cangrelor was stopped, and then decreased again to <5% at the end of the observation period (5.25 h). This recovery of function is not likely to have clinical implications because the effect is modest, transient, and very low platelet reactivity is maintained throughout the transition period. The extent of platelet reactivity throughout the transition time was consistent with the presence of $P2Y_{12}$ inhibition, and well below thresholds known to be associated with an increased risk of thrombotic events.

For the transition between ticagrelor and cangrelor on Day 5, there was no apparent interaction between the drugs regardless of whether the ticagrelor had been discontinued 12 or 24 h prior to initiation of the cangrelor infusion.

No serious adverse events (ischemic or bleeding) occurred during the trial. Other adverse events are summarized in Table 24.

TABLE 24

Other Adverse Events.
Frequency Threshold Above Which Other Adverse Events are Reported: 0%

|  | Cangrelor + Ticagrelor 90 mg (6 Doses) | Cangrelor + Ticagrelor 90 mg (7 Doses) |
|---|---|---|
| Total No. of participants affected/at risk | 1/6 (16.67%) | 1/6 (16.67%) |
| General Disorders Edema peripheral | | |
| No. of participants affected/at Risk | 0/6 (0%) | 1/6 (16.67%) |
| No. of events | 0 | 1 |

TABLE 24-continued

Other Adverse Events.
Frequency Threshold Above Which Other Adverse Events are Reported: 0%

| | Cangrelor + Ticagrelor 90 mg (6 Doses) | Cangrelor + Ticagrelor 90 mg (7 Doses) |
|---|---|---|
| Respiratory, thoracic and mediastinal disorders | | |
| Dyspnea | | |
| No. of participants affected/at Risk | 1/6 (16.67%) | 0/6 (0%) |
| No. of events | 1 | 0 |

The pharmacodynamic assessment demonstrated that residual platelet reactivity during infusion of cangrelor was limited regardless of whether ticagrelor was given during the infusion or ticagrelor had been given before infusion. Terminal aggregation of platelets in response to 20 µM ADP, the residual platelet reactivity was less than 5% and the extent of inhibition was greater than 95% during cangrelor treatment.

During the transition from cangrelor to ticagrelor, a modest, non-significant increase in platelet reactivity was observed during the first hour after cangrelor was stopped. Earlier administration of ticagrelor appeared to attenuate the increase in platelet reactivity.

Comparison of results obtained after an equivalent interval raises the possibility of a modest interaction. For patients given ticagrelor at 1.25 hr (which is 0.75 hr before cangrelor was stopped), the residual platelet reactivity and extent of inhibition seen 1.75 hr after the loading dose (at 3.0 hr) were 4.5±3.4% and 93±7%. For patients given ticagrelor at 0.5 hr, results 1.75 hr later (at 2.25 hr) were 13±9.3% and 82±13%.

In conclusion, ticagrelor given before or during infusion of cangrelor did not attenuate the pharmacodynamic effects of cangrelor. In addition, the pharmacodynamic effects of ticagrelor were preserved when ticagrelor was given during infusion of cangrelor. Consistent with the reversible binding of ticagrelor, this oral $P2Y_{12}$ antagonist can be administered before, during or after treatment with cangrelor. Consistent with its pharmacokinetics, the pharmacodynamic effects will be greater when ticagrelor is given earlier.

Example 5

Population Pharmacodynamic Evaluation of Cangrelor

Objective

The objective of this evaluation was to develop a population pharmacodynamic model to describe the concentration effect relationship between cangrelor exposure and the marker of platelet aggregation, namely P2Y12 reaction units (PRU), as measured by VerifyNow®, Accumetrics in order to, among other things, determine how best to transition from the bridge dose to the PCI dose, and vice versa.

Data and Database Creation

The database created for this evaluation included a total of 1102 PRU observations from 220 bridge and PCI patients. A summary of the demographics is provided in Table 25. These patients were generally older and heavier than volunteers.

TABLE 25

Summary of the Demographics of the Patients Involved in the Study.

| Covariate (units) | Mean | Median | SD | Max | Min |
|---|---|---|---|---|---|
| Age (yrs) | 63 | 62 | 11 | 92 | 36 |
| Weight (kg) | 86.8 | 85.4 | 16 | 154 | 52 |
| BMI (kg/m2) | 29.5 | 29.1 | 5.07 | 50.1 | 19.4 |

| Sex | Male | Female |
|---|---|---|
| Number | 161 | 59 |

| Study | CHAMPION PCI/Platform (PCI) Platelet Substudy | Bridge |
|---|---|---|
| Number | 104 | 116 |

| Patient type | PCI | ACS | Stent |
|---|---|---|---|
| Number | 54 | 69 | 97 |

| Treatment Group | PCI/substudy, 30 µg/kg bolus + 4 µg/kg/min infusion | Cohort 1: 0.5 µg/kg/min | Cohort 1: 0.75 µg/kg/min | Cohort 2: 0.75 µg/kg/min |
|---|---|---|---|---|
| Number | 104 | 5 | 6 | 105 |

ACS denotes acute coronary syndrome. PCI denotes percutaneous coronary intervention.

Simulation Assessments

In order to address the pharmacodynamic objectives and show how best to transition from one dose to the other dose (i.e., Bridge and PCI), stochastic simulation was performed in NONMEM. A PRU value of 208 was chosen throughout the evaluation as the cutoff to evaluate the effectiveness of varying doses of cangrelor in different patient types. The results were evaluated graphically by generating 95% confidence intervals and by summarizing the percentage of patients expected to achieve a PRU value of 208 or less. For each simulation scenario, 1000 patients were simulated using covariates drawn from the original distribution of covariate values. Parameter precision was not taken into account for these simulations.

Patients from the bridge subset of data were sampled. At varying times after initiation of the bridge dose, the patient type was switched to the PCI type (to reflect reduced sensitivity to cangrelor) and the dose was increased to the PCI dose. The percentage of subjects achieving the desired PRU result of 208 or lower were tabulated. For completeness, the reverse transition (from PCI to bridge) was also simulated, and results tabulated.

Description of PRU Pharmacodynamic Model

The PRU pharmacodynamic model was a direct effect sigmoidal inhibitory model with terms describing the between subject variability included on the drug effect parameter (Emax) and baseline. An additive residual error was used. The model incorporated a slowly increasing baseline in bridge patients (attributable to the effect of previous dosing with clopidogrel wearing off) and a slowly decreasing baseline in PCI patients (owing to the thrombotic stimulus of the stenting/PCI gradually lessening after the procedure together with onset of effect of other post procedure treatments). The model also included a covariate for patient type on drug effect and the effects of age and sex on baseline. The equations for the final PRU pharmacodynamic model are provided below.

$$\text{Baseline}PRU = \theta_6 * (1 - \text{sex} * \theta_{11}) * \left(\frac{\text{Age}}{30}\right)^{\theta_{33}} * \exp(\eta 5)$$

$$\text{Eff} = \theta_7 * (1 - \text{patient type} * \theta_{10}) * \exp(\eta 4)$$

$$IC50 = \theta_8$$

$$\gamma = \theta_9$$

$$\text{If}(\text{Study} = 1) \text{wearoff} = \theta_{12} \text{ else } \theta_{14}$$

$$\text{DrugEffect} = \frac{\text{Eff} * Cp^\gamma}{IC50^\gamma + Cp^\gamma}$$

$$PRU = \text{Baseline } PRU - \text{DrugEffect} - \text{wearoff} * \text{Time(hrs)}$$

The parameters were estimated with good precision with the exception of the age effect on baseline. All other diagnostics and model evaluations suggested that the model performance was acceptable. The parameters from the model are provided in Table 26.

TABLE 26

Parameter estimates for base PRU pharmacodynamic model.

| Parameter (Units) | Population Mean | SE (CV %) | Between Subject Variability | SE (CV %) |
|---|---|---|---|---|
| Baseline | 215 | 7 | 23.22 | 15 |
| Wear off PCI (l/h) | −3.15 | 13.7 | | |
| Wear off bridge (l/h) | 0.838 | 7.3 | | |
| Age effect | 0.228 | 39.7 | | |
| Gender effect | −0.162 | 25.3 | | |
| Drug Effect | 148 | 6.2 | 19.21 | 31.7 |
| PCI patient effect | −0.624 | 17 | | |

TABLE 26-continued

Parameter estimates for base PRU pharmacodynamic model.

| Parameter (Units) | Population Mean | SE (CV %) | Between Subject Variability | SE (CV %) |
|---|---|---|---|---|
| IC50 | 0.0717 | 35.4 | NE | NE |
| Gamma | 1.71 | 21 | NE | NE |
| Additive Residual Error | 62.6 | | 2.7 | |

NE-not estimated.

Several covariates were identified in this evaluation. There was an effect of gender on the baseline PRU, with females having a 16% higher baseline PRU than males. Age was also found to be important on the baseline PRU value. The impact of age is provided in Table 27.

TABLE 27

Effect of age on baseline PRU.

| Age (yrs) | Baseline PRU | Percent of Reference |
|---|---|---|
| 30 | 215 | 100 |
| 40 | 230 | 107 |
| 50 | 242 | 112 |
| 60 | 252 | 117 |
| 70 | 261 | 121 |
| 80 | 269 | 125 |

Figure 14:
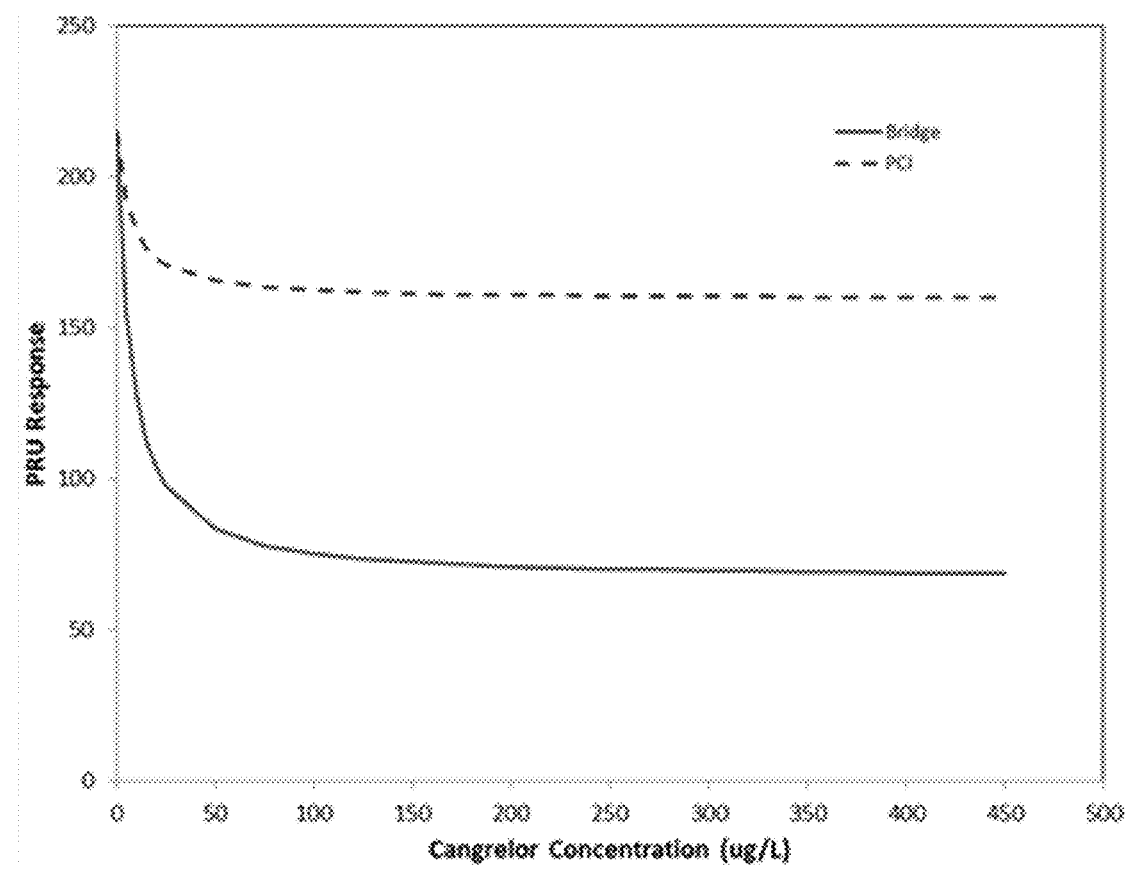
FIG. 14 shows the PD model of PRU responses versus cangrelor concentration for patients receiving a PCI dosing regimen and for patients receiving a bridge dosing regimen.

Over the age range from 30 to 80 years, the baseline PRU would be expected to increase by 25%. There was a larger impact of patient type (i.e., PCI patient versus bridge patient) on the drug effect which is shown in FIG. 14. This impact is a 62% decreased effect in PCI relative to bridge and shows why the percentage of simulated PCI patients achieving the threshold response of 208 is somewhat lower than seen in the bridge patients.

Simulation Results: Evaluation of the Probability of Achieving the Desired PRU Cutoff The probability of the PCI and bridge patients achieving the desired PRU cutoff value of 208 is provided for the overall indication in Table 28.

TABLE 28

Probability of achieving desired PRU result by patient type - overall findings.

| Study | Patient Type | Dose | Probability |
|---|---|---|---|
| 1 | PCI | 30 μg/kg bolus with 4 μg/kg/min | 0.827462 |
| 2 | Bridge | 0.75 μg/kg/min | 0.961949 |

As can be seen, despite the lower dose used for the bridge patients, the probability of achieving the threshold is higher in these patients than the PCI patients because the PCI patients had a higher immediate thrombotic stimulus.

Similarly the probability of maintaining the PRU below the threshold after stratification of patients by weight over the range of weights in the database showed no overall trends (Table 29), suggesting that the drug concentration is sufficient to provide approximately 80% at or below threshold for PCI patients and over 90% at or below threshold PRU for bridge patients with the suggested dose.

TABLE 29

Probability of achieving desired PRU result by patient type and weight.

| Study | Patient Type | Dose | Weight Range (kg) | Probability |
|---|---|---|---|---|
| 1 | PCI | 30 µg/kg bolus with 4 µg/kg/min | (50, 80) | 0.839885 |
| 1 | PCI | 30 µg/kg bolus with 4 µg/kg/min | (80, 90) | 0.795222 |
| 1 | PCI | 30 µg/kg bolus with 4 µg/kg/min | (90, 100) | 0.7975 |
| 1 | PCI | 30 µg/kg bolus with 4 µg/kg/min | (100, 120) | 0.87275 |
| 1 | PCI | 30 µg/kg bolus with 4 µg/kg/min | (120, 160) | 0.856 |
| 2 | Bridge | 0.75 µg/kg/min | (50, 80) | 0.95797 |
| 2 | Bridge | 0.75 µg/kg/min | (80, 90) | 0.98004 |
| 2 | Bridge | 0.75 µg/kg/min | (90, 100) | 0.952081 |
| 2 | Bridge | 0.75 µg/kg/min | (100, 120) | 0.957313 |
| 2 | Bridge | 0.75 µg/kg/min | (120, 160) | 0.9915 |

There was no marked trend in the probability of patients achieving the threshold with age (Table 30).

TABLE 30

Probability of achieving desired PRU result by patient type and age.

| Study | Patient Type | Dose | Age Range (yrs) | Probability |
|---|---|---|---|---|
| 1 | PCI | 30 µg/kg bolus with 4 µg/kg/min | (30, 50) | 0.896722 |
| 1 | PCI | 30 µg/kg bolus with 4 µg/kg/min | (50, 60) | 0.806719 |
| 1 | PCI | 30 µg/kg bolus with 4 µg/kg/min | (60, 70) | 0.836735 |
| 1 | PCI | 30 µg/kg bolus with 4 µg/kg/min | (70, 80) | 0.778786 |
| 1 | PCI | 30 µg/kg bolus with 4 µg/kg/min | (80, 100) | 0.791333 |
| 2 | Bridge | 0.75 µg/kg/min | (30, 50) | 0.994444 |
| 2 | Bridge | 0.75 µg/kg/min | (50, 60) | 0.98919 |
| 2 | Bridge | 0.75 µg/kg/min | (60, 70) | 0.984217 |
| 2 | Bridge | 0.75 µg/kg/min | (70, 80) | 0.93135 |
| 2 | Bridge | 0.75 µg/kg/min | (80, 100) | 0.869444 |

There was no marked trend in the probability of patients achieving the threshold with gender (Table 31).

TABLE 31

Probability of achieving desired PRU result by patient type and sex.

| Study | Patient Type | Dose | Sex | probability |
|---|---|---|---|---|
| 1 | PCI | 30 µg/kg bolus with 4 µg/kg/min | Male | 0.866044 |
| 1 | PCI | 30 µg/kg bolus with 4 µg/kg/min | Female | 0.754583 |
| 2 | Bridge | 0.75 µg/kg/min | Male | 0.982444 |
| 2 | Bridge | 0.75 µg/kg/min | Female | 0.901222 |

These results support the selection of a higher dose for PCI patients than for Bridge patients and suggest that there should be no need to adjust dose for age or gender.

Simulation Results: Transition from Bridge to PCI

Figure 15:
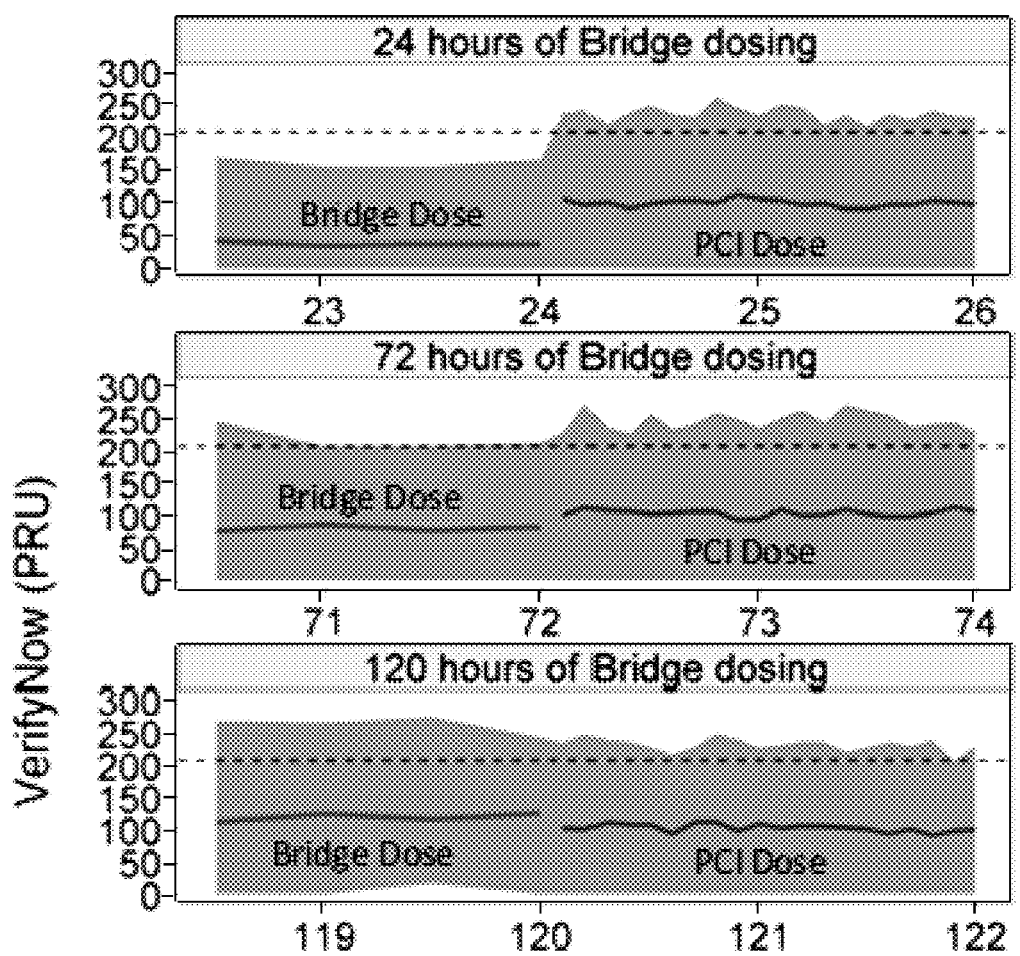
FIG. 15 shows a simulated range of PRU responses for a male patient, 62 yrs and 90 kg with IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 16:
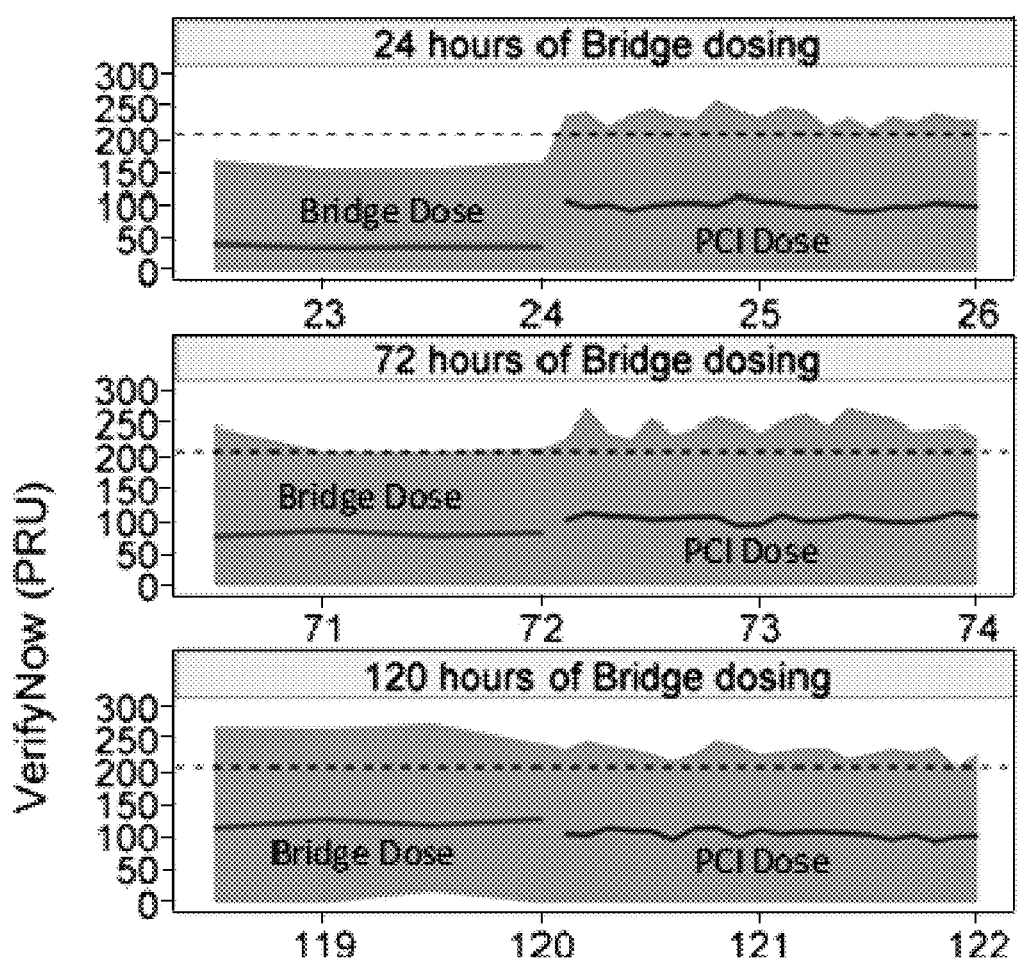
FIG. 16 shows a simulated range of PRU responses for a male patient, 62 yrs and 90 kg with no IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 17:
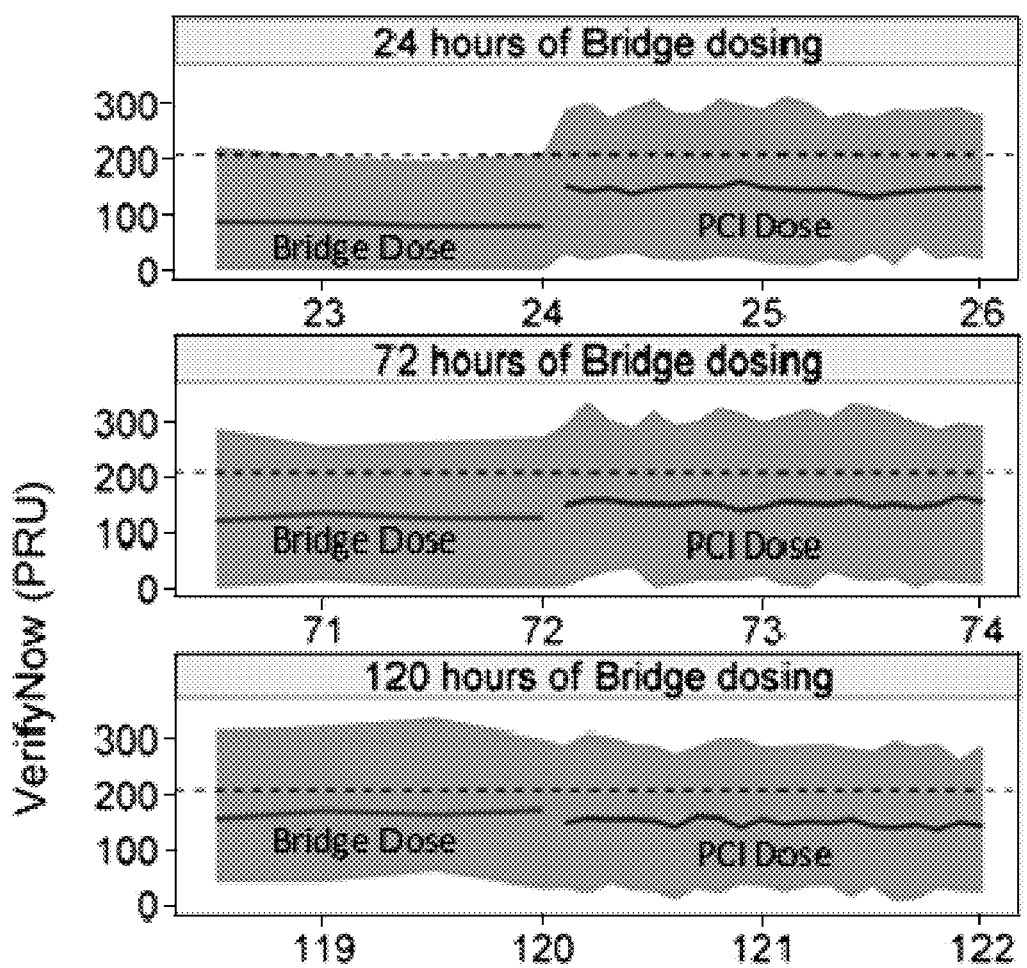
FIG. 17 shows a simulated range of PRU responses for a female patient, 66 yrs and 60 kg with IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)
Figure 18:
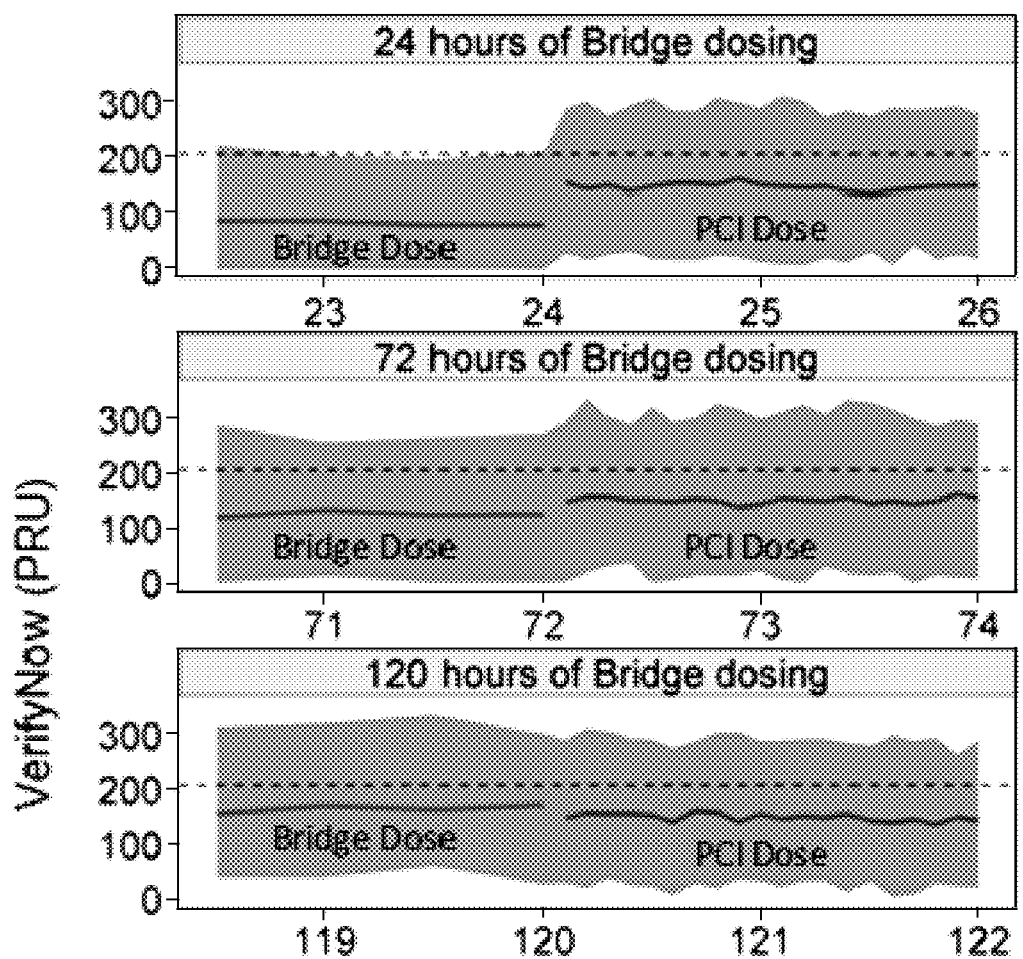
FIG. 18 shows a simulated range of PRU responses for a female patient, 66 yrs and 60 kg with no IV bolus loading dose for PCI, transitioning from the bridge dosing regimen to the PCI dosing regimen (the shaded areas are the confidence intervals about the lines and the dashed line is the cut-off PRU value of 208, associated high sensitivity and specificity for the presence of $P2Y_{12}$ inhibition)

The results of the simulated transition from the bridge setting (0.75 µg/kg/min) to the PCI setting (4 µg/kg/min) with and without the administration of an IV bolus loading dose for PCI (30 µg/kg) are provided for a reference male patient in FIG. 15 and FIG. 16, respectively. As was seen with the evaluation of probability of achieving the threshold PRU response, the probability is generally lower for the PCI than bridge patient in all settings. The same scenarios were simulated in a reference female patient with and without the IV bolus dose (FIG. 17 and FIG. 18, respectively). The benefit of adding a bolus dose when transitioning from bridge to PCI is somewhat limited, but the probability of maintaining the PRU value below 208 is higher with the recommended loading dose than without such IV bolus dose prior to PCI.

Simulation Results: Transition from PCI to Bridge

Figure 19:
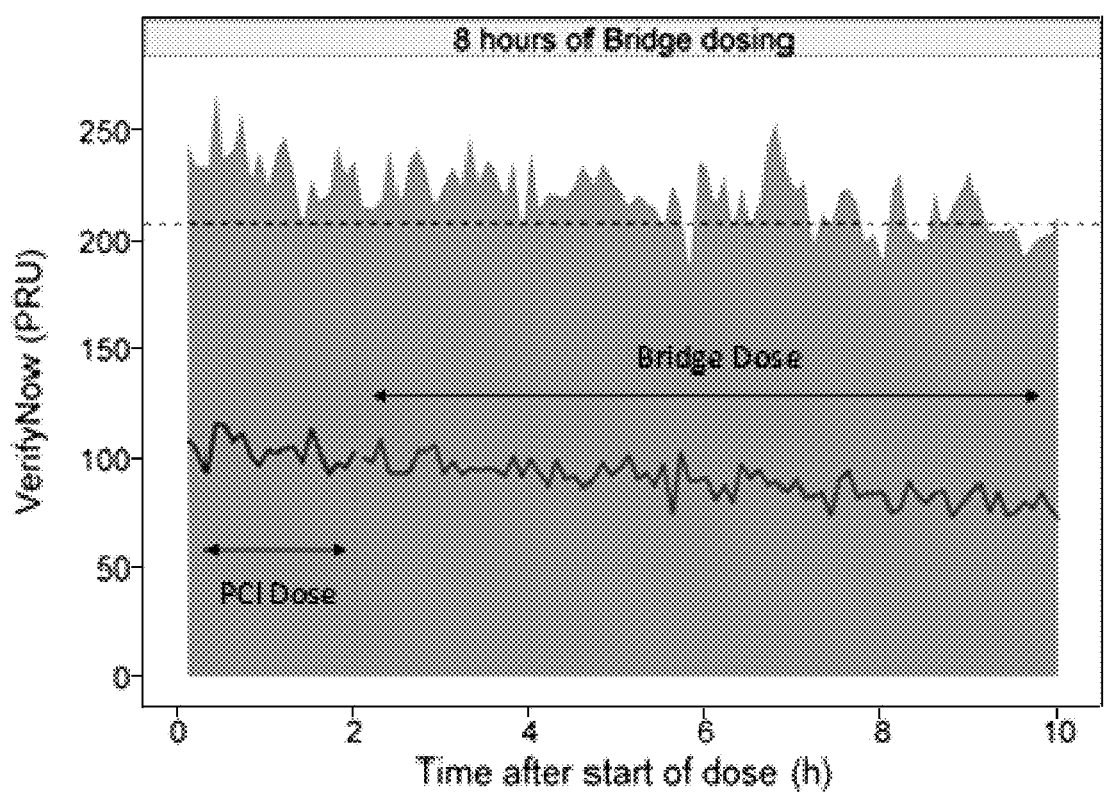
FIG. 19 shows a simulated range of PRU responses for male patient, 62 yrs and 90 kg, transitioning from the PCI dosing regimen to the bridge dosing regimen (the shaded areas are the confidence intervals about the lines and the dashed line is the cut-off PRU value of 208, associated high sensitivity and specificity for the presence of $P2Y_{12}$ inhibition)
Figure 20:
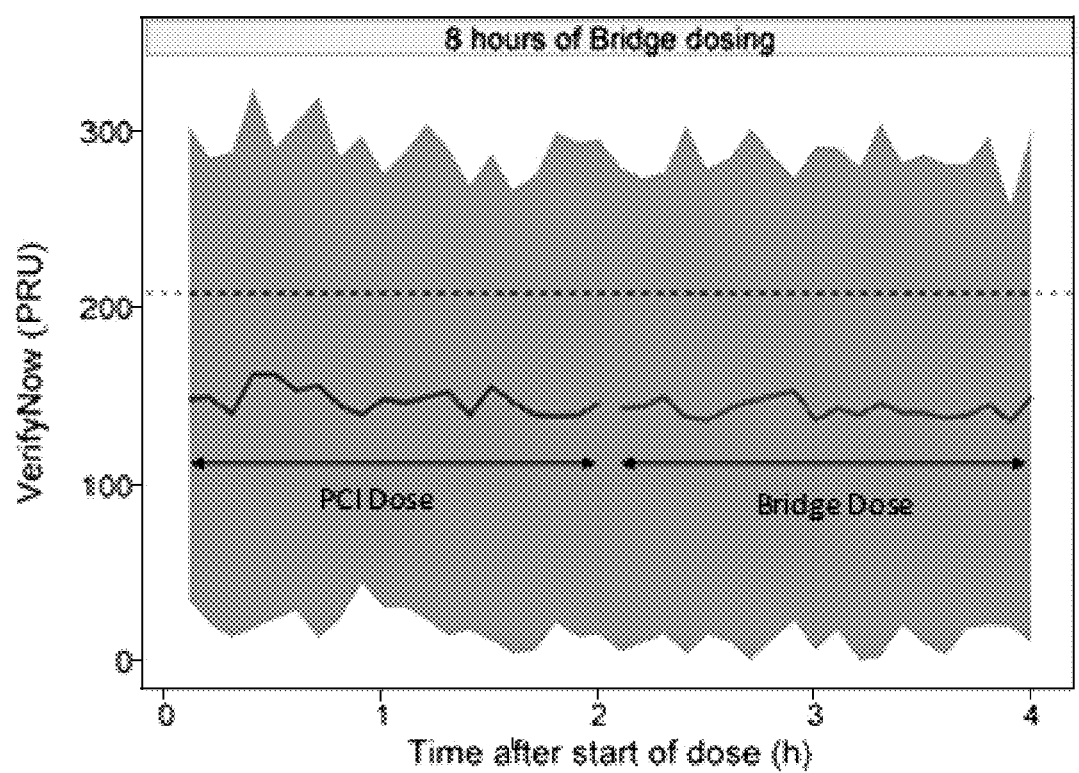
FIG. 20 shows a simulated range of PRU responses for female patient, 66 yrs and 60 kg, transitioning from the PCI dosing regimen to the bridge dosing regimen (the shaded areas are the confidence intervals about the lines and the dashed line is the cut-off PRU value of 208, associated high sensitivity and specificity for the presence of $P2Y_{12}$ inhibition).

The results of the stochastic simulations from the PCI setting (30 µg/kg bolus with 4 µg/kg/min) to the bridge setting (0.75 µg/kg/min) are provided for the same virtual male and female patient in FIG. 19 and FIG. 20, respectively. In these simulations, patients received the recommended PCI dose for 2 hours, then were transitioned directly to the recommended bridge dose for 8 hours. PRU samples were taken hourly. However because these virtual patients were simulated to reflect a PCI patient (and who would not therefore have had a high dose of cangrelor prior to PCI), the wearing off effect seen with the bridge study was turned off. However the ability of a subject to respond to cangrelor was changed once bridge dosing was initiated.

Although these figures suggest a substantial difference between males and females, the determined probability of achieving a PRU below the threshold of 208 was similar. Thus these figures reflect the inherent variability of the PRU assay more than any difference in inherent responsiveness to treatment.

The results of the stochastic simulations suggest that when transitioning from the bridge setting to the PCI setting, or vice versa, there is no need to modify the cangrelor dosing (e.g., dose titration) from that which is routinely used for these indications. PCI patients being transitioned to surgery can be switched from 4 µg/kg/min cangrelor directly to 0.75 µg/kg/min cangrelor. Surgical patients being transitioned to PCI can be switched directly from 0.75 µg/kg/min cangrelor to 4 µg/kg/min cangrelor, either with or without the 30 µg/kg bolus cangrelor dose

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of transitioning a patient from administration of cangrelor during percutaneous coronary intervention (PCI) to administration of ticagrelor for chronic treatment, the method comprising:
   (1) administering intravenously a 30 μg/kg bolus of cangrelor before the start of PCI;
   (2) administering intravenously a 4 μg/kg/min continuous infusion of cangrelor after administration of the bolus;
   (3) continuing the administration of the continuous infusion for the longer of (a) at least two hours, or (b) the duration of PCI; and
   (4) administering an oral dose of ticagrelor either (a) during administration of the continuous infusion, or (b) after discontinuation of the administration of the continuous infusion, wherein the oral dose comprises a 180 mg loading dose of ticagrelor.

2. The method of claim 1, wherein the patient received oral $P2Y_{12}$ therapy prior to the administration of cangrelor without attenuation of the effect of cangrelor.

3. The method of claim 2, wherein the oral $P2Y_{12}$ therapy is selected from the group consisting of clopidogrel, prasugrel, and ticagrelor.

4. The method of claim 1, wherein cangrelor is in a pharmaceutical composition comprising 200 μg/mL of cangrelor.

5. The method of claim 4, wherein the pharmaceutical composition further comprises sodium chloride injection 0.9% or 5% dextrose injection.

6. The method of claim 1, wherein the bolus is administered in less than one minute.

7. The method of claim 1, wherein the continuous infusion is continued for a total duration of up to about four hours.

8. The method of claim 1, wherein the method further comprises administering one or more oral doses of ticagrelor subsequent to the loading dose.

9. The method of claim 8, wherein the one or more subsequent oral doses comprise 90 mg of ticagrelor.

10. The method of claim 1, wherein the administration of the continuous infusion is started immediately after the administration of the bolus.

11. The method of claim 1, wherein the method further comprises administering aspirin before or during administration of the continuous infusion.

12. A method of transitioning a patient from administration of cangrelor during percutaneous coronary intervention (PCI) to administration of ticagrelor for chronic treatment, the method comprising:
   (1) administering intravenously a 30 μg/kg bolus of cangrelor before the start of PCI;
   (2) administering intravenously a 4 μg/kg/min continuous infusion of cangrelor after administration of the bolus;
   (3) continuing the administration of the continuous infusion of cangrelor for the longer of (a) at least two hours, or (b) the duration of PCI; and
   (4) administering an oral dose of ticagrelor during administration of the continuous infusion, wherein the oral dose comprises a 180 mg loading dose of ticagrelor.

13. The method of claim 12, wherein the patient received oral $P2Y_{12}$ therapy prior to the administration of cangrelor without attenuation of the effect of cangrelor.

14. The method of claim 13, wherein the oral $P2Y_{12}$ therapy is selected from the group consisting of clopidogrel, prasugrel, and ticagrelor.

15. The method of claim 12, wherein cangrelor is in a pharmaceutical composition comprising 200 μg/mL of cangrelor.

16. The method of claim 15, wherein the pharmaceutical composition further comprises sodium chloride injection 0.9% or 5% dextrose injection.

17. The method of claim 12, wherein the bolus is administered in less than one minute.

18. The method of claim 12, wherein the continuous infusion is continued for a total duration of up to about 4 hours.

19. The method of claim 12, wherein the method further comprises administering one or more oral doses of ticagrelor subsequent to the loading dose.

20. The method of claim 19, wherein the one or more subsequent oral doses comprise 90 mg of ticagrelor.

21. The method of claim 19, wherein the one or more subsequent oral doses continue after discontinuation of the administration of the continuous infusion.

22. A method of transitioning a patient from administration of cangrelor during percutaneous coronary intervention (PCI) to administration of ticagrelor for chronic treatment, the method comprising:
   (1) administering intravenously a 30 μg/kg bolus of cangrelor before the start of PCI;
   (2) administering intravenously a 4 μg/kg/min continuous infusion of cangrelor after administration of the bolus;
   (3) continuing the administration of the continuous infusion for the longer of (a) at least two hours, or (b) the duration of PCI; and
   (4) administering an oral dose of ticagrelor after discontinuation of the administration of the continuous infusion, wherein the oral dose comprises a 180 mg loading dose of ticagrelor.

23. The method of claim 22, wherein the patient received oral $P2Y_{12}$ therapy prior to the administration of cangrelor without attenuation of the effect of cangrelor.

24. The method of claim 23, wherein the oral $P2Y_{12}$ therapy is selected from the group consisting of clopidogrel, prasugrel, and ticagrelor.

25. The method of claim 22, wherein cangrelor is in a pharmaceutical composition comprising 200 μg/mL of cangrelor.

26. The method of claim 25, wherein the pharmaceutical composition further comprises sodium chloride injection 0.9% or 5% dextrose injection.

27. The method of claim 22, wherein the bolus is administered in less than one minute.

28. The method of claim 22, wherein the continuous infusion is continued for a total duration of up to about 4 hours.

29. The method of claim 22, wherein the method further comprises administering one or more oral doses of ticagrelor subsequent to the loading dose.

30. The method of claim 29, wherein the one or more subsequent oral doses comprise 90 mg of ticagrelor.

* * * * *